(12) United States Patent
Berry et al.

(10) Patent No.: US 8,906,665 B2
(45) Date of Patent: Dec. 9, 2014

(54) METHODS AND COMPOSITIONS FOR THE RECOMBINANT BIOSYNTHESIS OF FATTY ACIDS AND ESTERS

(71) Applicants: David Arthur Berry, Brookline, MA (US); Noubar Boghos Afeyan, Lexington, MA (US); Frank Anthony Skraly, Watertown, MA (US); Christian Perry Ridley, Acton, MA (US); Dan Eric Robertson, Belmont, MA (US); Regina Wilpiszeski, Cambridge, MA (US); Martha Sholl, Haverhill, MA (US)

(72) Inventors: David Arthur Berry, Brookline, MA (US); Noubar Boghos Afeyan, Lexington, MA (US); Frank Anthony Skraly, Watertown, MA (US); Christian Perry Ridley, Acton, MA (US); Dan Eric Robertson, Belmont, MA (US); Regina Wilpiszeski, Cambridge, MA (US); Martha Sholl, Haverhill, MA (US)

(73) Assignee: Joule Unlimited Technologies, Inc., Bedford, MA (US)

(*) Notice: Subject to any disclaimer, the term of this patent is extended or adjusted under 35 U.S.C. 154(b) by 71 days.

(21) Appl. No.: 13/765,211

(22) Filed: Feb. 12, 2013

(65) Prior Publication Data
US 2013/0143306 A1    Jun. 6, 2013

Related U.S. Application Data

(63) Continuation of application No. 13/243,165, filed on Sep. 23, 2011, now Pat. No. 8,399,227, which is a continuation of application No. 12/876,056, filed on Sep. 3, 2010, now Pat. No. 8,048,654, which is a continuation of application No. PCT/US2009/035937, filed on Mar. 3, 2009.

(60) Provisional application No. 61/121,532, filed on Dec. 10, 2008, provisional application No. 61/033,411, filed on Mar. 3, 2008, provisional application No. 61/033,402, filed on Mar. 3, 2008, provisional application No. 61/353,145, filed on Jun. 9, 2010.

(51) Int. Cl.
| | | |
|---|---|---|
| C12N 1/20 | (2006.01) | |
| C12N 9/00 | (2006.01) | |
| C12N 15/79 | (2006.01) | |
| C12P 7/64 | (2006.01) | |

(52) U.S. Cl.
CPC .............. *C12N 15/79* (2013.01); *Y02E 50/17* (2013.01); *C12P 7/649* (2013.01); *C12Y 602/01003* (2013.01); *Y02E 50/13* (2013.01)
USPC ........ 435/252.3; 435/134; 435/183; 435/232; 536/23.2

(58) Field of Classification Search
CPC .................. C12P 7/649; C12Y 602/01003
USPC ....................... 435/183, 252.3, 134; 536/23.2
See application file for complete search history.

(56) References Cited

U.S. PATENT DOCUMENTS

| 4,720,457 A | 1/1988 | Armstrong et al. |
|---|---|---|
| 5,000,000 A | 3/1991 | Ingram et al. |
| 5,162,516 A | 11/1992 | Ingram et al. |
| 5,304,475 A | 4/1994 | Kim et al. |
| 6,429,006 B1 | 8/2002 | Porro et al. |
| 6,632,631 B1 | 10/2003 | Shuster et al. |
| 6,699,696 B2 | 3/2004 | Woods et al. |
| 7,026,527 B2 | 4/2006 | Falco et al. |
| 7,122,331 B1 | 10/2006 | Eisenreich et al. |
| 8,048,654 B2 | 11/2011 | Berry et al. |
| 2005/0014241 A1 | 1/2005 | Chen |
| 2005/0124010 A1 | 6/2005 | Short et al. |
| 2005/0239179 A1 | 10/2005 | Skraly et al. |
| 2011/0020883 A1 | 1/2011 | Roessler et al. |

FOREIGN PATENT DOCUMENTS

| WO | WO 2007/084477 | 1/2007 |
|---|---|---|
| WO | WO 2007/136762 | 11/2007 |
| WO | WO 2007/139925 | 12/2007 |
| WO | WO 2008/119082 | 10/2008 |
| WO | WO 2009/009391 | 1/2009 |
| WO | WO 2009/062190 | 5/2009 |
| WO | WO 2009/076559 | 6/2009 |
| WO | WO 2009/111513 | 9/2009 |
| WO | WO 2010/019813 | 2/2010 |
| WO | WO 2010/021711 | 2/2010 |
| WO | WO 2010/022090 | 2/2010 |
| WO | WO 2010/033921 | 3/2010 |
| WO | WO 2010/044960 | 4/2010 |

OTHER PUBLICATIONS

European Patent Office, Search Report and Opinion, European Patent Application No. 13195355.6, Feb. 3, 2014, five pages.
Kaku, N. et al., "Effects of overexpression of *Escherichia coli katE* and *bet* genes on the tolerance for salt stress in a freshwater cyanobacterium *Synechocuccus* sp. PCC 7942," *Plant Science*, 2000, pp. 281-288, vol. 159.
State Intellectual Property Office of the People's Republic of China, Third Office Action, Chinese Patent Application No. 200980114073. 0, Apr. 15, 2014, six pages.
State Intellectual Property Office of the People's Republic of China, Second Office Action, Chinese Patent Application No. 200980114073.0, Aug. 15, 2013, seven pages.

(Continued)

Primary Examiner — Tekchand Saidha
(74) Attorney, Agent, or Firm — Fenwick & West LLP; Chang B. Hong, Esq.

(57) ABSTRACT

The present disclosure identifies methods and compositions for modifying photoautotrophic organisms, such that the organisms efficiently convert carbon dioxide and light into compounds such as esters and fatty acids. In certain embodiments, the compounds produced are secreted into the medium used to culture the organisms.

20 Claims, 5 Drawing Sheets

(56) References Cited

OTHER PUBLICATIONS

Cho, H. et al., "Defective Export of a Periplasmic Enzyme Disrupts Regulation of Fatty Acid Synthesis," *The Journal of Biological Chemistry*, 1995, pp. 4216-4219, vol. 270, No. 9.

Cho, H. et al., "*Escherichia coli* Thioesterase I, Molecular Cloning and Sequencing of the Structural Gene and Identification as a Periplasmic Enzyme," *The Journal of Biological Chemistry*, May 5, 1993, vol. 268, pp. 9238-9245, No. 13.

Chollet, R. et al., "The AcrAB-ToIC Pump Is Involved in Macrolide Resistance but Not in Telithromycin Efflux in *Enterobacter aerogenes* and *Escherichia coli*," *Antimicrobial Agents and Chemotherapy*, Sep. 2004, pp. 3621-3624, vol. 48.

Cohen, N. et al., "Functional Expression of Rat GLUT 1 Glucose Transporter in *Dictyostelium discoideum*," *Biochem. J.*, 1996, pp. 971-975, vol. 315.

Deng, M. et al., "Ethanol Synthesis by Genetic Engineering in Cyanobacteria," *Applied and Environmental Microbiology*, Feb. 1999, pp. 523-528, vol. 65, No. 2.

European Patent Office, Examination Report, European Patent Application No. 09717082.3, Feb. 14, 2013, four pages.

European Patent Office, Examination Report, European Patent Application No. 09820965.3, Feb. 18, 2013, five pages.

European Patent Office, Supplementary Search Report and Opinion, European Patent Application No. 09820965.3, Feb. 22, 2012, seven pages.

Frigaard, N-U. et al., "Gene Inactivation in the Cyanobacterium *Synechococcus* sp. PCC 7002 and the Green Sulfur Bacterium *Chlorobium tepidum* Using in Vitro-made DNA Constructs and Natural Transformation," *Methods in Molecular Biology*, 2004, pp. 325-340, vol. 274.

Genin, S. et al., "*Ralstonia solanacearum*: Secrets of a Major Pathogen Unveiled by Analysis of Its Genome," *Molecular Plant Pathology*, 2002, pp. 111-118, vol. 3, No. 3.

Ho, N. et al., "Genetically Engineered *Saccharomyces* Yeast Capable of Effective Cofermentation of Glucose and Xylose," Applied and Environmental Microbiology, 1998, pp. 1852-1859, vol. 64, No. 5.

Inokuma, K. et al., "Characterization of Enzymes Involved in the Ethanol Production of *Moorella* sp. HUC22-1," Archives of Microbiology, 2007, pp. 37-45, vol. 188.

Iwai, M. et al., "Improved Genetic Transformation of the Thermophilic Cyanobacterium, *Thermosynechococcus elongatus* BP-1," *Plant and Cell Physiology*, 2004, pp. 171-175, vol. 45, No. 2.

Kalscheuer, R. et al., "A Novel Bifunctional Wax Ester Synthase/Acyl-CoA:Diacyglycerol Acyltransferase Mediates Wax Ester and Triacylglycerol Biosynthesis in *Acinetobacter calcoaceticus* ADP1," *Journal of Biological Chemistry*, 2003, pp. 8075-8082, vol. 278, No. 10.

Kalscheuer, R. et al., "Microdiesel: *Escherichia coli* Engineered for Fuel Production," *Microbiology*, 2006, pp. 2529-2536, vol. 152.

Kalscheuer, R. et al., "Neutral Lipid Biosynthesis in Engineered *Escherichia coli*: Jojoba Oil-Like Wax Esters and Fatty Acid Butyl Esters," *Applied and Environmental Microbiology*, Feb. 2006, pp. 1373-1379, vol. 72, No. 2.

Kameda, K. et al., "Purification and Characterization of Acyl Coenzyme A Synthetase from *Escherichia coli*," *The Journal of Biological Chemistry*, 1981, pp. 5702-5707, vol. 256.

Kimura, A. et al., "A High temperature-Sensitive Mutant of *Synechococcus* sp. PCC 7002 with Modifications in the Endogenous Plasmid, pAQ1," *Plant and Cell Physiology*, 2002, vol. 43, No. 2, pp. 217-223 (abstract only) [Online] [Retrieved Nov. 28, 2009] Retrieved from the internet <URL:http://pcp.oxfordjournals.org/cgi/content/abstract/43/2/217>.

Liu, X. et al., "Production and Secretion of Fatty Acids in Genetically Engineered Cyanobacteria," *Proceedings of the National Academy of Sciences USA Early Edition*, Mar. 29, 2010, six pages. [Online] Retrieved from the Internet <URL:http://www.pnas.org/content/early/2010/07/01/1001946107.full.pdf.>.

Liu, X. et al., "Supporting Information: SI Materials and Methods. Growth of an SD Culture Started from a Single Cell Descended Colony," *Proceedings of the National Academy of Sciences USA*, 2010, ten pages. [Online] Retrieved from the Internet: <URL:http://www.pnas.org/content/suppl/2010/03/26/1001946107.DCSupplemental/pnas.1001946107_SI.pdf.>.

Lloyd, A. et al., "Topology of the *Escherichia coli* uhpT Sugar-Phosphate Transporter Analyzed by Using TnphoA Fusions," *Journal of Bacteriology*, Apr. 1990, pp. 1688-1693, vol. 172, No. 4.

Lopez-Maury, L., "A Two-component Signal Transduction System Involved in Nickel Sensing in the Cyanobacterium *Synechocystis* sp. PCC 6803," *Molecular Microbiology*, 2002, pp. 247-256, vol. 43, No. 1.

Marrakchi, H. et al., "Mechanistic Diversity and Regulation of Type II Fatty Acid Synthesis," *Biochemical Society Transactions*, 2002, pp. 1050-1055, vol. 30.

Nielsen, D.R. et al., "Engineering Alternative Butanol Production Platforms in Heterologous Bacteria," *Metabolic Engineering*, Jul. 2009, pp. 262-273, vol. 11.

PCT International Search Report and Written Opinion, PCT Application No. PCT/US2009/035937, Aug. 3, 2009, fifteen pages.

PCT International Search Report and Written Opinion, PCT Application No. PCT/US2009/055949, Mar. 15, 2010, seven pages.

Qi, Q. et al.,"Application of the *Synechococcus* nirA Promoter to Establish an Inducible Expression System for Engineering the Synechocystis Tocopherol Pathway," *Applied and Environmental Microbiology*, Oct. 2005, pp. 5678-5684, vol. 71, No. 10.

Rock, C. et al., "Increased Unsaturated Fatty Acid Production Associated with a Suppressor of the *fabA6*(Ts) Mutation in *Escherichia coli*," *Journal of Bacteriology*, 1996, pp. 5382-5387, vol. 178, No. 18.

State Intellectual Property Office of the People's Republic of China, First Office Action, Chinese Patent Application No. 200980114073.0, Dec. 5, 2012, fourteen pages.

Steen, E. et al., "Microbial Production of Fatty-acid-derived Fuels and Chemicals from Plant Biomass," *Nature*, Jan. 28, 2010, pp. 559-562, vol. 463.

Stoveken, T. et al., "The Wax Ester Synthase/Acyl Coenzyme A:Diacylglycerol Acyltransferase from *Acinetobacter* sp. Strain ADP1: Characterization of a Novel Type of Acyltransferase," *Journal of Bacteriology*, Feb. 2005, pp. 1369-1376, vol. 187, No. 4.

Tsukagoshi, N. et al., "Entry into and Release of Solvents by *Escherichia coli* in an Organic-Aqueous Two-Liquid-Phase System and Substrate Specificity of the AcrAB-ToIC Solvent-Extruding Pump," *Journal of Bacteriology*, Sep. 2000, pp. 4803-4810, vol. 182, No. 17.

Weisser, P. et al., "Functional Expression of the Glucose Transporter of *Zymomonas mobilis* Leads to Restoration of Glucose and Fructose Uptake in *Escherichia coli* Mutants and Provides Evidence for Its Facilitator Action," *Journal of Bacteriology*, Jun. 1995, pp. 3351-3354, vol. 177, No. 11.

European Patent Office, Examination Report, European Patent Application No. 09820965.3, May 22, 2014, six pages.

Bernroitner, M. et al., "Occurrence, phylogeny, structure, and function of catalases and peroxidases in cyanobacteria," Journal of Experimental Botany, 2009, pp. 423-440, vol. 60, No. 2.

United States Office Action, U.S. Appl. No. 13/349,545, Aug. 15, 2014, seven pages.

SEQUENCE LISTING

<160> NUMBER OF SEQ ID NOS: 25

<210> SEQ ID NO 1
<211> LENGTH: 183
<212> TYPE: PRT
<213> ORGANISM: Escherichia coli

<400> SEQUENCE: 1

```
Met Ala Asp Thr Leu Leu Ile Leu Gly Asp Ser Leu Ser Ala Gly Tyr
1               5                   10                  15

Arg Met Ser Ala Ser Ala Ala Trp Pro Ala Leu Leu Asn Asp Lys Trp
            20                  25                  30

Gln Ser Lys Thr Ser Val Val Asn Ala Ser Ile Ser Gly Asp Thr Ser
        35                  40                  45

Gln Gln Gly Leu Ala Arg Leu Pro Ala Leu Leu Lys Gln His Gln Pro
    50                  55                  60

Arg Trp Val Leu Val Glu Leu Gly Gly Asn Asp Gly Leu Arg Gly Phe
65                  70                  75                  80

Gln Pro Gln Gln Thr Glu Gln Thr Leu Arg Gln Ile Leu Gln Asp Val
                85                  90                  95

Lys Ala Ala Asn Ala Glu Pro Leu Leu Met Gln Ile Arg Leu Pro Ala
            100                 105                 110

Asn Tyr Gly Arg Arg Tyr Asn Glu Ala Phe Ser Ala Ile Tyr Pro Lys
        115                 120                 125

Leu Ala Lys Glu Phe Asp Val Pro Leu Leu Pro Phe Phe Met Glu Glu
```

```
            130                 135                 140
Val Tyr Leu Lys Pro Gln Trp Met Gln Asp Asp Gly Ile His Pro Asn
145                 150                 155                 160

Arg Asp Ala Gln Pro Phe Ile Ala Asp Trp Met Ala Lys Gln Leu Gln
                165                 170                 175

Pro Leu Val Asn His Asp Ser
            180

<210> SEQ ID NO 2
<211> LENGTH: 561
<212> TYPE: PRT
<213> ORGANISM: Escherichia coli

<400> SEQUENCE: 2

Met Lys Lys Val Trp Leu Asn Arg Tyr Pro Ala Asp Val Pro Thr Glu
1               5                   10                  15

Ile Asn Pro Asp Arg Tyr Gln Ser Leu Val Asp Met Phe Glu Gln Ser
                20                  25                  30

Val Ala Arg Tyr Ala Asp Gln Pro Ala Phe Val Asn Met Gly Glu Val
            35                  40                  45

Met Thr Phe Arg Lys Leu Glu Glu Arg Ser Arg Ala Phe Ala Ala Tyr
50                  55                  60

Leu Gln Gln Gly Leu Gly Leu Lys Lys Gly Asp Arg Val Ala Leu Met
65                  70                  75                  80

Met Pro Asn Leu Leu Gln Tyr Pro Val Ala Leu Phe Gly Ile Leu Arg
                85                  90                  95

Ala Gly Met Ile Val Val Asn Val Asn Pro Leu Tyr Thr Pro Arg Glu
            100                 105                 110

Leu Glu His Gln Leu Asn Asp Ser Gly Ala Ser Ala Ile Val Ile Val
        115                 120                 125

Ser Asn Phe Ala His Thr Leu Glu Lys Val Val Asp Lys Thr Ala Val
130                 135                 140

Gln His Val Ile Leu Thr Arg Met Gly Asp Gln Leu Ser Thr Ala Lys
145                 150                 155                 160

Gly Thr Val Val Asn Phe Val Val Lys Tyr Ile Lys Arg Leu Val Pro
                165                 170                 175

Lys Tyr His Leu Pro Asp Ala Ile Ser Phe Arg Ser Ala Leu His Asn
            180                 185                 190

Gly Tyr Arg Met Gln Tyr Val Lys Pro Glu Leu Val Pro Glu Asp Leu
        195                 200                 205

Ala Phe Leu Gln Tyr Thr Gly Gly Thr Thr Gly Val Ala Lys Gly Ala
    210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
                245                 250                 255

Leu Pro Leu Tyr His Ile Phe Ala Leu Thr Ile Asn Cys Leu Leu Phe
            260                 265                 270

Ile Glu Leu Gly Gly Gln Asn Leu Leu Ile Thr Asn Pro Arg Asp Ile
        275                 280                 285

Pro Gly Leu Val Lys Glu Leu Ala Lys Tyr Pro Phe Thr Ala Ile Thr
    290                 295                 300

Gly Val Asn Thr Leu Phe Asn Ala Leu Leu Asn Asn Lys Glu Phe Gln
305                 310                 315                 320
```

```
Gln Leu Asp Phe Ser Ser Leu His Leu Ser Ala Gly Gly Gly Met Pro
                325                 330                 335

Val Gln Gln Val Val Ala Glu Arg Trp Val Lys Leu Thr Gly Gln Tyr
            340                 345                 350

Leu Leu Glu Gly Tyr Gly Leu Thr Glu Cys Ala Pro Leu Val Ser Val
        355                 360                 365

Asn Pro Tyr Asp Ile Asp Tyr His Ser Gly Ser Ile Gly Leu Pro Val
370                 375                 380

Pro Ser Thr Glu Ala Lys Leu Val Asp Asp Asp Asn Glu Val Pro
385                 390                 395                 400

Pro Gly Gln Pro Gly Glu Leu Cys Val Lys Gly Pro Gln Val Met Leu
                405                 410                 415

Gly Tyr Trp Gln Arg Pro Asp Ala Thr Asp Glu Ile Ile Lys Asn Gly
            420                 425                 430

Trp Leu His Thr Gly Asp Ile Ala Val Met Asp Glu Glu Gly Phe Leu
        435                 440                 445

Arg Ile Val Asp Arg Lys Lys Asp Met Ile Leu Val Ser Gly Phe Asn
    450                 455                 460

Val Tyr Pro Asn Glu Ile Glu Asp Val Val Met Gln His Pro Gly Val
465                 470                 475                 480

Gln Glu Val Ala Ala Val Gly Val Pro Ser Gly Ser Ser Gly Glu Ala
                485                 490                 495

Val Lys Ile Phe Val Val Lys Lys Asp Pro Ser Leu Thr Glu Glu Ser
            500                 505                 510

Leu Val Thr Phe Cys Arg Arg Gln Leu Thr Gly Tyr Lys Val Pro Lys
        515                 520                 525

Leu Val Glu Phe Arg Asp Glu Leu Pro Lys Ser Asn Val Gly Lys Ile
    530                 535                 540

Leu Arg Arg Glu Leu Arg Asp Glu Ala Arg Gly Lys Val Asp Asn Lys
545                 550                 555                 560

Ala

<210> SEQ ID NO 3
<211> LENGTH: 458
<212> TYPE: PRT
<213> ORGANISM: Acinetobacter baylyi

<400> SEQUENCE: 3

Met Arg Pro Leu His Pro Ile Asp Phe Ile Phe Leu Ser Leu Glu Lys
1               5                   10                  15

Arg Gln Gln Pro Met His Val Gly Gly Leu Phe Leu Phe Gln Ile Pro
                20                  25                  30

Asp Asn Ala Pro Asp Thr Phe Ile Gln Asp Leu Val Asn Asp Ile Arg
            35                  40                  45

Ile Ser Lys Ser Ile Pro Val Pro Pro Phe Asn Asn Lys Leu Asn Gly
        50                  55                  60

Leu Phe Trp Asp Glu Asp Glu Glu Phe Asp Leu Asp His His Phe Arg
65                  70                  75                  80

His Ile Ala Leu Pro His Pro Gly Arg Ile Arg Glu Leu Leu Ile Tyr
                85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
        115                 120                 125
```

-continued

```
Phe Lys Ile His His Ala Met Val Asp Gly Val Ala Gly Met Arg Leu
    130                 135                 140
Ile Glu Lys Ser Leu Ser His Asp Val Thr Glu Lys Ser Ile Val Pro
145                 150                 155                 160
Pro Trp Cys Val Glu Gly Lys Arg Ala Lys Arg Leu Arg Glu Pro Lys
                165                 170                 175
Thr Gly Lys Ile Lys Lys Ile Met Ser Gly Ile Lys Ser Gln Leu Gln
            180                 185                 190
Ala Thr Pro Thr Val Ile Gln Glu Leu Ser Gln Thr Val Phe Lys Asp
        195                 200                 205
Ile Gly Arg Asn Pro Asp His Val Ser Ser Phe Gln Ala Pro Cys Ser
    210                 215                 220
Ile Leu Asn Gln Arg Val Ser Ser Arg Arg Phe Ala Ala Gln Ser
225                 230                 235                 240
Phe Asp Leu Asp Arg Phe Arg Asn Ile Ala Lys Ser Leu Asn Val Thr
                245                 250                 255
Ile Asn Asp Val Val Leu Ala Val Cys Ser Gly Ala Leu Arg Ala Tyr
            260                 265                 270
Leu Met Ser His Asn Ser Leu Pro Ser Lys Pro Leu Ile Ala Met Val
        275                 280                 285
Pro Ala Ser Ile Arg Asn Asp Asp Ser Asp Val Ser Asn Arg Ile Thr
    290                 295                 300
Met Ile Leu Ala Asn Leu Ala Thr His Lys Asp Asp Pro Leu Gln Arg
305                 310                 315                 320
Leu Glu Ile Ile Arg Arg Ser Val Gln Asn Ser Lys Gln Arg Phe Lys
                325                 330                 335
Arg Met Thr Ser Asp Gln Ile Leu Asn Tyr Ser Ala Val Val Tyr Gly
            340                 345                 350
Pro Ala Gly Leu Asn Ile Ile Ser Gly Met Met Pro Lys Arg Gln Ala
        355                 360                 365
Phe Asn Leu Val Ile Ser Asn Val Pro Gly Pro Arg Glu Pro Leu Tyr
    370                 375                 380
Trp Asn Gly Ala Lys Leu Asp Ala Leu Tyr Pro Ala Ser Ile Val Leu
385                 390                 395                 400
Asp Gly Gln Ala Leu Asn Ile Thr Met Thr Ser Tyr Leu Asp Lys Leu
                405                 410                 415
Glu Val Gly Leu Ile Ala Cys Arg Asn Ala Leu Pro Arg Met Gln Asn
            420                 425                 430
Leu Leu Thr His Leu Glu Glu Glu Ile Gln Leu Phe Glu Gly Val Ile
        435                 440                 445
Ala Lys Gln Glu Asp Ile Lys Thr Ala Asn
    450                 455
```

<210> SEQ ID NO 4
<211> LENGTH: 552
<212> TYPE: DNA
<213> ORGANISM: Escherichia coli

<400> SEQUENCE: 4

```
atggcggata ctctgctgat tctgggtgat tctctgtctg caggctaccg tatgtccgcc     60
tccgcggcct ggccagctct gctgaatgat aagtggcagt ctaagacgtc cgttgtgaac    120
gcatccatct ctggcgacac gagccagcag ggcctggccc gtctgcctgc actgctgaaa    180
cagcaccaac cgcgctgggt cctggtggag ctgggcggta cgacggtct gcgcggcttc    240
```

| | |
|---|---|
| cagccgcagc agaccgaaca gactctgcgt cagattctgc aggacgtgaa agctgctaac | 300 |
| gcggaaccgc tgctgatgca gattcgtctg ccagcgaact atggccgccg ttacaacgaa | 360 |
| gcgttctctg caatctaccc aaaactggcg aaagagtttg acgtcccgct gctgccgttc | 420 |
| ttcatggagg aagtatacct gaaaccgcag tggatgcaag atgacggcat ccacccgaac | 480 |
| cgtgatgcgc agccgttcat cgctgactgg atggcgaagc aactgcagcc gctggtaaac | 540 |
| cacgattcct aa | 552 |

<210> SEQ ID NO 5
<211> LENGTH: 1686
<212> TYPE: DNA
<213> ORGANISM: Escherichia coli

<400> SEQUENCE: 5

| | |
|---|---|
| atgaagaaag tttggctgaa ccgttatccg gcagatgtac cgactgaaat taacccagat | 60 |
| cgttaccagt ccctggttga catgttcgaa cagtccgtgg ctcgctacgc cgatcagcct | 120 |
| gctttcgtca acatgggtga ggtaatgacc tttcgcaaac tggaggagcg ttcccgtgct | 180 |
| ttcgcggcat acctgcagca gggtctgggc ctgaagaaag cgaccgcgt ggccctgatg | 240 |
| atgccgaacc tgctgcaata tcctgtgcg ctgttcggta tcctgcgtgc tggtatgatc | 300 |
| gttgtcaatg ttaaccctct gtataccct cgtgaactgg agcaccagct gaatgactct | 360 |
| ggtgcgtctg ctatcgttat cgtttccaat ttcgcacata cgctggagaa agtggttgat | 420 |
| aaaaccgcag tgcagcatgt cattctgact cgcatgggtg accagctgtc caccgctaaa | 480 |
| ggtactgtag tcaacttcgt tgtgaaatac attaagcgcc tggttccgaa ataccacctg | 540 |
| ccagatgcaa ttagctttcg ctctgcactg cataacggtt accgtatgca gtacgtaaaa | 600 |
| ccagagctgt tgccggaaga cctggccttt ctgcagtata ccggcggcac caccggcgtg | 660 |
| gcaaagggcg cgatgctgac ccatcgtaac atgctggcga acctggagca ggttaacgca | 720 |
| acgtacggcc cgctgctgca cccgggtaaa gaactggtag ttacggcact gcctctgtat | 780 |
| cacatctttg cactgacgat caactgtctg ctgttcattg aactgggtgg tcagaacctg | 840 |
| ctgatcacca cccgcgtga cattccgggc ctggtaaaag agctggctaa gtacccgttc | 900 |
| accgccatta ctggcgtaaa cactctgttt aacgcgctgc tgaacaacaa agagtttcag | 960 |
| cagctggact ctctctagcct gcacctgagc gctggcggtg gcatgccggt tcagcaggtt | 1020 |
| gtggcagagc gttgggtgaa actgaccggc cagtatctgc tggagggtta tggtctgacc | 1080 |
| gagtgtgcac cgctggtcag cgttaacccg tatgatattg attaccactc tggttctatt | 1140 |
| ggtctgccgg ttccgtccac ggaagccaaa ctggtggacg atgacgacaa cgaagtacct | 1200 |
| ccgggccagc cgggtgagct gtgtgtcaag ggtccgcagg ttatgctggg ctactggcag | 1260 |
| cgccccggacg ccaccgacga aatcattaaa aacggttggc tgcataccgg tgatatcgct | 1320 |
| gtaatggacg aagaaggttt cctgcgtatc gtggaccgta agaaagatat gattctggtg | 1380 |
| agcggtttca acgtgtaccc gaacgaaatt gaggactag ttatgcaaca ccctggcgtg | 1440 |
| caggaggtgg cagccgtggg cgtgccgtcc ggttcttctg gtgaggctgt gaaaatcttt | 1500 |
| gtcgttaaaa aggacccgtc cctgaccgaa gaatctctgg tgacgtttg ccgccgtcaa | 1560 |
| ctgactggct acaaagtgcc gaaactggtc gagttccgcg atgagctgcc aaaatctaac | 1620 |
| gtgggtaaga tcctgcgccg cgagctgcgt gacgaggcac gtggcaaagt tgacaataaa | 1680 |
| gcataa | 1686 |

<210> SEQ ID NO 6
<211> LENGTH: 1377
<212> TYPE: DNA
<213> ORGANISM: Acinetobacter baylyi

<400> SEQUENCE: 6

```
atgcgcccac ttcatccgat cgatttcatt ttcctgtccc tggagaaacg ccagcagccg      60
atgcacgtag gtggtctgtt cctgttccag atcccggata cgctccgga caccttttatt     120
caggacctgg tgaacgatat ccgtatctcc aagtctattc cggttccgcc gttcaacaac     180
aagctgaacg gtctgttctg ggacgaagac gaggagttcg atctggatca ccatttccgt     240
catattgcgc tgccgcaccc gggtcgcatc cgtgagctgc tgatttacat ctctcaggaa     300
cacagcactc tcctcgatcg cgctaaacct ctgtggactt gcaacatcat gaaggtatc      360
gagggtaacc gttcgccat gtacttcaag attcatcatg cgatggtgga tggtgtggcg      420
ggtatgcgtc tgattgagaa aagcctgtcc catgatgtta ctgaaaagag catcgtaccg     480
ccgtggtgcg ttgagggcaa acgtgctaaa cgcctgcgtg aaccgaagac cggcaaaatt     540
aagaaaatca tgtctggtat taaatctcag ctccaggcca ccccgaccgt tattcaagaa     600
ctgtctcaga cggtcttcaa agacatcggc cgtaatccgg accacgtttc ctcttttccag    660
gcgccgtgct ccatcctcaa ccagcgtgtg tcttcttctc gtcgtttcgc agcacagagc     720
tttgacctgg accgtttccg caacatcgcc aaatctctga acgtgaccat taacgacgtt     780
gtcctggctg tgtgtagcgg tgctctgcgc gcttatctga tgtctcataa ctctctgcca     840
tccaaaccgc tgatcgctat ggtcccagca agcatccgca acgatgattc tgatgtgtcc     900
aaccgtatta ctatgattct ggccaacctc gctactcaca aagacgaccc tctgcagcgt     960
ctggaaatca tccgccgctc cgtccagaac tctaaacagc gttttaaacg catgacttcc    1020
gaccagattc tgaactattc tgcggttgta tacggcccgg ctggtctgaa cattatcagc    1080
ggtatgatgc cgaaacgtca ggcttttaac ctggtaatca gcaacgttcc tggcccgcgt    1140
gagccgctgt actggaacgg cgcaaaactg gacgcactgt acccggcttc catcgttctg    1200
gatggccagg ctctgaacat cactatgacc tcttacctgg acaaactgga agtaggtctg    1260
atcgcgtgtc gcaatgcact gccgcgcatg cagaacctgc tgacccacct ggaggaggaa    1320
atccagctgt tgagggcgt tatcgccaaa caggaagata tcaaaacggc gaactaa       1377
```

<210> SEQ ID NO 7
<211> LENGTH: 493
<212> TYPE: PRT
<213> ORGANISM: Escherichia coli

<400> SEQUENCE: 7

```
Met Lys Lys Leu Leu Pro Ile Leu Ile Gly Leu Ser Leu Ser Gly Phe
 1               5                  10                  15

Ser Ser Leu Ser Gln Ala Glu Asn Leu Met Gln Val Tyr Gln Gln Ala
            20                  25                  30

Arg Leu Ser Asn Pro Glu Leu Arg Lys Ser Ala Ala Asp Arg Asp Ala
        35                  40                  45

Ala Phe Glu Lys Ile Asn Glu Ala Arg Ser Pro Leu Leu Pro Gln Leu
    50                  55                  60

Gly Leu Gly Ala Asp Tyr Thr Tyr Ser Asn Gly Tyr Arg Asp Ala Asn
65                  70                  75                  80

Gly Ile Asn Ser Asn Ala Thr Ser Ala Ser Leu Gln Leu Thr Gln Ser
                85                  90                  95
```

Ile Phe Asp Met Ser Lys Trp Arg Ala Leu Thr Leu Gln Glu Lys Ala
100                 105                 110

Ala Gly Ile Gln Asp Val Thr Tyr Gln Thr Asp Gln Gln Thr Leu Ile
    115                 120                 125

Leu Asn Thr Ala Thr Ala Tyr Phe Asn Val Leu Asn Ala Ile Asp Val
130                 135                 140

Leu Ser Tyr Thr Gln Ala Gln Lys Glu Ala Ile Tyr Arg Gln Leu Asp
145                 150                 155                 160

Gln Thr Thr Gln Arg Phe Asn Val Gly Leu Val Ala Ile Thr Asp Val
                165                 170                 175

Gln Asn Ala Arg Ala Gln Tyr Asp Thr Val Leu Ala Asn Glu Val Thr
            180                 185                 190

Ala Arg Asn Asn Leu Asp Asn Ala Val Glu Gln Leu Arg Gln Ile Thr
        195                 200                 205

Gly Asn Tyr Tyr Pro Glu Leu Ala Ala Leu Asn Val Glu Asn Phe Lys
    210                 215                 220

Thr Asp Lys Pro Gln Pro Val Asn Ala Leu Leu Lys Glu Ala Glu Lys
225                 230                 235                 240

Arg Asn Leu Ser Leu Leu Gln Ala Arg Leu Ser Gln Asp Leu Ala Arg
                245                 250                 255

Glu Gln Ile Arg Gln Ala Gln Asp Gly His Leu Pro Thr Leu Asp Leu
            260                 265                 270

Thr Ala Ser Thr Gly Ile Ser Asp Thr Ser Tyr Ser Gly Ser Lys Thr
        275                 280                 285

Arg Gly Ala Ala Gly Thr Gln Tyr Asp Asp Ser Asn Met Gly Gln Asn
    290                 295                 300

Lys Val Gly Leu Ser Phe Ser Leu Pro Ile Tyr Gln Gly Gly Met Val
305                 310                 315                 320

Asn Ser Gln Val Lys Gln Ala Gln Tyr Asn Phe Val Gly Ala Ser Glu
                325                 330                 335

Gln Leu Glu Ser Ala His Arg Ser Val Val Gln Thr Val Arg Ser Ser
            340                 345                 350

Phe Asn Asn Ile Asn Ala Ser Ile Ser Ser Ile Asn Ala Tyr Lys Gln
        355                 360                 365

Ala Val Val Ser Ala Gln Ser Ser Leu Asp Ala Met Glu Ala Gly Tyr
    370                 375                 380

Ser Val Gly Thr Arg Thr Ile Val Asp Val Leu Asp Ala Thr Thr Thr
385                 390                 395                 400

Leu Tyr Asn Ala Lys Gln Glu Leu Ala Asn Ala Arg Tyr Asn Tyr Leu
                405                 410                 415

Ile Asn Gln Leu Asn Ile Lys Ser Ala Leu Gly Thr Leu Asn Glu Gln
            420                 425                 430

Asp Leu Leu Ala Leu Asn Asn Ala Leu Ser Lys Pro Val Ser Thr Asn
        435                 440                 445

Pro Glu Asn Val Ala Pro Gln Thr Pro Glu Gln Asn Ala Ile Ala Asp
    450                 455                 460

Gly Tyr Ala Pro Asp Ser Pro Ala Pro Val Val Gln Gln Thr Ser Ala
465                 470                 475                 480

Arg Thr Thr Thr Ser Asn Gly His Asn Pro Phe Arg Asn
                485                 490

<210> SEQ ID NO 8
<211> LENGTH: 397
<212> TYPE: PRT

<213> ORGANISM: Escherichia coli

<400> SEQUENCE: 8

```
Met Asn Lys Asn Arg Gly Phe Thr Pro Leu Ala Val Val Leu Met Leu
1               5                   10                  15
Ser Gly Ser Leu Ala Leu Thr Gly Cys Asp Asp Lys Gln Ala Gln Gln
            20                  25                  30
Gly Gly Gln Gln Met Pro Ala Val Gly Val Val Thr Val Lys Thr Glu
        35                  40                  45
Pro Leu Gln Ile Thr Thr Glu Leu Pro Gly Arg Thr Ser Ala Tyr Arg
    50                  55                  60
Ile Ala Glu Val Arg Pro Gln Val Ser Gly Ile Ile Leu Lys Arg Asn
65                  70                  75                  80
Phe Lys Glu Gly Ser Asp Ile Glu Ala Gly Val Ser Leu Tyr Gln Ile
                85                  90                  95
Asp Pro Ala Thr Tyr Gln Ala Thr Tyr Asp Ser Ala Lys Gly Asp Leu
            100                 105                 110
Ala Lys Ala Gln Ala Ala Ala Asn Ile Ala Gln Leu Thr Val Asn Arg
        115                 120                 125
Tyr Gln Lys Leu Leu Gly Thr Gln Tyr Ile Ser Lys Gln Glu Tyr Asp
    130                 135                 140
Gln Ala Leu Ala Asp Ala Gln Gln Ala Asn Ala Ala Val Thr Ala Ala
145                 150                 155                 160
Lys Ala Ala Val Glu Thr Ala Arg Ile Asn Leu Ala Tyr Thr Lys Val
                165                 170                 175
Thr Ser Pro Ile Ser Gly Arg Ile Gly Lys Ser Asn Val Thr Glu Gly
            180                 185                 190
Ala Leu Val Gln Asn Gly Gln Ala Thr Ala Leu Ala Thr Val Gln Gln
        195                 200                 205
Leu Asp Pro Ile Tyr Val Asp Val Thr Gln Ser Ser Asn Asp Phe Leu
    210                 215                 220
Arg Leu Lys Gln Glu Leu Ala Asn Gly Thr Leu Lys Gln Glu Asn Gly
225                 230                 235                 240
Lys Ala Lys Val Ser Leu Ile Thr Ser Asp Gly Ile Lys Phe Pro Gln
                245                 250                 255
Asp Gly Thr Leu Glu Phe Ser Asp Val Thr Val Asp Gln Thr Thr Gly
            260                 265                 270
Ser Ile Thr Leu Arg Ala Ile Phe Pro Asn Pro Asp His Thr Leu Leu
    275                 280                 285
Pro Gly Met Phe Val Arg Ala Arg Leu Glu Glu Gly Leu Asn Pro Asn
290                 295                 300
Ala Ile Leu Val Pro Gln Gln Gly Val Thr Arg Thr Pro Arg Gly Asp
305                 310                 315                 320
Ala Thr Val Leu Val Val Gly Ala Asp Asp Lys Val Glu Thr Arg Pro
                325                 330                 335
Ile Val Ala Ser Gln Ala Ile Gly Asp Lys Trp Leu Val Thr Glu Gly
            340                 345                 350
Leu Lys Ala Gly Asp Arg Val Val Ile Ser Gly Leu Gln Lys Val Arg
        355                 360                 365
Pro Gly Val Gln Val Lys Ala Gln Glu Val Thr Ala Asp Asn Asn Gln
    370                 375                 380
Gln Ala Ser Gly Ala Gln Pro Glu Gln Ser Lys Ser
385                 390                 395
```

```
<210> SEQ ID NO 9
<211> LENGTH: 1049
<212> TYPE: PRT
<213> ORGANISM: Escherichia coli

<400> SEQUENCE: 9

Met Pro Asn Phe Phe Ile Asp Arg Pro Ile Phe Ala Trp Val Ile Ala
1               5                   10                  15

Ile Ile Ile Met Leu Ala Gly Gly Leu Ala Ile Leu Lys Leu Pro Val
            20                  25                  30

Ala Gln Tyr Pro Thr Ile Ala Pro Pro Ala Val Thr Ile Ser Ala Ser
        35                  40                  45

Tyr Pro Gly Ala Asp Ala Lys Thr Val Gln Asp Thr Val Thr Gln Val
    50                  55                  60

Ile Glu Gln Asn Met Asn Gly Ile Asp Asn Leu Met Tyr Met Ser Ser
65                  70                  75                  80

Asn Ser Asp Ser Thr Gly Thr Val Gln Ile Thr Leu Thr Phe Glu Ser
                85                  90                  95

Gly Thr Asp Ala Asp Ile Ala Gln Val Gln Val Gln Asn Lys Leu Gln
            100                 105                 110

Leu Ala Met Pro Leu Leu Pro Gln Glu Val Gln Gln Gly Val Ser
        115                 120                 125

Val Glu Lys Ser Ser Ser Ser Phe Leu Met Val Gly Val Ile Asn
130                 135                 140

Thr Asp Gly Thr Met Thr Gln Glu Asp Ile Ser Asp Tyr Val Ala Ala
145                 150                 155                 160

Asn Met Lys Asp Ala Ile Ser Arg Thr Ser Gly Val Gly Asp Val Gln
                165                 170                 175

Leu Phe Gly Ser Gln Tyr Ala Met Arg Ile Trp Met Asn Pro Asn Glu
            180                 185                 190

Leu Asn Lys Phe Gln Leu Thr Pro Val Asp Val Ile Thr Ala Ile Lys
        195                 200                 205

Ala Gln Asn Ala Gln Val Ala Ala Gly Gln Leu Gly Gly Thr Pro Pro
    210                 215                 220

Val Lys Gly Gln Gln Leu Asn Ala Ser Ile Ile Ala Gln Thr Arg Leu
225                 230                 235                 240

Thr Ser Thr Glu Glu Phe Gly Lys Ile Leu Leu Lys Val Asn Gln Asp
                245                 250                 255

Gly Ser Arg Val Leu Leu Arg Asp Val Ala Lys Ile Glu Leu Gly Gly
            260                 265                 270

Glu Asn Tyr Asp Ile Ile Ala Glu Phe Asn Gly Gln Pro Ala Ser Gly
        275                 280                 285

Leu Gly Ile Lys Leu Ala Thr Gly Ala Asn Ala Leu Asp Thr Ala Ala
    290                 295                 300

Ala Ile Arg Ala Glu Leu Ala Lys Met Glu Pro Phe Phe Pro Ser Gly
305                 310                 315                 320

Leu Lys Ile Val Tyr Pro Tyr Asp Thr Thr Pro Phe Val Lys Ile Ser
                325                 330                 335

Ile His Glu Val Val Lys Thr Leu Val Glu Ala Ile Ile Leu Val Phe
            340                 345                 350

Leu Val Met Tyr Leu Phe Leu Gln Asn Phe Arg Ala Thr Leu Ile Pro
        355                 360                 365

Thr Ile Ala Val Pro Val Val Leu Leu Gly Thr Phe Ala Val Leu Ala
    370                 375                 380
```

```
Ala Phe Gly Phe Ser Ile Asn Thr Leu Thr Met Phe Gly Met Val Leu
385                 390                 395                 400

Ala Ile Gly Leu Leu Val Asp Asp Ala Ile Val Val Glu Asn Val
                405                 410                 415

Glu Arg Val Met Ala Glu Glu Gly Leu Pro Pro Lys Glu Ala Thr Arg
                420                 425                 430

Lys Ser Met Gly Gln Ile Gln Gly Ala Leu Val Gly Ile Ala Met Val
                435                 440                 445

Leu Ser Ala Val Phe Val Pro Met Ala Phe Phe Gly Gly Ser Thr Gly
                450                 455                 460

Ala Ile Tyr Arg Gln Phe Ser Ile Thr Ile Val Ser Ala Met Ala Leu
465                 470                 475                 480

Ser Val Leu Val Ala Leu Ile Leu Thr Pro Ala Leu Cys Ala Thr Met
                485                 490                 495

Leu Lys Pro Ile Ala Lys Gly Asp His Gly Glu Gly Lys Lys Gly Phe
                500                 505                 510

Phe Gly Trp Phe Asn Arg Met Phe Glu Lys Ser Thr His His Tyr Thr
                515                 520                 525

Asp Ser Val Gly Gly Ile Leu Arg Ser Thr Gly Arg Tyr Leu Val Leu
                530                 535                 540

Tyr Leu Ile Ile Val Val Gly Met Ala Tyr Leu Phe Val Arg Leu Pro
545                 550                 555                 560

Ser Ser Phe Leu Pro Asp Glu Asp Gln Gly Val Phe Met Thr Met Val
                565                 570                 575

Gln Leu Pro Ala Gly Ala Thr Gln Glu Arg Thr Gln Lys Val Leu Asn
                580                 585                 590

Glu Val Thr His Tyr Tyr Leu Thr Lys Glu Lys Asn Asn Val Glu Ser
                595                 600                 605

Val Phe Ala Val Asn Gly Phe Gly Phe Ala Gly Arg Gly Gln Asn Thr
                610                 615                 620

Gly Ile Ala Phe Val Ser Leu Lys Asp Trp Ala Asp Arg Pro Gly Glu
625                 630                 635                 640

Glu Asn Lys Val Glu Ala Ile Thr Met Arg Ala Thr Arg Ala Phe Ser
                645                 650                 655

Gln Ile Lys Asp Ala Met Val Phe Ala Phe Asn Leu Pro Ala Ile Val
                660                 665                 670

Glu Leu Gly Thr Ala Thr Gly Phe Asp Phe Glu Leu Ile Asp Gln Ala
                675                 680                 685

Gly Leu Gly His Glu Lys Leu Thr Gln Ala Arg Asn Gln Leu Leu Ala
                690                 695                 700

Glu Ala Ala Lys His Pro Asp Met Leu Thr Ser Val Arg Pro Asn Gly
705                 710                 715                 720

Leu Glu Asp Thr Pro Gln Phe Lys Ile Asp Ile Asp Gln Glu Lys Ala
                725                 730                 735

Gln Ala Leu Gly Val Ser Ile Asn Asp Ile Asn Thr Thr Leu Gly Ala
                740                 745                 750

Ala Trp Gly Gly Ser Tyr Val Asn Asp Phe Ile Asp Arg Gly Arg Val
                755                 760                 765

Lys Lys Val Tyr Val Met Ser Glu Ala Lys Tyr Arg Met Leu Pro Asp
                770                 775                 780

Asp Ile Gly Asp Trp Tyr Val Arg Ala Ala Asp Gly Gln Met Val Pro
785                 790                 795                 800
```

-continued

Phe Ser Ala Phe Ser Ser Arg Trp Glu Tyr Gly Ser Pro Arg Leu
              805                 810                 815

Glu Arg Tyr Asn Gly Leu Pro Ser Met Glu Ile Leu Gly Gln Ala Ala
            820                 825                 830

Pro Gly Lys Ser Thr Gly Glu Ala Met Glu Leu Met Glu Gln Leu Ala
        835                 840                 845

Ser Lys Leu Pro Thr Gly Val Gly Tyr Asp Trp Thr Gly Met Ser Tyr
850                 855                 860

Gln Glu Arg Leu Ser Gly Asn Gln Ala Pro Ser Leu Tyr Ala Ile Ser
865                 870                 875                 880

Leu Ile Val Val Phe Leu Cys Leu Ala Ala Leu Tyr Glu Ser Trp Ser
                885                 890                 895

Ile Pro Phe Ser Val Met Leu Val Pro Leu Gly Val Ile Gly Ala
            900                 905                 910

Leu Leu Ala Ala Thr Phe Arg Gly Leu Thr Asn Asp Val Tyr Phe Gln
        915                 920                 925

Val Gly Leu Leu Thr Thr Ile Gly Leu Ser Ala Lys Asn Ala Ile Leu
    930                 935                 940

Ile Val Glu Phe Ala Lys Asp Leu Met Asp Lys Glu Gly Lys Gly Leu
945                 950                 955                 960

Ile Glu Ala Thr Leu Asp Ala Val Arg Met Arg Leu Arg Pro Ile Leu
                965                 970                 975

Met Thr Ser Leu Ala Phe Ile Leu Gly Val Met Pro Leu Val Ile Ser
            980                 985                 990

Thr Gly Ala Gly Ser Gly Ala Gln Asn Ala Val Gly Thr Gly Val Met
        995                 1000                1005

Gly Gly Met Val Thr Ala Thr Val Leu Ala Ile Phe Phe Val Pro
    1010                1015                1020

Val Phe Phe Val Val Arg Arg Arg Phe Ser Arg Lys Asn Glu
    1025                1030                1035

Asp Ile Glu His Ser His Thr Val Asp His His
    1040                1045

<210> SEQ ID NO 10
<211> LENGTH: 3821
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gcggccgcgg ggggggggg gaaagccacg ttgtgtctca aaatctctga tgttacattg      60
cacaagataa aaatatatca tcatgaacaa taaaactgtc tgcttacata acagtaata     120 caagggtcta tatggcggat actctgctga ttctgggtga ttctctgtct gcaggctacc    180
gtatgtccgc ctccgcggcc tggccagctc tgctgaatga taagtggcag tctaagacgt    240
ccgttgtgaa cgcatccatc tctggcgaca cgagccagca gggcctggcc cgtctgcctg    300
cactgctgaa acagcaccaa ccgcgctggg tcctggtgga gctgggcggt aacgacggtc    360
tgcgcggctt ccagccgcag cagaccgaac agactctgcg tcagattctg caggacgtga    420
aagctgctaa cgcggaaccg ctgctgatgc agattcgtct gccagcgaac tatggccgcc    480
gttacaacga agcgttctct gcaatctacc caaaactggc gaaagagttt gacgtcccgc    540
tgctgccgtt cttcatggag gaagtatacc tgaaaccgcg tggatgcaa gatgacggca    600

-continued

```
tccacccgaa ccgtgatgcg cagccgttca tcgctgactg gatggcgaag caactgcagc    660
cgctggtaaa ccacgattcc taattaaaga tctgtagtag gatccatgta gggtgaggtt    720
atagctatga agaaagtttg gctgaaccgt tatccggcag atgtaccgac tgaaattaac    780
ccagatcgtt accagtccct ggttgacatg ttcgaacagt ccgtggctcg ctacgccgat    840
cagcctgctt tcgtcaacat gggtgaggta atgacctttc gcaaactgga ggagcgttcc    900
cgtgctttcg cggcatacct gcagcagggt ctgggcctga agaaaggcga ccgcgtggcc    960
ctgatgatgc cgaacctgct gcaatatcct gtggcgctgt tcggtatcct gcgtgctggt   1020
atgatcgttg tcaatgttaa ccctctgtat accctcgtg aactggagca ccagctgaat   1080
gactctggtg cgtctgctat cgttatcgtt tccaatttcg cacatacgct ggagaaagtg   1140
gttgataaaa ccgcagtgca gcatgtcatt ctgactcgca tgggtgacca gctgtccacc   1200
gctaaaggta ctgtagtcaa cttcgttgtg aaatacatta agcgcctggt tccgaaatac   1260
cacctgccag atgcaattag ctttcgctct gcactgcata acggttaccg tatgcagtac   1320
gtaaaaccag agctggtgcc ggaagacctg gcctttctgc agtataccgg cggcaccacc   1380
ggcgtggcaa agggcgcgat gctgacccat cgtaacatgc tggcgaacct ggagcaggtt   1440
aacgcaacgt acgcccgct gctgcacccg ggtaaagaac tggtagttac ggcactgcct   1500
ctgtatcaca tctttgcact gacgatcaac tgtctgctgt tcattgaact gggtggtcag   1560
aacctgctga tcaccaaccc gcgtgacatt ccgggcctgg taaaagagct ggctaagtac   1620
ccgttcaccg ccattactgg cgtaaacact ctgtttaacg cgctgctgaa caacaaagag   1680
tttcagcagc tggacttctc tagcctgcac ctgagcgctg gcggtggcat gccggttcag   1740
caggttgtgg cagagcgttg ggtgaaactg accggccagt atctgctgga gggttatggt   1800
ctgaccgagt gtgcaccgct ggtcagcgtt aacccgtatg atattgatta ccactctggt   1860
tctattggtc tgccggttcc gtccacggaa gccaaactgg tggacgatga cgacaacgaa   1920
gtacctccgg gccagccggg tgagctgtgt gtcaagggtc cgcaggttat gctgggctac   1980
tggcagcgcc cggacgccac cgacgaaatc attaaaaacg gttggctgca taccggtgat   2040
atcgctgtaa tggacgaaga aggtttcctg cgtatcgtgg accgtaagaa agatatgatt   2100
ctggtgagcg gtttcaacgt gtacccgaac gaaattgagg acgtagttat gcaacaccct   2160
ggcgtgcagg aggtggcagc cgtgggcgtg ccgtccggtt cttctggtga ggctgtgaaa   2220
atctttgtcg ttaaaaagga cccgtccctg accgaagaat ctctggtgac gttttgccgc   2280
cgtcaactga ctggctacaa agtgccgaaa ctggtcgagt ccgcgatgga gctgccaaaa   2340
tctaacgtgg gtaagatcct gcgccgcgag ctgcgtgacg aggcacgtgg caaagttgac   2400
aataaagcat aaccgcgtag gaggacagct atgcgcccac ttcatccgat cgatttcatt   2460
ttcctgtccc tggagaaacg ccagcagccg atgcacgtag gtggtctgtt cctgttccag   2520
atcccggata cgctccgga cacctttatt caggacctgg tgaacgatat ccgtatctcc   2580
aagtctattc cggttccgcc gttcaacaac aagctgaacg gtctgttctg ggacgaagac   2640
gaggagttcg atctggatca ccatttccgt catattgcgc tgccgcaccc gggtcgcatc   2700
cgtgagctgc tgatttacat ctctcaggaa cacagcactc tcctcgatcg cgctaaacct   2760
ctgtggactt gcaacatcat tgaaggtatc gagggtaacc gtttcgccat gtacttcaag   2820
attcatcatg cgatggtgga tggtgtggcg ggtatgcgtc tgattgagaa aagcctgtcc   2880
catgatgtta ctgaaaagag catcgtaccg ccgtggtgcg ttgagggcaa acgtgctaaa   2940
cgcctgcgtg aaccgaagac cggcaaaatt aagaaaatca tgtctggtat taaatctcag   3000
```

| | |
|---|---|
| ctccaggcca ccccgaccgt tattcaagaa ctgtctcaga cggtcttcaa agacatcggc | 3060 |
| cgtaatccgg accacgtttc ctctttccag gcgccgtgct ccatcctcaa ccagcgtgtg | 3120 |
| tcttcttctc gtcgtttcgc agcacagagc tttgacctgg accgtttccg caacatcgcc | 3180 |
| aaatctctga acgtgaccat taacgacgtt gtcctggctg tgtgtagcgg tgctctgcgc | 3240 |
| gcttatctga tgtctcataa ctctctgcca tccaaaccgc tgatcgctat ggtcccagca | 3300 |
| agcatccgca acgatgattc tgatgtgtcc aaccgtatta ctatgattct ggccaacctc | 3360 |
| gctactcaca aagacgaccc tctgcagcgt ctggaaatca tccgccgctc cgtccagaac | 3420 |
| tctaaacagc gttttaaacg catgacttcc gaccagattc tgaactattc tgcggttgta | 3480 |
| tacggcccgg ctggtctgaa cattatcagc ggtatgatgc cgaaacgtca ggcttttaac | 3540 |
| ctggtaatca gcaacgttcc tggcccgcgt gagccgctgt actggaacgg cgcaaaactg | 3600 |
| gacgcactgt acccggcttc catcgttctg gatggccagg ctctgaacat cactatgacc | 3660 |
| tcttacctgg acaaactgga agtaggtctg atcgcgtgtc gcaatgcact gccgcgcatg | 3720 |
| cagaacctgc tgacccacct ggaggaggaa atccagctgt tgagggcgt tatcgccaaa | 3780 |
| caggaagata tcaaaacggc gaactaacca tggttgaatt c | 3821 |

<210> SEQ ID NO 11
<211> LENGTH: 7502
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

| | |
|---|---|
| cctgcagggt cagcaagctc tggaatttcc cgattctctg atgggagatc caaaaattct | 60 |
| cgcagtccct caatcacgat atcggtcttg gatcgccctg tagcttccga caactgctca | 120 |
| atttttcga gcatctctac cgggcatcgg aatgaaatta acggtgtttt agccatgtgt | 180 |
| tatacagtgt ttacaacttg actaacaaat acctgctagt gtatacatat tgtattgcaa | 240 |
| tgtatacgct attttcactg ctgtctttaa tggggattat cgcaagcaag taaaaaagcc | 300 |
| tgaaaacccc aataggtaag ggattccgag cttactcgat aattatcacc tttgagcgcc | 360 |
| cctaggagga ggcgaaaagc tatgtctgac aaggggtttg accctgaag tcgttgcgcg | 420 |
| agcattaagg tctgcggata gcccataaca tactttgtt gaacttgtgc gcttttatca | 480 |
| accccttaag ggcttgggag cgttttatgc ggccgctcac tgcccgcttt ccagtcggga | 540 |
| aacctgtcgt gccagctgca ttaatgaatc ggccaacgcg cggggagagg cggtttgcgt | 600 |
| attgggcgcc agggtggttt ttcttttcac cagtgagacg ggcaacagct gattgccctt | 660 |
| caccgcctgg ccctgagaga gttgcagcaa gcggtccacg ctggtttgcc ccagcaggcg | 720 |
| aaaatcctgt ttgatggtgg ttgacggcgg gatataacat gagctgtctt cggtatcgtc | 780 |
| gtatcccact accgagatat ccgcaccaac gcgcagcccg gactcggtaa tggcgcgcat | 840 |
| tgcgcccagc gccatctgat cgttggcaac cagcatcgca gtgggaacga tgccctcatt | 900 |
| cagcatttgc atggtttgtt gaaaaccgga catggcactc cagtcgcctt cccgttccgc | 960 |
| tatcggctga atttgattgc gagtgagata tttatgccag ccagccagac gcagacgcgc | 1020 |
| cgagacagaa cttaatgggc ccgctaacag cgcgatttgc tggtgaccca atgcgaccag | 1080 |
| atgctccacg cccagtcgcg taccgtcttc atgggagaaa ataatactgt tgatgggtgt | 1140 |
| ctggtcagag acatcaagaa ataacgccgg aacattagtg caggcagctt ccacagcaat | 1200 |

-continued

```
ggcatcctgg tcatccagcg gatagttaat gatcagccca ctgacgcgct gcgcgagaag   1260
attgtgcacc gccgctttac aggcttcgac gccgcttcgt tctaccatcg acaccaccac   1320
gctggcaccc agttgatcgg cgcgagattt aatcgccgcg acaatttgcg acggcgcgtg   1380
cagggccaga ctggaggtgg caacgccaat cagcaacgac tgtttgcccg ccagttgttg   1440
tgccacgcgg ttgggaatgt aattcagctc cgccatcgcc gcttccactt tttcccgcgt   1500
tttcgcagaa acgtggctgg cctggttcac cacgcgggaa acggtctgat aagagacacc   1560
ggcatactct gcgacatcgt ataacgttac tggtttcata ttcaccaccc tgaattgact   1620
ctcttccggg cgctatcatg ccataccgcg aaaggttttg caccattcga tggtgtcaac   1680
gtaaatgcat gccgcttcgc cttccaattg gactgcacgg tgcaccaatg cttctggcgt   1740
caggcagcca tcggaagctg tggtatggct gtgcaggtcg taaatcactg cataattcgt   1800
gtcgctcaag gcgcactccc gttctggata atgttttttg cgccgacatc ataacggttc   1860
tggcaaatat tctgaaatga gctgttgaca attaatcatc cggctcgtat aatgtgtgga   1920
attgtgagcg gataacaatt tcacacagga acagcatgg ccaaggaggc ccatatggcg   1980
gatactctgc tgattctggg tgattctctg tctgcaggct accgtatgtc cgcctccgcg   2040
gcctggccag ctctgctgaa tgataagtgg cagtctaaga cgtccgttgt gaacgcatcc   2100
atctctggcg acacgagcca gcagggcctg gccgtctgc ctgcactgct gaaacagcac   2160
caaccgcgct gggtcctggt ggagctgggc ggtaacgacg tctgcgcgg cttccagccg   2220 cagcagaccg aacagactct gcgtcagatt ctgcaggacg tgaaagctgc taacgcggaa   2280
ccgctgctga tgcagattcg tctgccagcg aactatggcc gccgttacaa cgaagcgttc   2340
tctgcaatct acccaaaact ggcgaaagag tttgacgtcc cgctgctgcc gttcttcatg   2400
gaggaagtat acctgaaacc gcagtggatg caagatgacg gcatccaccc gaaccgtgat   2460
gcgcagccgt tcatcgctga ctggatggcg aagcaactgc agccgctggt aaaccacgat   2520
tcctaattaa agatctgtag taggatccat gtagggtgag gttatagcta tgaagaaagt   2580
ttggctgaac cgttatccgg cagatgtacc gactgaaatt aacccagatc gttaccagtc   2640
cctggttgac atgttcgaac agtccgtggc tcgctacgcc gatcagcctg ctttcgtcaa   2700
catgggtgag gtaatgacct ttcgcaaact ggaggagcgt tcccgtgctt cgcggcata   2760 cctgcagcag ggtctgggcc tgaagaaagg cgaccgcgtg gccctgatga tgccgaacct   2820
gctgcaatat cctgtggcgc tgttcggtat cctgcgtgct ggtatgatcg ttgtcaatgt   2880
taaccctctg tataccctc gtgaactgga gcaccagctg aatgactctg gtgcgtctgc   2940
tatcgttatc gtttccaatt tcgcacatac gctggagaaa gtggttgata aaaccgcagt   3000
gcagcatgtc attctgactc gcatgggtga ccagctgtcc accgctaaag gtactgtagt   3060
caacttcgtt gtgaaataca ttaagcgcct ggttccgaaa taccacctgc cagatgcaat   3120
tagctttcgc tctgcactgc ataacggtta ccgtatgcag tacgtaaaac cagagctggt   3180
gccggaagac ctggcctttc tgcagtatac cggcggcacc accggcgtgg caaagggcgc   3240
gatgctgacc catcgtaaca tgctggcgaa cctggagcag gttaacgcaa cgtacgcccc   3300
gctgctgcac ccgggtaaag aactggtagt acggcactg cctctgtatc acatctttgc   3360
actgacgatc aactgtctgc tgttcattga actgggtggt cagaacctgc tgatcaccaa   3420
cccgcgtgac attccgggcc tggtaaaaga gctggctaag tacccgttca ccgccattac   3480
tggcgtaaac actctgttta acgcgctgct gaacaacaaa gagtttcagc agctggactt   3540
```

```
ctctagcctg cacctgagcg ctggcggtgg catgccggtt cagcaggttg tggcagagcg    3600
ttgggtgaaa ctgaccggcc agtatctgct ggagggttat ggtctgaccg agtgtgcacc    3660
gctggtcagc gttaacccgt atgatattga ttaccactct ggttctattg gtctgccggt    3720
tccgtccacg gaagccaaac tggtggacga tgacgacaac gaagtacctc cgggccagcc    3780
gggtgagctg tgtgtcaagg gtccgcaggt tatgctgggc tactggcagc gcccggacgc    3840
caccgacgaa atcattaaaa acggttggct gcataccggt gatatcgctg taatggacga    3900
agaaggtttc ctgcgtatcg tggaccgtaa gaaagatatg attctggtga gcggtttcaa    3960
cgtgtacccg aacgaaattg aggacgtagt tatgcaacac cctggcgtgc aggaggtggc    4020
agccgtgggc gtgccgtccg gttcttctgg tgaggctgtg aaaatctttg tcgttaaaaa    4080
ggacccgtcc ctgaccgaag aatctctggt gacgttttgc cgccgtcaac tgactggcta    4140
caaagtgccg aaactggtcg agttccgcga tgagctgcca aaatctaacg tgggtaagat    4200
cctgcgccgc gagctgcgtg acgaggcacg tggcaaagtt gacaataaag cataaccgcg    4260
taggaggaca gctatgcgcc cacttcatcc gatcgatttc attttcctgt ccctggagaa    4320
acgccagcag ccgatgcacg taggtggtct gttcctgttc cagatcccgg ataacgctcc    4380
ggacaccttt attcaggacc tggtgaacga tatccgtatc tccaagtcta ttccggttcc    4440
gccgttcaac aacaagctga acggtctgtt ctgggacgaa gacgaggagt tcgatctgga    4500
tcaccatttc cgtcatattg cgctgccgca cccgggtcgc atccgtgagc tgctgattta    4560
catctctcag gaacacagca ctctcctcga tcgcgctaaa cctctgtgga cttgcaacat    4620
cattgaaggt atcgagggta accgtttcgc catgtacttc aagattcatc atgcgatggt    4680
ggatggtgtg gcgggtatgc gtctgattga gaaaagcctg tcccatgatg ttactgaaaa    4740
gagcatcgta ccgccgtggt gcgttgaggg caaacgtgct aaacgcctgc gtgaaccgaa    4800
gaccggcaaa attaagaaaa tcatgtctgg tattaaatct cagctccagg ccaccccgac    4860
cgttattcaa gaactgtctc agacggtctt caaagacatc ggccgtaatc cggaccacgt    4920
ttcctctttc caggcgccgt gctccatcct caaccagcgt gtgtcttctt ctcgtcgttt    4980
cgcagcacag agctttgacc tggaccgttt ccgcaacatc gccaaatctc tgaacgtgac    5040
cattaacgac gttgtcctgg ctgtgtgtag cggtgctctg cgcgcttatc tgatgtctca    5100
taactctctg ccatccaaac cgctgatcgc tatggtccca gcaagcatcc gcaacgatga    5160
ttctgatgtg tccaaccgta ttactatgat tctggccaac ctcgctactc acaaagacga    5220
ccctctgcag cgtctggaaa tcatccgccg ctccgtccag aactctaaac agcgttttaa    5280
acgcatgact tccgaccaga ttctgaacta ttctgcggtt gtatacggcc cggctggtct    5340
gaacattatc agcggtatga tgccgaaacg tcaggctttt aacctggtaa tcagcaacgt    5400
tcctggcccg cgtgagccgc tgtactggaa cggcgcaaaa ctggacgcac tgtacccggc    5460
ttccatcgtt ctggatggcc aggctctgaa catcactatg acctcttacc tggacaaact    5520
ggaagtaggt ctgatcgcgt gtcgcaatgc actgccgcgc atgcagaacc tgctgaccca    5580
cctggaggag gaaatccagc tgtttgaggg cgttatcgcc aaacaggaag atatcaaaac    5640
ggcgaactaa ccatggttga attcggtttt ccgtcctgtc ttgattttca agcaaacaat    5700
gcctccgatt tctaatcgga ggcatttgtt tttgtttatt gcaaaacaa aaaatattgt    5760 tacaaatttt tacaggctat taagcctacc gtcataaata atttgccatt tactagtttt    5820
taattaacca gaaccttgac cgaacgcagc ggtggtaacg cgcagtggc ggttttcatg    5880 gcttgttatg actgtttttt tggggtacag tctatgcctc gggcatccaa gcagcaagcg    5940
```

```
cgttacgccg tgggtcgatg tttgatgtta tggagcagca acgatgttac gcagcagggc    6000
agtcgcccta aaacaaagtt aaacatcatg agggaagcgg tgatcgccga agtatcgact    6060
caactatcag aggtagttgg cgtcatcgag cgccatctcg aaccgacgtt gctggccgta    6120
catttgtacg gctccgcagt ggatggcggc ctgaagccac acagtgatat tgatttgctg    6180
gttacggtga ccgtaaggct tgatgaaaca acgcggcgag ctttgatcaa cgacctttg    6240 gaaacttcgg cttcccctgg agagagcgag attctccgcg ctgtagaagt caccattgtt    6300
gtgcacgacg acatcattcc gtggcgttat ccagctaagc gcgaactgca atttggagaa    6360
tggcagcgca atgacattct tgcaggtatc ttcgagccag ccacgatcga cattgatctg    6420
gctatcttgc tgacaaaagc aagagaacat agcgttgcct tggtaggtcc agcggcggag    6480
gaactctttg atccggttcc tgaacaggat ctatttgagg cgctaaatga aaccttaacg    6540
ctatggaact cgccgcccga ctgggctggc gatgagcgaa atgtagtgct tacgttgtcc    6600
cgcatttggt acagcgcagt aaccggcaaa atcgcgccga aggatgtcgc tgccgactgg    6660
gcaatggagc gcctgccggc ccagtatcag cccgtcatac ttgaagctag acaggcttat    6720 cttgacaag aagaagatcg cttggcctcg cgcgcagatc agttggaaga atttgtccac    6780
tacgtgaaag gcgagatcac caaggtagtc ggcaaataat gtctaacaat tcgttcaagc    6840
cgacgccgct tcgcggcgcg gcttaactca agcgttagat gcactaagca cataattgct    6900
cacagccaaa ctatcaggtc aagtctgctt ttattatttt taagcgtgca taataagccc    6960
tacacaaatt gggagatata tcatgaggcg cgccacgagt gcggggaaat ttcgggggcg    7020
atcgccccta tatcgcaaaa aggagttacc ccatcagagc tatagtcgag aagaaaacca    7080
tcattcactc aacaaggcta tgtcagaaga gaaactagac cggatcgaag cagccctaga    7140
gcaattggat aaggatgtgc aaacgctcca aacagagctt cagcaatccc aaaaatggca    7200
ggacaggaca tgggatgttg tgaagtgggt aggcggaatc tcagcgggcc tagcggtgag    7260
cgcttccatt gccctgttcg ggttggtctt tagattttct gtttccctgc cataaaagca    7320
cattcttata agtcatactt gtttacatca aggaacaaaa acggcattgt gccttgcaag    7380
gcacaatgtc tttctcttat gcacagatgg ggactggaaa ccacacgcac aattcccttt    7440
aaaagcaacc gcaaaaaata accatcaaaa taaaactgga caaattctca tgtgggccgg    7500
cc                                                                   7502
```

<210> SEQ ID NO 12
<211> LENGTH: 1442
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
tcactgcccg ctttccagtc gggaaacctg tcgtgccagc tgcattaatg aatcggccaa     60
cgcgcgggga gaggcggttt gcgtattggg cgccagggtg ttttttcttt tcaccagtga    120
gacgggcaac agctgattgc ccttcaccgc ctggccctga gagagttgca gcaagcggtc    180
cacgctggtt tgccccagca ggcgaaaatc ctgtttgatg gtggttgacg cgggatata    240 acatgagctg tcttcggtat cgtcgtatcc cactaccgag atatccgcac caacgcgcag    300
cccggactcg gtaatggcgc gcattgcgcc cagcgccatc tgatcgttgg caaccagcat    360
cgcagtggga acgatgccct cattcagcat ttgcatggtt tgttgaaaac cggacatggc    420
```

```
actccagtcg ccttcccgtt ccgctatcgg ctgaatttga ttgcgagtga gatatttatg    480
ccagccagcc agacgcagac cgcccgagac agaacttaat gggcccgcta acagcgcgat    540
ttgctggtga cccaatgcga ccagatgctc cacgcccagt cgcgtaccgt cttcatggga    600
gaaaataata ctgttgatgg gtgtctggtc agagacatca agaaataacg ccggaacatt    660
agtgcaggca gcttccacag caatggcatc ctggtcatcc agcggatagt taatgatcag    720
cccactgacg cgctgcgcga agagattgtg caccgccgct ttacaggctt cgacgccgct    780
tcgttctacc atcgacacca ccacgctggc acccagttga tcggcgcgag atttaatcgc    840
cgcgacaatt tgcgacggcg cgtgcagggc cagactggag gtggcaacgc caatcagcaa    900
cgactgtttg cccgccagtt gttgtgccac gcggttggga atgtaattca gctccgccat    960
cgccgcttcc actttttccc gcgttttcgc agaaacgtgg ctggcctggt tcaccacgcg    1020
ggaaacggtc tgataagaga caccggcata ctctgcgaca tcgtataacg ttactggttt    1080
catattcacc accctgaatt gactctcttc cgggcgctat catgccatac cgcgaaaggt    1140
tttgcaccat tcgatggtgt caacgtaaat gcatgccgct tcgccttcca attggactgc    1200
acggtgcacc aatgcttctg cgtcaggca gccatcggaa gctgtggtat ggctgtgcag    1260
gtcgtaaatc actgcataat tcgtgtcgct caaggcgcac tcccgttctg gataatgttt    1320
tttgcgccga catcataacg gttctggcaa atattctgaa atgagctgtt gacaattaat    1380
catccggctc gtataatgtg tggaattgtg agcggataac aatttcacac aggaaacagc    1440
at                                                                  1442
```

<210> SEQ ID NO 13
<211> LENGTH: 5615
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
cctgcagggt cagcaagctc tggaatttcc cgattctctg atgggagatc caaaaattct     60
cgcagtccct caatcacgat atcggtcttg gatcgccctg tagcttccga caactgctca    120 atttttcga gcatctctac cgggcatcgg aatgaaatta acggtgtttt agccatgtgt    180
tatacagtgt ttacaacttg actaacaaat acctgctagt gtatacatat tgtattgcaa    240
tgtatacgct atttttcactg ctgtctttaa tggggattat cgcaagcaag taaaaaagcc    300
tgaaaacccc aataggtaag ggattccgag cttactcgat aattatcacc tttgagcgcc    360
cctaggagga ggcgaaaagc tatgtctgac aaggggtttg accctgaag tcgttgcgcg    420 agcattaagg tctgcggata gcccataaca tactttttgtt gaacttgtgc gcttttatca    480
accccttaag ggcttgggag cgttttatgc ggccgcgggg ggggggggga aagccacgtt    540
gtgtctcaaa atctctgatg ttacattgca caagataaaa atatatcatc atgaacaata    600
aaactgtctg cttacataaa cagtaataca aggggtcata gatctgtagt aggatccatg    660
tagggtgagg ttatagctat gaagaaagtt tggctgaacc gttatccggc agatgtaccg    720
actgaaatta acccagatcg ttaccagtcc ctggttgaca tgttcgaaca gtccgtggct    780
cgctacgccg atcagcctgc tttcgtcaac atgggtgagg taatgaccct tcgcaaactg    840
gaggagcgtt cccgtgcttt cgcggcatac ctgcagcagg gtctgggcct gaagaaaggc    900
gaccgcgtgg ccctgatgat gccgaacctg ctgcaatatc ctgtggcgct gttcggtatc    960
```

```
ctgcgtgctg gtatgatcgt tgtcaatgtt aaccctctgt ataccctcg tgaactggag    1020 caccagctga atgactctgg tgcgtctgct atcgttatcg tttccaattt cgcacatacg    1080
ctggagaaag tggttgataa aaccgcagtg cagcatgtca ttctgactcg catgggtgac    1140
cagctgtcca ccgctaaagg tactgtagtc aacttcgttg tgaaatacat taagcgcctg    1200
gttccgaaat accacctgcc agatgcaatt agctttcgct ctgcactgca taacggttac    1260
cgtatgcagt acgtaaaacc agagctggtg ccggaagacc tggccttct gcagtatacc    1320 ggcggcacca ccggcgtggc aaagggcgcg atgctgaccc atcgtaacat gctggcgaac    1380
ctggagcagg ttaacgcaac gtacggcccg ctgctgcacc cgggtaaaga actggtagtt    1440
acggcactgc ctctgtatca catctttgca ctgacgatca actgtctgct gttcattgaa    1500
ctgggtggtc agaacctgct gatcaccaac ccgcgtgaca ttccgggcct ggtaaaagag    1560
ctggctaagt acccgttcac cgccattact ggcgtaaaca ctctgtttaa cgcgctgctg    1620
aacaacaaag agtttcagca gctggacttc tctagcctgc acctgagcgc tggcggtggc    1680
atgccggttc agcaggttgt ggcagagcgt tgggtgaaac tgaccggcca gtatctgctg    1740
gagggttatg gtctgaccga gtgtgcaccg ctggtcagcg ttaacccgta tgatattgat    1800
taccactctg gttctattgg tctgccggtt ccgtccacgg aagccaaact ggtggacgat    1860
gacgacaacg aagtacctcc gggccagccg ggtgagctgt gtgtcaaggg tccgcaggtt    1920
atgctgggct actggcagcg cccggacgcc accgacgaaa tcattaaaaa cggttggctg    1980
cataccggtg atatcgctgt aatggacgaa gaaggtttcc tgcgtatcgt ggaccgtaag    2040
aaagatatga ttctggtgag cggtttcaac gtgtacccga cgaaattga ggacgtagtt    2100 atgcaacacc ctggcgtgca ggaggtggca gccgtgggcg tgccgtccgg ttcttctggt    2160
gaggctgtga aaatctttgt cgttaaaaag gacccgtccc tgaccgaaga atctctggtg    2220
acgttttgcc gccgtcaact gactggctac aaagtgccga aactggtcga gttccgcgat    2280
gagctgccaa aatctaacgt gggtaagatc ctgcgccgcg agctgcgtga cgaggcacgt    2340
ggcaaagttg acaataaagc ataactcgac gcgtaggagg acagctatgc gcccacttca    2400
tccgatcgat ttcattttcc tgtccctgga gaaacgccag cagccgatgc acgtaggtgg    2460
tctgttcctg ttccagatcc cggataacgc tccggacacc tttattcagg acctggtgaa    2520
cgatatccgt atctccaagt ctattccggt tccgccgttc aacaacaagc tgaacggtct    2580
gttctgggac gaagacgagg agttcgatct ggatcaccat ttccgtcata ttgcgctgcc    2640
gcacccgggt cgcatccgtg agctgctgat ttacatctct caggaacaca gcactctcct    2700
cgatcgcgct aaacctctgt ggacttgcaa catcattgaa ggtatcgagg taaccgttt    2760 cgccatgtac ttcaagattc atcatgcgat ggtggatggt gtggcgggta tgcgtctgat    2820
tgagaaaagc ctgtcccatg atgttactga aaagagcatc gtaccgccgt ggtgcgttga    2880
gggcaaacgt gctaaacgcc tgcgtgaacc gaagaccggc aaaattaaga aaatcatgtc    2940
tggtattaaa tctcagctcc aggccacccc gaccgttatt caagaactgt ctcagacggt    3000
cttcaaagac atcggccgta atccggacca cgtttcctct ttccaggcgc cgtgctccat    3060
cctcaaccag cgtgtgtctt cttctcgtcg tttcgcagca cagagctttg acctggaccg    3120
tttccgcaac atcgccaaat ctctgaacgt gaccattaac gacgttgtcc tggctgtgtg    3180
tagcggtgct ctgcgcgctt atctgatgtc tcataactct ctgccatcca aaccgctgat    3240
cgctatggtc ccagcaagca tccgcaacga tgattctgat gtgtccaacc gtattactat    3300
```

```
gattctggcc aacctcgcta ctcacaaaga cgaccctctg cagcgtctgg aaatcatccg    3360
ccgctccgtc cagaactcta acagcgtttt taaacgcatg acttccgacc agattctgaa    3420
ctattctgcg gttgtatacg gcccggctgg tctgaacatt atcagcggta tgatgccgaa    3480
acgtcaggct tttaacctgg taatcagcaa cgttcctggc ccgcgtgagc cgctgtactg    3540
gaacggcgca aaactggacg cactgtaccc ggcttccatc gttctggatg ccaggctct    3600
gaacatcact atgacctctt acctggacaa actggaagta ggtctgatcg cgtgtcgcaa    3660
tgcactgccg cgcatgcaga acctgctgac ccacctggag gaggaaatcc agctgtttga    3720
gggcgttatc gccaaacagg aagatatcaa aacggcgaac taaccatggt tgaattcggt    3780
tttccgtcct gtcttgattt tcaagcaaac aatgcctccg atttctaatc ggaggcattt    3840
gttttgttt attgcaaaaa caaaaaatat tgttacaaat ttttacaggc tattaagcct    3900
accgtcataa ataatttgcc atttactagt ttttaattaa ccagaacctt gaccgaacgc    3960
agcggtggta acggcgcagt ggcggttttc atggcttgtt atgactgttt ttttgggta    4020
cagtctatgc ctcgggcatc caagcagcaa gcgcgttacg ccgtgggtcg atgtttgatg    4080
ttatggagca gcaacgatgt tacgcagcag ggcagtcgcc ctaaaacaaa gttaaacatc    4140
atgagggaag cggtgatcgc cgaagtatcg actcaactat cagaggtagt tggcgtcatc    4200
gagcgccatc tcgaaccgac gttgctggcc gtacatttgt acggctccgc agtggatggc    4260
ggcctgaagc acacagtga tattgatttg ctggttacgg tgaccgtaag gcttgatgaa    4320
acaacgcggc gagctttgat caacgacctt ttggaaactt cggcttcccc tggagagagc    4380
gagattctcc gcgctgtaga agtcaccatt gttgtgcacg acgacatcat ccgtggcgt    4440
tatccagcta agcgcgaact gcaatttgga gaatggcagc gcaatgacat tcttgcaggt    4500
atcttcgagc cagccacgat cgacattgat ctggctatct tgctgacaaa agcaagagaa    4560
catagcgttg ccttggtagg tccagcggcg gaggaactct ttgatccggt tcctgaacag    4620
gatctatttg aggcgctaaa tgaaacctta acgctatgga actcgccgcc cgactgggct    4680
ggcgatgagc gaaatgtagt gcttacgttg tcccgcattt ggtacagcgc agtaaccggc    4740
aaaatcgcgc cgaaggatgt cgctgccgac tgggcaatgg agcgcctgcc ggcccagtat    4800
cagcccgtca tacttgaagc tagacaggct tatcttggac aagaagaaga tcgcttggcc    4860
tcgcgcgcag atcagttgga agaatttgtc cactacgtga aaggcgagat caccaaggta    4920
gtcggcaaat aatgtctaac aattcgttca agccgacgcc gcttcgcggc gcggcttaac    4980
tcaagcgtta gatgcactaa gcacataatt gctcacagcc aaactatcag gtcaagtctg    5040
cttttattat ttttaagcgt gcataataag ccctacacaa attgggagat atatcatgag    5100
gcgcgccacg agtgcgggga aatttcgggg gcgatcgccc ctatatcgca aaaggagtt    5160
accccatcag agctatagtc gagaagaaaa ccatcattca ctcaacaagg ctatgtcaga    5220
agagaaacta gaccggatcg aagcagccct agagcaattg gataaggatg tgcaaacgct    5280
ccaaacagag cttcagcaat cccaaaaatg gcaggacagg acatgggatg ttgtgaagtg    5340
ggtaggcgga atctcagcgg gcctagcggt gagcgcttcc attgccctgt cgggttggt    5400
ctttagattt tctgtttccc tgccataaaa gcacattctt ataagtcata cttgtttaca    5460
tcaaggaaca aaaacggcat tgtgccttgc aaggcacaat gtctttctct tatgcacaga    5520
tggggactgg aaaccacacg cacaattccc ttaaaaagca accgcaaaaa ataaccatca    5580
aaataaaact ggacaaattc tcatgtgggc cggcc                              5615
```

<210> SEQ ID NO 14
<211> LENGTH: 4764
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
cctgcagggt cagcaagctc tggaatttcc cgattctctg atgggagatc caaaaattct      60
cgcagtccct caatcacgat atcggtcttg gatcgccctg tagcttccga caactgctca     120
atttttcga gcatctctac cgggcatcgg aatgaaatta acggtgtttt agccatgtgt      180
tatacagtgt ttacaacttg actaacaaat acctgctagt gtatacatat tgtattgcaa    240
tgtatacgct attttcactg ctgtctttaa tggggattat cgcaagcaag taaaaaagcc    300
tgaaaacccc aataggtaag ggattccgag cttactcgat aattatcacc tttgagcgcc    360
cctaggagga ggcgaaaagc tatgtctgac aaggggtttg acccctgaag tcgttgcgcg    420
agcattaagg tctgcggata gcccataaca tactttgtt gaacttgtgc gcttttatca     480
accccttaag ggcttgggag cgttttatgc ggccgcgggg ggggggggga aagccacgtt    540
gtgtctcaaa atctctgatg ttacattgca caagataaaa atatatcatc atgaacaata    600
aaactgtctg cttacataaa cagtaataca aggggtcata tggcggatac tctgctgatt    660
ctgggtgatt ctctgtctgc aggctaccgt atgtccgcct ccgcggcctg ccagctctg     720
ctgaatgata agtggcagtc taagacgtcc gttgtgaacg catccatctc tggcgacacg    780
agccagcagg gcctggcccg tctgcctgca ctgctgaaac agcaccaacc gcgctgggtc    840
ctggtggagc tgggcggtaa cgacggtctg cgcggcttcc agccgcagca gaccgaacag    900
actctgcgtc agattctgca ggacgtgaaa gctgctaacg cggaaccgct gctgatgcag    960
attcgtctgc cagcgaacta tggccgccgt tacaacgaag cgttctctgc aatctaccca   1020
aaactggcga aagagtttga cgtcccgctg ctgccgttct tcatggagga agtatacctg   1080
aaaccgcagt ggatgcaaga tgacggcatc cacccgaacc gtgatgcgca gccgttcatc   1140
gctgactgga tggcgaagca actgcagccg ctggtaaacc acgattccta attaaagatc   1200
tgtagtagga tccatgtagg gtgaggttat agctatgaag aaagtttggc tgaaccgtta   1260
tccggcagat gtaccgactg aaattaaccc agatcgttac cagtccctgg ttgacatgtt   1320
cgaacagtcc gtggctcgct acgccgatca gcctgctttc gtcaacatgg gtgaggtaat   1380
gacctttcgc aaactggagg agcgttcccg tgctttcgcg gcataccgtc agcagggtct   1440
gggcctgaag aaaggcgacc gcgtggccct gatgatgccg aacctgctgc aatatcctgt   1500
ggcgctgttc ggtatcctgc gtgctggtat gatcgttgtc aatgttaacc ctctgtatac   1560
ccctcgtgaa ctggagcacc agctgaatga ctctggtgcg tctgctatcg ttatcgtttc   1620
caatttcgca catacgctgg agaaagtggt tgataaaacc gcagtgcagc atgtcattct   1680
gactcgcatg ggtgaccagc tgtccaccgc taaaggtact gtagtcaact cgttgtgaa    1740
atacattaag cgcctggttc cgaaatacca cctgccagat gcaattagct ttcgctctgc   1800
actgcataac ggttaccgta tgcagtacgt aaaaccagag ctggtgccgg aagacctggc   1860
ctttctgcag tataccggcg gcaccaccgg cgtggcaaag ggcgcgatgc tgacccatcg   1920
taacatgctg gcgaacctgg agcaggttaa cgcaacgtac ggcccgctgc tgcacccggg   1980
taaagaactg gtagttacgg cactgcctct gtatcacatc tttgcactga cgatcaactg   2040
tctgctgttc attgaactgg gtggtcagaa cctgctgatc accaacccgc gtgacattcc   2100
```

```
gggcctggta aaagagctgg ctaagtaccc gttcaccgcc attactggcg taaacactct   2160
gtttaacgcg ctgctgaaca acaaagagtt tcagcagctg gacttctcta gcctgcacct   2220
gagcgctggc ggtggcatgc cggttcagca ggttgtggca gagcgttggg tgaaactgac   2280
cggccagtat ctgctggagg gttatggtct gaccgagtgt gcaccgctgg tcagcgttaa   2340
cccgtatgat attgattacc actctggttc tattggtctg ccggttccgt ccacggaagc   2400
caaactggtg gacgatgacg acaacgaagt acctccgggc cagccgggtg agctgtgtgt   2460
caagggtccg caggttatgc tgggctactg gcagcgcccg gacgccaccg acgaaatcat   2520
taaaaacggt tggctgcata ccggtgatat cgctgtaatg gacgaagaag gtttcctgcg   2580
tatcgtggac cgtaagaaag atatgattct ggtgagcggt ttcaacgtgt acccgaacga   2640
aattgaggac gtagttatgc aacaccctgg cgtgcaggag gtggcagccg tgggcgtgcc   2700
gtccggttct tctggtgagg ctgtgaaaat ctttgtcgtt aaaaaggacc cgtccctgac   2760
cgaagaatct ctggtgacgt tttgccgccg tcaactgact ggctacaaag tgccgaaact   2820
ggtcgagttc cgcgatgagc tgccaaaatc taacgtgggt aagatcctgc ccgcgagct   2880 gcgtgacgag gcacgtggca agttgacaa taaagcataa caattcggtt ttccgtcctg   2940
tcttgatttt caagcaaaca atgcctccga tttctaatcg gaggcatttg tttttgttta   3000
ttgcaaaaac aaaaaatatt gttacaaatt tttacaggct attaagccta ccgtcataaa   3060
taatttgcca tttactagtt tttaattaac cagaaccttg accgaacgca gcggtggtaa   3120
cggcgcagtg gcggttttca tggcttgtta tgactgtttt tttggggtac agtctatgcc   3180
tcgggcatcc aagcagcaag cgcgttacgc cgtgggtcga tgtttgatgt tatggagcag   3240
caacgatgtt acgcagcagg gcagtcgccc taaaacaaag ttaaacatca tgagggaagc   3300
ggtgatcgcc gaagtatcga ctcaactatc agaggtagtt ggcgtcatcg agcgccatct   3360
cgaaccgacg ttgctggccg tacatttgta cggctccgca gtggatggcg gcctgaagcc   3420
acacagtgat attgatttgc tggttacggt gaccgtaagg cttgatgaaa caacgcggcg   3480
agctttgatc aacgaccttt tggaaacttc ggcttcccct ggagagagcg agattctccg   3540
cgctgtagaa gtcaccattg ttgtgcacga cgacatcatt ccgtggcgtt atccagctaa   3600
gcgcgaactg caatttggag aatggcagcg caatgacatt cttgcaggta tcttcgagcc   3660
agccacgatc gacattgatc tggctatctt gctgacaaaa gcaagagaac atagcgttgc   3720
cttggtaggt ccagcggcgg aggaactctt tgatccggtt cctgaacagg atctatttga   3780
ggcgctaaat gaaaccttaa cgctatggaa ctcgccgccc gactgggctg cgatgagcg   3840 aaatgtagtg cttacgttgt cccgcatttg gtacagcgca gtaaccggca aaatcgcgcc   3900
gaaggatgtc gctgccgact gggcaatgga gcgcctgccg gcccagtatc agcccgtcat   3960
acttgaagct agacaggctt atcttggaca agaagaagat cgcttggcct cgcgcgcaga   4020
tcagttggaa gaatttgtcc actacgtgaa aggcgagatc accaaggtag tcggcaaata   4080
atgtctaaca attcgttcaa gccgacgccg cttcgcggcg cggcttaact caagcgttag   4140
atgcactaag cacataattg ctcacagcca actatcagg tcaagtctgc ttttattatt   4200
tttaagcgtg cataataagc cctacacaaa ttgggagata tatcatgagg cgcgccacga   4260
gtgcggggaa atttcggggg cgatcgcccc tatatcgcaa aaaggagtta ccccatcaga   4320
gctatagtcg agaagaaaac catcattcac tcaacaaggc tatgtcagaa gagaaactag   4380
accggatcga agcagcccta gagcaattgg ataaggatgt gcaaacgctc caaacagagc   4440
```

| | |
|---|---:|
| ttcagcaatc ccaaaaatgg caggacagga catgggatgt tgtgaagtgg gtaggcggaa | 4500 |
| tctcagcggg cctagcggtg agcgcttcca ttgccctgtt cgggttggtc tttagatttt | 4560 |
| ctgtttccct gccataaaag cacattctta taagtcatac ttgtttacat caaggaacaa | 4620 |
| aaacggcatt gtgccttgca aggcacaatg tctttctctt atgcacagat ggggactgga | 4680 |
| aaccacacgc acaattccct taaaaagcaa ccgcaaaaaa taaccatcaa aataaaactg | 4740 |
| gacaaattct catgtgggcc ggcc | 4764 |

<210> SEQ ID NO 15
<211> LENGTH: 5155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

| | |
|---|---:|
| accaatgctt aatcagtgag gcacctatct cagcgatctg tctatttcgt tcatccatag | 60 |
| ttgcctgact ccccgtcgtg tagataacta cgatacggga gggcttacca tctggcccca | 120 |
| gcgctgcgat gataccgcga gaaccacgct caccggctcc ggatttatca gcaataaacc | 180 |
| agccagccgg aagggccgag cgcagaagtg gtcctgcaac tttatccgcc tccatccagt | 240 |
| ctattaattg ttgccgggaa gctagagtaa gtagttcgcc agttaatagt ttgcgcaacg | 300 |
| ttgttgccat cgctacaggc atcgtggtgt cacgctcgtc gtttggtatg gcttcattca | 360 |
| gctccggttc ccaacgatca aggcgagtta catgatcccc catgttgtgc aaaaaagcgg | 420 |
| ttagctcctt cggtcctccg atcgttgtca gaagtaagtt ggccgcagtg ttatcactca | 480 |
| tggttatggc agcactgcat aattctctta ctgtcatgcc atccgtaaga tgcttttctg | 540 |
| tgactggtga gtactcaacc aagtcattct gagaatagtg tatgcggcga ccgagttgct | 600 |
| cttgcccggc gtcaatacgg gataataccg cgccacatag cagaacttta aaagtgctca | 660 |
| tcattggaaa acgttcttcg ggcgaaaac tctcaaggat cttaccgctg ttgagatcca | 720 |
| gttcgatgta acccactcgt gcacccaact gatcttcagc atcttttact ttcaccagcg | 780 |
| tttctgggtg agcaaaaaca ggaaggcaaa atgccgcaaa aaagggaata agggcgacac | 840 |
| ggaaatgttg aatactcata ttcttccttt ttcaatatta ttgaagcatt tatcagggtt | 900 |
| attgtctcat gagcggatac atatttgaat gtatttagaa aaataaacaa ataggggtca | 960 |
| gtgttacaac caattaacca attctgaaca ttatcgcgag cccatttata cctgaatatg | 1020 |
| gctcataaca ccccttgttt gcctggcggc agtagcgcgg tggtcccacc tgaccccatg | 1080 |
| ccgaactcag aagtgaaacg ccgtagcgcc gatggtagtg tggggactcc ccatgcgaga | 1140 |
| gtagggaact gccaggcatc aaataaaacg aaaggctcag tcgaaagact gggcctttcg | 1200 |
| cccgggctaa ttatggggtg tcgcccttat tcgactctat agtgaagttc ctattctcta | 1260 |
| gaaagtatag gaacttctga gtggggcct gcagggccac cacagccaaa ttcatcgtta | 1320 |
| atgtggactt gccgacgccc cctttttcgac taacaatcgc aattttttc atagacattt | 1380 |
| cccacagacc acatcaaatt acagcaattg atctagctga agtttaacc cacttccccc | 1440 |
| cagacccaga agaccagagg cgcttaagct tccccgaaca aactcaactg accgaggggg | 1500 |
| agggagccgt agcggcgttg gtgttggcgt aaatgacagg ccgagcaaag agcgatgaga | 1560 |
| ttttcccgac gattgtcttc ggggatgtaa ttttttgtggt ggacgcttaa ggttaaaaca | 1620 |
| gcccgcaggt gacgatcaat gcctttgacc ttcacatccg acggaataca aaccaagcca | 1680 |

```
cagagttcac agcgccagtc tgcatcctct tttacttgta aggcgatcgc ctgccaatca    1740
tcagaatatc gagaagaatg tttcatctaa acctagcgcc gcaagataat cctgaaatcg    1800
ctacagtatt aaaaaattct ggccaacatc acagccaata ctgcggccgc gggggggggg    1860
gggaaagcca cgttgtgtct caaaatctct gatgttacat tgcacaagat aaaaatatat    1920
catcatgaac aataaaactg tctgcttaca taaacagtaa tacaaggggt catatgtaac    1980
aggaattcgg ttttccgtcc tgtcttgatt ttcaagcaaa caatgcctcc gatttctaat    2040
cggaggcatt tgttttttgtt tattgcaaaa acaaaaaata ttgttacaaa tttttacagg    2100
ctattaagcc taccgtcata ataatttgc catttactag tttttaatta acccctatt    2160 tgtttatttt tctaaataca ttcaaatatg tatccgctca tgagacaata accctgataa    2220
atgcttcaat aatattgaaa aaggaagagt atgattgaac aagatggcct gcatgctggt    2280
tctccggctg cttgggtgga acgcctgttt ggttacgact gggctcagct gactattggc    2340
tgtagcgatg cagcggtttt ccgtctgtct gcacagggtc gtccggttct gtttgtgaaa    2400
accgacctgt ccgcgcact gaacgaactg caggacgaag cggcccgtct gtcctggctc    2460
gcgacgactg tgttccgtg cgcggcagtt ctggacgtag ttactgaagc cggtcgcgat    2520
tggctgctgc tgggtgaagt tccgggtcag gatctgctga gcagccacct cgctccggca    2580
gaaaaagttt ccatcatggc ggacgcgatg cgccgtctgc acccctgga cccggcaact    2640 tgcccgtttg accatcaggc taaacaccgt attgaacgtg cacgcactcg tatggaagcg    2700
ggtctggttg atcaggacga cctggatgaa gagcaccagg gcctcgcacc ggcggaactg    2760
tttgcacgtc tgaaagcccg catgccggac ggcgaagacc tggtggtaac gcatggcgac    2820
gcttgtctgc caaacattat ggtggaaaac ggccgcttct ctggttttat tgactgtggc    2880
cgtctgggtg tagctgatcg ctatcaggat atcgccctcg ctacccgcga tattgcagaa    2940
gaactgggtg gtgaatgggc tgaccgtttc ctggtgctgt acggtatcgc agcgccggat    3000
tctcagcgca ttgccttcta ccgtctgctg atgagttcc tctaaggcgc gccgaaactg    3060
cgccaagaat agctcacttc aaatcagtca cggttttgtt tagggcttgt ctggcgattt    3120
tggtgacata gacagtcaca gcaacagtag ccacaaaacc aagaatccgg atcgaccact    3180
gggcaatggg gttggcgctg gtgctttctg tgccgagggt cgcaagattt ccggccaggg    3240
agccaatgta gacatacatg atggtgccag ggatcatccc cacagagccg aggacatagt    3300
cttttaggga acgcccgtg accccatagg catagttaag cagattaaag ggaaatacag    3360
gtgagagacg cgtcaggaga acaatcttca ggccttcctt gcccacagct tcgtcgatgg    3420
cgcgaaattt cgggttgtcg gcgattttt ggctcaccca ttggcgggcc agataacgac    3480
ccactaggaa agcagcgatc gctcctaggg ttgcgccaac aaagacgtaa attgatccta    3540
aagcgacacc aaaaacaacc ccggctccca aggtcagaat cgaccccggt agaaaagcca    3600
ccgtcgccac cacataaagc accataaagg cgatggccgg ccaaaatgaa gtgaagttcc    3660
tatactttct agagaatagg aacttctata gtgagtcgaa taagggcgac acaaaattta    3720
ttctaaatgc ataataaata ctgataacat cttatagttt gtattatatt ttgtattatc    3780
gttgacatgt ataattttga tatcaaaaac tgattttccc tttattattt tcgagattta    3840
ttttcttaat tctctttaac aaactagaaa tattgtatat acaaaaaatc ataaataata    3900
gatgaatagt ttaattatag gtgttcatca atcgaaaaag caacgtatct tatttaaagt    3960
gcgttgcttt tttctcattt ataaggttaa ataattctca tatatcaagc aaagtgacag    4020
gcgcccttaa atattctgac aaatgctctt tccctaaact ccccccataa aaaacccgc    4080
```

```
cgaagcgggt ttttacgtta tttgcggatt aacgattact cgttatcaga accgcccagg    4140
gggcccgagc ttaagactgg ccgtcgtttt acaacacaga aagagtttgt agaaacgcaa    4200
aaaggccatc cgtcagggcc cttctgctta gtttgatgcc tggcagttcc ctactctcgc    4260
cttccgcttc ctcgctcact gactcgctgc gctcggtcgt tcggctgcgg cgagcggtat    4320
cagctcactc aaaggcggta atacggttat ccacagaatc aggggataac gcaggaaaga    4380
acatgtgagc aaaaggccag caaaaggcca ggaaccgtaa aaaggccgcg ttgctggcgt    4440
ttttccatag gctccgcccc cctgacgagc atcacaaaaa tcgacgctca agtcagaggt    4500
ggcgaaaccc gacaggacta taaagatacc aggcgtttcc ccctggaagc tccctcgtgc    4560
gctctcctgt tccgaccctg ccgcttaccg gatacctgtc cgcctttctc ccttcgggaa    4620
gcgtggcgct ttctcatagc tcacgctgta ggtatctcag ttcggtgtag gtcgttcgct    4680
ccaagctggg ctgtgtgcac gaaccccccg ttcagcccga ccgctgcgcc ttatccggta    4740
actatcgtct tgagtccaac ccggtaagac acgacttatc gccactggca gcagccactg    4800
gtaacaggat tagcagagcg aggtatgtag gcggtgctac agagttcttg aagtggtggg    4860
ctaactacgg ctacactaga agaacagtat ttggtatctg cgctctgctg aagccagtta    4920
ccttcggaaa aagagttggt agctcttgat ccggcaaaca accaccgct ggtagcggtg    4980 gttttttgt ttgcaagcag cagattacgc gcagaaaaaa aggatctcaa gaagatcctt    5040
tgatcttttc tacgggtct gacgctcagt ggaacgacgc gcgcgtaact cacgttaagg    5100
gattttggtc atgagcttgc gccgtcccgt caagtcagcg taatgctctg ctttt          5155
```

<210> SEQ ID NO 16
<211> LENGTH: 8459
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
cctgcagggc caccacagcc aaattcatcg ttaatgtgga cttgccgacg cccccttttc     60
gactaacaat cgcaatttt ttcatagaca tttcccacag accacatcaa attacagcaa    120
ttgatctagc tgaaagttta acccacttcc ccccagaccc agaagaccag aggcgcttaa    180
gcttccccga acaaactcaa ctgaccgagg gggagggagc cgtagcggcg ttggtgttgg    240
cgtaaatgac aggccgagca aagagcgatg agattttccc gacgattgtc ttcggggatg    300 taattttgt ggtggacgct taaggttaaa acagcccgca ggtgacgatc aatgcctttg    360
accttcacat ccgacggaat acaaaccaag ccacagagtt cacagcgcca gtctgcatcc    420
tcttttactt gtaaggcgat cgcctgccaa tcatcagaat atcgagaaga atgtttcatc    480
taaacctagc gccgcaagat aatcctgaaa tcgctacagt attaaaaaat tctggccaac    540
atcacagcca atactgcggc cgcgccccta tattatgcat ttatacccc acaatcatgt    600 caagaattca agcatcttaa ataatgttaa ttatcggcaa agtctgtgct ccccttctat    660
aatgctgaat tgagcattcg cctcctgaac ggtctttatt cttccattgt gggtctttag    720
attcacgatt cttcacaatc attgatctaa agatctttct agattctcga ggcatatgaa    780
gaaattgctc cccattctta tcggcctgag cctttctggg ttcagttcgt tgagccaggc    840
cgagaacctg atgcaagttt atcagcaagc acgccttagt aacccggaat tgcgtaagtc    900
tgccgccgat cgtgatgctg cctttgaaaa aattaatgaa gcgcgcagtc cattactgcc    960
```

```
acagctaggt ttaggtgcag attacaccta tagcaacggc taccgcgacg cgaacggcat   1020
caactctaac gcgaccagtg cgtccttgca gttaactcaa tccattttg atatgtcgaa    1080 atggcgtgcg ttaacgctgc aggaaaaagc agcagggatt caggacgtca cgtatcagac   1140
cgatcagcaa accttgatcc tcaacaccgc gaccgcttat ttcaacgtgt tgaatgctat   1200
tgacgttctt tcctatacac aggcacaaaa agaagcgatc taccgtcaat tagatcaaac   1260
cacccaacgt tttaacgtgg gcctggtagc gatcaccgac gtgcagaacg cccgcgcaca   1320
gtacgatacc gtgctggcga acgaagtgac cgcacgtaat aaccttgata cgcggtaga    1380 gcagctgcgc cagatcaccg gtaactacta tccggaactg gctgcgctga atgtcgaaaa   1440
ctttaaaacc gacaaaccac agccggttaa cgcgctgctg aaagaagccg aaaaacgcaa   1500
cctgtcgctg ttacaggcac gcttgagcca ggacctggcg cgcgagcaaa ttcgccaggc   1560
gcaggatggt cacttaccga ctctggattt aacggcttct accgggattt ctgacacctc   1620
ttatagcggt tcgaaaaccc gtggtgccgc tggtacccag tatgacgata gcaatatggg   1680
ccagaacaaa gttggcctga gcttctcgct gccgatttat cagggcggaa tggttaactc   1740
gcaggtgaaa caggcacagt acaactttgt cggtgccagc gagcaactgg aaagtgccca   1800
tcgtagcgtc gtgcagaccg tgcgttcctc cttcaacaac attaatgcat ctatcagtag   1860
cattaacgcc tacaaacaag ccgtagtttc cgctcaaagc tcattagacg cgatggaagc   1920
gggctactcg gtcggtacgc gtaccattgt tgatgtgttg gatgcgacca ccacgttgta   1980
caacgccaag caagagctgg cgaatgcgcg ttataactac ctgattaatc agctgaatat   2040
taagtcagct ctgggtacgt tgaacgagca ggatctgctg gcactgaaca atgcgctgag   2100
caaaccggtt tccactaatc cggaaaaacgt tgcaccgcaa acgccggaac agaatgctat   2160
tgctgatggt tatgcgcctg atagcccggc accagtcgtt cagcaaacat ccgcacgcac   2220
taccaccagt aacggtcata acccttccg taactgagga tccaaggtgg ctacttcaac    2280
gatagcttaa acttcgctgc tccagcgagg ggatttcact ggtttgaatg cttcaatgct   2340
tgccaaaaga gtgctactgg aacttacaag agtgaccctg cgtcagggga gctagcactc   2400
aaaaaagact cctccaattc cgtccatgaa caaaaacaga gggtttacgc ctctggcggt   2460
cgttctgatg ctctcaggca gcttagccct aacaggatgt gacgacaaac aggcccaaca   2520
aggtggccag cagatgcccg ccgttggcgt agtaacagtc aaaactgaac ctctgcagat   2580
cacaaccgag cttccgggtc gcaccagtgc ctaccggatc gcagaagttc gtcctcaagt   2640
tagcgggatt atcctgaagc gtaatttcaa agaaggtagc gacatcgaag caggtgtctc   2700
tctctatcag attgatcctg cgacctatca ggcgacatac gacagtgcga aggtgatct    2760 ggcgaaagcc caggctgcag ccaatatcgc gcaattgacg gtgaatcgtt atcagaaact   2820
gctcggtact cagtacatca gtaagcaaga gtacgatcag gctctggctg atgcgcaaca   2880
ggcgaatgct gcgtaactg cggcgaaagc tgccgttgaa actgcgcgga tcaatctggc    2940
ttacaccaaa gtcacctctc cgattagcgg tcgcattggt aagtcgaacg tgacggaagg   3000
cgcattggta cagaacggtc aggcgactgc gctggcaacc gtgcagcaac ttgatccgat   3060
ctacgttgat gtgacccagt ccagcaacga cttcctgcgc ctgaaacagg aactggcgaa   3120
tggcacgctg aaacaagaga acggcaaagc caaagtgtca ctgatcacca gtgacggcat   3180
taagttcccg caggacggta cgctggaatt ctctgacgtt accgttgatc agaccactgg   3240
gtctatcacc ctacgcgcta tcttcccgaa cccggatcac actctgctgc cgggtatgtt   3300
```

```
cgtgcgcgca cgtctggaag aagggcttaa tccaaacgct attttagtcc cgcaacaggg    3360
cgtaacccgt acgccgcgtg gcgatgccac cgtactggta gttggcgcgg atgacaaagt    3420
ggaaacccgt ccgatcgttg caagccaggc tattggcgat aagtggctgg tgacagaagg    3480
tctgaaagca ggcgatcgcg tagtaataag tgggctgcag aaagtgcgtc ctggtgtcca    3540
ggtaaaagca caagaagtta ccgctgataa taaccagcaa gccgcaagcg gtgctcagcc    3600
tgaacagtcc aagtcttaac ttaaacagga gccgttaaga catgcctaat ttctttatcg    3660
atcgcccgat ttttgcgtgg gtgatcgcca ttatcatcat gttggcaggg gggctggcga    3720
tcctcaaact gccggtggcg caatatccta cgattgcacc gccggcagta acgatctccg    3780
cctcctaccc cggcgctgat gcgaaaacag tgcaggacac ggtgacacag gttatcgaac    3840
agaatatgaa cggtatcgat aacctgatgt acatgtcctc taacagtgac tccacgggta    3900
ccgtgcagat caccctgacc tttgagtctg gtactgatgc ggatatcgcg caggttcagg    3960
tgcagaacaa actgcagctg gcgatgccgt tgctgccgca agaagttcag cagcaagggg    4020
tgagcgttga gaaatcatcc agcagcttcc tgatggttgt cggcgttatc aacaccgatg    4080
gcaccatgac gcaggaggat atctccgact acgtggcggc gaatatgaaa gatgccatca    4140
gccgtacgtc gggcgtgggt gatgttcagt tgttcggttc acagtacgcg atgcgtatct    4200
ggatgaaccc gaatgagctg aacaaattcc agctaacgcc ggttgatgtc attaccgcca    4260
tcaaagcgca gaacgcccag gttgcggcgg gtcagctcgg tggtacgccg ccggtgaaag    4320
gccaacagct taacgcctct attattgctc agacgcgtct gacctctact gaagagttcg    4380
gcaaaatcct gctgaaagtg aatcaggatg gttcccgcgt gctgctgcgt gacgtcgcga    4440
agattgagct gggtggtgag aactacgaca tcatcgcaga gtttaacggc caaccggctt    4500
ccggtctggg gatcaagctg gcgaccggtc aaacgcgcct ggataccgct gcggcaatcc    4560
gtgctgaact ggcgaagatg gaaccgttct tcccgtcggg tctgaaaatt gtttacccat    4620
acgacaccac gccgttcgtg aaaatctcta ttcacgaagt ggttaaaacg ctggtcgaag    4680
cgatcatcct cgtgttcctg gttatgtatc tgttcctgca gaacttccgc gcgacgttga    4740
ttccgaccat tgccgtaccg gtggtattgc tcgggacctt tgccgtcctt gccgcctttg    4800
gcttctcgat aaacacgcta acaatgttcg ggatggtgct cgccatcggc ctgttggtgg    4860
atgacgccat cgttgtggta gaaaacgttg agcgtgttat ggcggaagaa ggtttgccgc    4920
caaaagaagc tacccgtaag tcgatggggc agattcaggg cgctctggtc ggtatcgcga    4980
tggtactgtc ggcggtattc gtaccgatgg ccttctttgg cggttctact ggtgctatct    5040
atcgtcagtt ctctattacc attgtttcag caatggcgct gtcggtactg gtggcgttga    5100
tcctgactcc agctctttgt gccaccatgc tgaaaccgat tgccaaaggc gatcacgggg    5160
aaggtaaaaa aggcttcttc ggctggttta accgcatgtt cgagaagagc acgcaccact    5220
acaccgacag cgtaggcggt attctgcgca gtacggggcg ttacctggtg ctgtatctga    5280
tcatcgtggt cggcatggcc tatctgttcg tgcgtctgcc aagctccttc ttgccagatg    5340
aggaccaggg cgtgtttatg accatggttc agctgccagc aggtgcaacg caggaacgta    5400
cacagaaagt gctcaatgag gtaacgcatt actatctgac caaagaaaag aacaacgttg    5460
agtcggtgtt cgccgttaac ggcttcggct ttgcgggacg tggtcagaat accggtattg    5520
cgttcgtttc cttgaaggac tgggccgatc gtccgggcga agaaaacaaa gttgaagcga    5580
ttaccatgcg tgcaacacgc gctttctcgc aaatcaaaga tgcgtggctt ttcgccttta    5640
acctgcccgc aatcgtggaa ctgggtactg caaccggctt tgactttgag ctgattgacc    5700
```

-continued

```
aggctggcct tggtcacgaa aaactgactc aggcgcgtaa ccagttgctt gcagaagcag    5760
cgaagcaccc tgatatgttg accagcgtac gtccaaacgg tctggaagat accccgcagt    5820
ttaagattga tatcgaccag gaaaaagcgc aggcgctggg tgtttctatc aacgacatta    5880
acaccactct gggcgctgca tggggcggca gctatgtgaa cgactttatc gaccgcggtc    5940
gtgtgaagaa agtttatgtc atgtcagaag cgaaataccg tatgctgccg gatgatatcg    6000
gcgactggta tgttcgtgct gctgatggtc agatggtgcc attctcggcg ttctcctctt    6060
ctcgttggga gtacggttcg ccgcgtctgg aacgttacaa cggcctgcca tccatggaaa    6120
tcttaggcca ggcggcaccg ggtaaaagta ccggtgaagc aatggagctg atggaacaac    6180
tggcgagcaa actgcctacc ggtgttggct atgactggac ggggatgtcc tatcaggaac    6240
gtctctccgg caaccaggca ccttcactgt acgcgatttc gttgattgtc gtgttcctgt    6300
gtctggcggc gctgtacgag agctggtcga ttccgttctc cgttatgctg gtcgttccgc    6360
tgggggttat cggtgcgttg ctggctgcca ccttccgtgg cctgaccaat gacgtttact    6420
tccaggtagg cctgctcaca accattgggt tgtcggcgaa gaacgcgatc cttatcgtcg    6480
aattcgccaa agacttgatg gataaagaag gtaaaggtct gattgaagcg acgcttgatg    6540
cggtgcggat gcgtttacgt ccgatcctga tgacctcgct ggcgtttatc ctcggcgtta    6600
tgccgctggt tatcagtact ggtgctggtt ccggcgcgca gaacgcagta ggtaccggtg    6660
taatgggcgg gatggtgacc gcaacggtac tggcaatctt cttcgttccg gtattctttg    6720
tggtggttcg ccgccgcttt agccgcaaga atgaagatat cgagcacagc catactgtcg    6780
atcatcattg agagctcttg aattcggttt tccgtcctgt cttgattttc aagcaaacaa    6840
tgcctccgat ttctaatcgg aggcatttgt ttttgtttat tgcaaaaaca aaaaatattg    6900
ttacaaattt ttacaggcta ttaagcctac cgtcataaat aatttgccat ttactagttt    6960
ttaattaaac ccctatttgt ttatttttct aaatacattc aaatatgtat ccgctcatga    7020
gacaataacc ctgataaatg cttcaataat attgaaaaag gaagagtatg attgaacaag    7080
atggcctgca tgctggttct ccggctgctt gggtggaacg cctgtttggt tacgactggg    7140
ctcagctgac tattggctgt agcgatgcag cggttttccg tctgtctgca cagggtcgtc    7200
cggttctgtt tgtgaaaacc gacctgtccg gcgcactgaa cgaactgcag gacgaagcgg    7260
cccgtctgtc ctggctcgcg acgactggtg ttccgtgcgc ggcagttctg gacgtagtta    7320
ctgaagccgg tcgcgattgg ctgctgctgg gtgaagttcc gggtcaggat ctgctgagca    7380
gccacctcgc tccggcagaa aaagtttcca tcatggcgga cgcgatgcgc cgtctgcaca    7440
ccctggaccc ggcaacttgc ccgtttgacc atcaggctaa acaccgtatt gaacgtgcac    7500
gcactcgtat ggaagcgggt ctggttgatc aggacgacct ggatgaagag caccagggcc    7560
tcgcaccggc ggaactgttt gcacgtctga agcccgcat gccggacggc gaagacctgg    7620
tggtaacgca tggcgacgct tgtctgccaa acattatggt ggaaaacggc cgcttctctg    7680
gttttattga ctgtggccgt ctgggtgtag ctgatcgcta tcaggatatc gccctcgcta    7740
cccgcgatat tgcagaagaa ctgggtggtg aatgggctga ccgtttcctg gtgctgtacg    7800
gtatcgcagc gccggattct cagcgcattg ccttctaccg tctgctggat gagttcttct    7860
aaggcgcgcc gaaactgcgc caagaatagc tcacttcaaa tcagtcacgg ttttgtttag    7920
ggcttgtctg gcgattttgg tgacatagac agtcacagca acagtagcca caaaaccaag    7980
aatccggatc gaccactggg caatgggggtt ggcgctggtg ctttctgtgc cgagggtcgc    8040
```

| | |
|---|---|
| aagatttccg gccagggagc caatgtagac atacatgatg gtgccaggga tcatccccac | 8100 |
| agagccgagg acatagtctt ttagggaaac gcccgtgacc ccataggcat agttaagcag | 8160 |
| attaaaggga atacaggtg agagacgcgt caggagaaca atcttcaggc cttccttgcc | 8220 |
| cacagcttcg tcgatggcgc gaaatttcgg gttgtcggcg attttttggc tcacccattg | 8280 |
| gcgggccaga taacgaccca ctaggaaagc agcgatcgct cctagggttg cgccaacaaa | 8340 |
| gacgtaaatt gatcctaaag cgacaccaaa acaaccccg gctcccaagg tcagaatcga | 8400 |
| ccccggtaga aaagccaccg tcgccaccac ataaagcacc ataaaggcga tggccggcc | 8459 |

<210> SEQ ID NO 17
<211> LENGTH: 169
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

| | |
|---|---|
| tccctctcag ctcaaaaagt atcaatgatt acttaatgtt tgttctgcgc aaacttcttg | 60 |
| cagaacatgc atgatttaca aaagttgta gtttctgtta ccaattgcga atcgagaact | 120 |
| gcctaatctg ccgagtatgc aagctgcttt gtaggcagat gaatcccat | 169 |

<210> SEQ ID NO 18
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

| | |
|---|---|
| gcttgtagca attgctacta aaaactgcga tcgctgctga aatgagctgg aattttgtcc | 60 |
| ctctcagctc aaaaagtatc aatgattact taatgtttgt tctgcgcaaa cttcttgcag | 120 |
| aacatgcatg atttacaaaa agttgtagtt tctgttacca attgcgaatc gagaactgcc | 180 |
| taatctgccg agtatgcgat cctttagcag gaggaaaacc at | 222 |

<210> SEQ ID NO 19
<211> LENGTH: 597
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

| | |
|---|---|
| gctactcatt agttaagtgt aatgcagaaa acgcatattc tctattaaac ttacgcatta | 60 |
| atacgagaat tttgtagcta cttatactat tttacctgag atcccgacat aaccttagaa | 120 |
| gtatcgaaat cgttacataa acattcacac aaaccacttg acaaatttag ccaatgtaaa | 180 |
| agactacagt ttctccccgg tttagttcta gagttaccct cagtgaaaca tcggcggcgt | 240 |
| gtcagtcatt gaagtagcat aaatcaattc aaaataccct gcgggaaggc tgcgccaaca | 300 |
| aaattaaata tttggttttt cactattaga gcatcgattc attaatcaaa accttaccc | 360 |
| cccagccccc ttcccttgta gggaagtggg agccaaactc ccctctccgc gtcggagcga | 420 |
| aaagtctgag cggaggtttc ctccgaacag aacttttaaa gagagagggg ttgggggaga | 480 |
| ggttctttca agattactaa attgctatca ctagacctcg tagaactagc aaagactacg | 540 |

```
ggtggattga tcttgagcaa aaaaacttta tgagaacttt agcaggagga aaaccat        597
```

<210> SEQ ID NO 20
<211> LENGTH: 2296
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
gattacccta tatcgggctt ttctcaataa aatctttatt ttttgaggtg cttttttagcc      60
ataaataatc actttagtat aaaattttga cggcgtaaag ttgataaaat agaattaaga     120
atggactatc ggtacagaaa aaatgggtaa ctggatggtg aataaacttc ccttacccaa     180
tgcactctcc accgttaaag acccctatg cttaacggtg atcacctggg caatggcgag      240
tcccaacccct gtccccccccg ttttgcgcga acgatctcga ttaactcggt aaaaacgctc   300
aaaaatgtgt tcctgttggt cgggggcaat gccgatgccg gtatcttgca cggtgatgat    360
agccatctgt tcatgggatg tcagggtaat atcaacacgt cccccagcag ttgtgtattg    420
aatggcgttg gcaattaggt ttgagaccag tcgatagagt tgggattcat taccccaggc    480
gtaaacttcc cctgaactca gatcactgct gagatcaatg tgggcggcga tcgctaattc    540
taaaaactct tcggtgaggt cactgactaa atcatttaaa caacaaagcc gccaatcttc    600
ggcggtggtt tcctgctcta agcgacttag tagcaataaa tccgtaatca attggcttaa    660
tcgccttccc tgtcgttcaa cggtatgtag catggtgtta atttctgggg aatggcttga    720
gtcgatgcgt aataccgctt ccaccgtggc caacagacta gccaatggcg atcgtaattc    780
atgggctgca ttcgcggtga attgttgttg ttgttggtag gactggtaaa tgggacgcat    840
ggctaacccc gctaagcccc aactggagaa ggcgaccaaa cccagggcaa tgggaaaact    900
aagccctaaa atccaaagaa tacgtttatt ttcggcatca aaggctgcca ggctccggcc    960
aatttgtaga tagccccagg aagatttgtc tgtattaccg gcgctatgca aaatggtggt   1020
gaattgtcga taccgatcgc cggttggggg gtgaatagtc tgccaagttt cctggttaaa   1080
aatggaggat agggaagccg gttgattagg cgaaaaagcc agcaggttgc cttgataatc   1140
aaataaacga atgtaatata aactgcgatc actaatgccc aacgtgtgac gttcaatcag   1200
ggtggggttg acctggcagg gttggttgac caaacacaga tcgggcaaca tttttttgtaa  1260
tactccggtg ggactagcat tactcggcaa catcggctct aaactgtcat gcaacgtccc   1320
ggcgatcgac tccacttctc gctccaacgc catccagttg gcctgcacaa tggcacgata   1380
aaccccaaac cccaacaggg taagaattcc cccattact agggcatacc agaaagccaa    1440
ttgcagacga ctacgggcaa agaggcgacg ggtattcatg gcgatagggt gaaccgatag   1500
ccttgaccgg gaactgtttt aattgggcaa ggacaatttt gttgagctag cttgcgtcgt   1560
atcaaacgca tttgggccgc caccacatta ctcatgggct cctcatcaag atcccacagt   1620
tgttgccgga tcttgctacc ggaaatgatc cgctctgggt tttgcatcag atattgaaaa   1680
atttgaaatt ctcttacggt taaagcaatt tcctgtcttt ctaggtttag tggctccgag   1740
atagttaccg ataacagatt attactggga tcaaggctga agttgcccaa agttaaaatt   1800
tgcggttgga attgtggcga tcgccgttgt agtgcccgca gtcttgctaa tagctctgcc   1860
atcacaaacg gttttgttag atagtcatct gccccggcat ctagtccttc gacacggttt   1920
tccggttctc ctaacgctgt taacatcaac accggcaagg aattaccctg ggttctcagt   1980
```

```
tttgacaga gttccaaacc cgataatccc ggcagtaacc aatccacaat ggcaagggtg    2040
tattccgtcc attgattttc caaataatcc caagcttggg agccatccgt cacccaatcc    2100
accacatact tttcactaac tagcactttc ttaatagcca ttcccaaatc cgtctcatct    2160
tccaccagca aaattcgcat cgcctctgcc ttttttataa cggtctgatc ttagcggggg    2220
aaggagattt tcacctgaat tcataccccc ctttggcaga ctgggaaaat cttggacaaa    2280
ttaggaggaa aaccat                                                    2296
```

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
gctatgcctg cagggccttt tatgaggag cggta                                35
```

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
gctatggcgg ccgctcttca tgacagaccc tatggatact a                        41
```

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
gctatgggcg cgccttatct gactccagac gcaaca                              36
```

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
gctatgggcc ggccgatcct tggatcaact caccct                              36
```

<210> SEQ ID NO 25
<211> LENGTH: 658
<212> TYPE: PRT
<213> ORGANISM: Thermosynechococcus elongates

<400> SEQUENCE: 25

Met Met Ser Ala Ala Tyr Thr Tyr Thr Pro Pro Gly Gly Leu Pro Gln
1               5                   10                  15

Asp Ala Ser Leu Pro Asp His Phe Leu Ala Tyr Lys Arg Leu Gln Ser
            20                  25                  30

Leu Pro Glu Met Trp Pro Leu Leu Ala Gln Arg His Gly Asp Val Val

```
                  35                  40                  45
Ala Leu Asp Ala Pro Tyr Glu Asp Pro Thr Arg Ile Thr Tyr Ser
 50                  55                  60

Glu Leu Tyr Gln Arg Ile Gln Arg Phe Ala Ala Gly Leu Gln Ala Leu
 65                  70                  75                  80

Gly Val Ala Ala Gly Asp Arg Val Ala Leu Phe Pro Asp Asn Ser Pro
                 85                  90                  95

Arg Trp Leu Ile Ala Asp Gln Gly Ser Met Met Ala Gly Ala Ile Asn
                100                 105                 110

Val Val Arg Ser Gly Thr Ala Asp Ala Gln Glu Leu Leu Tyr Ile Leu
            115                 120                 125

Arg Asp Ser Gly Ala Thr Leu Leu Leu Ile Glu Asn Leu Ala Thr Leu
        130                 135                 140

Gly Lys Leu Gln Glu Pro Leu Val Asp Thr Gly Val Lys Thr Val Val
145                 150                 155                 160

Leu Leu Ser Gly Glu Ser Pro Glu Leu Ala Gly Phe Pro Leu Arg Leu
                165                 170                 175

Leu Asn Phe Gly Gln Val Phe Thr Glu Gly Gln Tyr Gly Thr Val Arg
            180                 185                 190

Ala Val Ala Ile Thr Pro Asp Asn Leu Ala Thr Leu Met Tyr Thr Ser
        195                 200                 205

Gly Thr Thr Gly Gln Pro Lys Gly Val Met Val Thr His Gly Gly Leu
    210                 215                 220

Leu Ser Gln Ile Val Asn Leu Trp Ala Ile Val Gln Pro Gln Val Gly
225                 230                 235                 240

Asp Arg Val Leu Ser Ile Leu Pro Ile Trp His Ala Tyr Glu Arg Val
                245                 250                 255

Ala Glu Tyr Phe Leu Phe Ala Cys Gly Cys Ser Gln Thr Tyr Thr Asn
            260                 265                 270

Leu Arg His Phe Lys Asn Asp Leu Lys Arg Cys Lys Pro His Tyr Met
        275                 280                 285

Ile Ala Val Pro Arg Ile Trp Glu Ser Phe Tyr Glu Gly Val Gln Lys
    290                 295                 300

Gln Leu Arg Asp Ser Pro Ala Thr Lys Arg Arg Leu Ala Gln Phe Phe
305                 310                 315                 320

Leu Ser Val Gly Gln Gln Tyr Ile Leu Gln Arg Arg Leu Leu Thr Gly
                325                 330                 335

Leu Ser Leu Thr Asn Pro His Pro Arg Gly Trp Gln Lys Trp Leu Ala
            340                 345                 350

Arg Val Gln Thr Leu Leu Leu Lys Pro Leu Tyr Glu Leu Gly Glu Lys
        355                 360                 365

Arg Leu Tyr Ser Lys Ile Arg Glu Ala Thr Gly Gly Glu Ile Lys Gln
    370                 375                 380

Val Ile Ser Gly Gly Gly Ala Leu Ala Pro His Leu Asp Thr Phe Tyr
385                 390                 395                 400

Glu Val Ile Asn Leu Glu Val Leu Val Gly Tyr Gly Leu Thr Glu Thr
                405                 410                 415

Ala Val Val Leu Thr Ala Arg Arg Ser Trp Ala Asn Leu Arg Gly Ser
            420                 425                 430

Ala Gly Arg Pro Ile Pro Asp Thr Ala Ile Lys Ile Val Asp Pro Glu
        435                 440                 445

Thr Lys Ala Pro Leu Glu Phe Gly Gln Lys Gly Leu Val Met Ala Lys
    450                 455                 460
```

-continued

```
Gly Pro Gln Val Met Arg Gly Tyr Tyr Asn Gln Pro Glu Ala Thr Ala
465                 470                 475                 480

Lys Val Leu Asp Ala Glu Gly Trp Phe Asp Thr Gly Asp Leu Gly Tyr
                485                 490                 495

Leu Thr Pro Asn Gly Asp Leu Val Leu Thr Gly Arg Gln Lys Asp Thr
            500                 505                 510

Ile Val Leu Ser Asn Gly Glu Asn Ile Glu Pro Gln Pro Ile Glu Asp
            515                 520                 525

Ala Cys Val Arg Ser Pro Tyr Ile Asp Gln Ile Met Leu Val Gly Gln
        530                 535                 540

Asp Gln Lys Ala Leu Gly Ala Leu Ile Val Pro Asn Leu Glu Ala Leu
545                 550                 555                 560

Glu Ala Trp Val Val Ala Lys Gly Tyr Arg Leu Glu Leu Pro Asn Arg
                565                 570                 575

Pro Ala Gln Ala Gly Ser Gly Glu Val Val Thr Leu Glu Ser Lys Val
                580                 585                 590

Ile Ile Asp Leu Tyr Arg Gln Glu Leu Leu Arg Glu Val Gln Asn Arg
            595                 600                 605

Pro Gly Tyr Arg Pro Asp Asp Arg Ile Ala Thr Phe Arg Phe Val Leu
        610                 615                 620

Glu Pro Phe Thr Ile Glu Asn Gly Leu Leu Thr Gln Thr Leu Lys Ile
625                 630                 635                 640

Arg Arg His Val Val Ser Asp Arg Tyr Arg Asp Met Ile Asn Ala Met
                645                 650                 655

Phe Glu
```

METHODS AND COMPOSITIONS FOR THE RECOMBINANT BIOSYNTHESIS OF FATTY ACIDS AND ESTERS

CROSS-REFERENCE TO RELATED APPLICATIONS

This application a divisional of U.S. patent application Ser. No. 13/243,165, filed Sep. 23, 2011, which is a continuation of U.S. patent application Ser. No. 12/876,056, filed Sep. 3, 2010, which is a continuation-in-part of international application PCT/US/2009/035937, filed Mar. 3, 2009, which claims the benefit of earlier filed U.S. Provisional Patent Application No. 61/121,532, filed Dec. 10, 2008, U.S. Provisional Patent Application No. 61/033,411 filed Mar. 3, 2008, and U.S. Provisional Application No. 61/033,402, filed Mar. 3, 2008; this application also claims priority to U.S. Provisional Application 61/353,145, filed Jun. 9, 2010. The disclosures of each of these applications are incorporated herein by reference.

REFERENCE TO SEQUENCE LISTING

The instant application contains a Sequence Listing which has been submitted via EFS-Web and is hereby incorporated by reference in its entirety. Said ASCII copy, created on Sep. 23, 2011, is named "19578_US_Sequence_Listing.txt", lists 25 sequences, and is 91.4 kb in size.

FIELD OF THE INVENTION

The present disclosure relates to methods for conferring fatty acid and fatty acid ester-producing properties to a heterotrophic or photoautotrophic host, such that the modified host can be used in the commercial production of fuels and chemicals.

BACKGROUND OF THE INVENTION

Many existing photoautotrophic organisms (i.e., plants, algae, and photosynthetic bacteria) are poorly suited for industrial bioprocessing and have therefore not demonstrated commercial viability. Such organisms typically have slow doubling times (3-72 hrs) compared to industrialized heterotrophic organisms such as *Escherichia coli* (20 minutes), reflective of low total productivities. A need exists, therefore, for engineered photosynthetic microbes which produce increased yields of fatty acids and esters.

SUMMARY OF THE INVENTION

In one embodiment, the invention provides a method for producing fatty acid esters, comprising: (i) culturing an engineered photosynthetic microorganism in a culture medium, wherein said engineered photosynthetic microorganism comprises a recombinant thioesterase, a recombinant acyl-CoA synthetase, and a recombinant wax synthase; and (ii) exposing said engineered photosynthetic microorganism to light and carbon dioxide, wherein said exposure results in the incorporation of an alcohol into a fatty acid ester produced by said engineered photosynthetic microorganism. In a related embodiment, the engineered photosynthetic microorganism is an engineered cyanobacterium. In another related embodiment, at least one of said fatty acid esters produced by the engineered cyanobacterium is selected from the group consisting of a tetradecanoic acid ester, a hexadecanoic acid ester, a heptadecanoic acid ester, a Δ9-octadecenoic acid ester, and an octadecanoic acid ester. In another related embodiment, the amount of said fatty acid esters produced by said engineered cyanobacterium is increased relative to the amount of fatty acid produced by an otherwise identical cell lacking said recombinant thioesterase, acyl-CoA synthetase or wax synthase. In certain embodiments, the incorporated alcohol is an exogenously added alcohol selected from the group consisting of methanol, ethanol, propanol, isopropanol, butanol, hexanol, cyclohexanol, and isoamyl alcohol.

In another related embodiment, the esters produce by the engineered cyanobacteria include a hexadecanoic acid ester and an octadecanoic acid ester. In another related embodiment, the amount of hexadecanoic acid ester produced is between 1.5 and 10 fold greater than the amount of octadecanoic acid ester. In yet another related embodiment, the amount of hexadecanoic acid ester produced is between 1.5 and 5 fold greater than the amount of octadecanoic acid ester produced. In yet another related embodiment, at least 50% of the esters produced by said engineered cyanobacterium are hexadecanoic acid esters. In yet another related embodiment, between 65% and 85% of the esters produced by said engineered cyanobacterium are hexadecanoic acid esters.

In a related embodiment of the method for producing fatty acid esters described above, the exogenously alcohol is butanol and fatty acidy butyl esters are produced. In yet another related embodiment, the yield of fatty acid butyl esters is at least 5% dry cell weight. In yet another related embodiment, the yield of fatty acid butyl esters is at least 10% dry cell weight. In yet another related embodiment, exogenously added butanol is present in said culture at concentrations between 0.01 and 0.2% (vol/vol). In yet another related embodiment, the concentration of exogenously added butantol is about 0.05 to 0.075% (vol/vol).

In another related embodiment of the method for producing fatty acid esters described above, the exogenously added alcohol is ethanol. In yet another related embodiment, the yield of ethyl esters is at least 1% dry cell weight.

In another related embodiment of the method for producing fatty acid esters described above, the exogenously added alcohol is methanol. In yet another related embodiment, the yield of methyl esters is at least 0.01% dry cell weight.

In another related embodiment, said engineered cyanobacterium further comprises a recombinant resistance nodulation cell division type ("RND-type") transporter, e.g., a TolC-AcrAB transporter. In another related embodiment, the expression of TolC is controlled by a promoter separate from the promoter that controls expression of AcrAB. In another related embodiment, the genes encoding the recombinant transporter are encoded by a plasmid. In another related embodiment, the fatty acid esters are secreted into the culture medium at increased levels relative to an otherwise identical cyanobacterium lacking the recombinant transporter.

In certain embodiments of the methods for producing fatty acid esters described above, the recombinant thioesterase, wax synthase, and acyl-CoA synthetase are expressed as an operon under the control of a single promoter. In certain embodiments, the single promoter is an inducible promoter. In other embodiments of the methods described above, the expression of at least two of the genes selected from the group consisting of a recombinant thioesterase, wax synthase, and acyl-CoA synthetase is under the control of different promoters. One or more of the promoters can be an inducible promoter. In related embodiments, at least one of said recombinant genes is encoded on a plasmid. In yet other related embodiments, at least one of said recombinant genes is integrated into the chromosome of the engineered cyanobacteria. In yet other related embodiments, at least one of said recombinant genes is a gene that is native to the engineered cyanobacteria, but whose expression is controlled by a recombinant promoter. In yet other related embodiments, one or more promoters are selected from the group consisting of a cI promoter, a cpcB promoter, a lacI-Ptrc promoter, an EM7 promoter, an PaphII promoter, a NirA-type promoter, a PnrsA promoter, or a PnrsB promoter.

In another embodiment, the invention provides a method for producing fatty acid esters, comprising: (i) culturing an engineered cyanobacterium in a culture medium, wherein said engineered cyanobacterium comprises a recombinant acyl-CoA synthetase and a recombinant wax synthase; and (ii) exposing said engineered cyanobacterium to light and carbon dioxide, wherein said exposure results in the conversion of an alcohol by said engineered cynanobacterium into fatty acid esters, wherein at least one of said fatty acid esters is selected from the group consisting of a tetradecanoic acid ester, a hexadecanoic acid ester, a heptadecanoic acid ester, a Δ9-octadecenoic acid ester, and an octadecanoic acid ester, wherein the amount of said fatty acid esters produced by said engineered cyanobacterium is increased relative to the amount of fatty acid produced by an otherwise identical cell lacking said recombinant acyl-CoA synthetase or wax synthase. In a related embodiment, the alcohol is an exogenously added alcohol selected from the group consisting of methanol, ethanol, propanol, isopropanol, butanol, hexanol, cyclohexanol, and isoamyl alcohol.

In another embodiment, the invention provides a method for producing a fatty acid ester, comprising: (i) culturing an engineered cyanobacterium in a culture medium, wherein said engineered cyanobacterium comprises a recombinant RND-type transporter; and (ii) exposing said engineered cyanobacterium to light and carbon dioxide, wherein said exposure results in the production of a fatty acid ester by said engineered cyanobacterium, and wherein said RND-type transporter secretes said fatty acid ester into said culture medium. In a related embodiment, said RND-type transporter is a TolC-AcrAB transporter.

In an embodiment related to the methods described above, the invention further comprises isolating said fatty acid ester from said engineered cyanobacterium or said culture medium.

In another embodiment, the invention also provides an engineered cyanobacterium, wherein said cyanobacterium comprises a recombinant thioesterase, a recombinant acyl-CoA synthetase, and a recombinant wax synthase. In certain embodiments, the engineered cyanobacterium additionally comprises a recombinant RND-type transporter, e.g., a TolC-AcrAB transporter.

In a related embodiment, at least one of said recombinant enzymes is heterologous with respect to said engineered cyanobacterium. In another embodiment, said cyanobacterium does not synthesize fatty acid esters in the absence of the expression of one or both of the recombinant enzymes. In another embodiment, at least one of said recombinant enzymes is not heterologous to said engineered cyanobacterium.

In yet another related embodiment, the recombinant thioesterase, acyl-CoA synthetase and wax synthase are selected from the enzymes listed in Table 3A, Table 3B and Table 3C, respectively. In yet another related embodiment, the recombinant thioesterase has an amino acid sequence that is identical to SEQ ID NO: 1. In yet another related embodiment, the recombinant thioesterase has an amino acid sequence that is at least 90%, at least 95%, at least 96%, at least 97%, at least 98%, or at least 99% identical to SEQ ID NO: 1. In yet another related embodiment, the recombinant acyl-CoA synthetase is identical to SEQ ID NO:2. In yet another related embodiment, the recombinant acyl-CoA synthetase has an amino acid sequence at least 90%, at least 95%, at least 96%, at least 97%, at least 98%, or at least 99% identical to SEQ ID NO: 2. In yet another related embodiment, recombinant wax synthase is identical to SEQ ID NO: 3. In yet another related embodiment, the recombinant wax synthase has an amino acid sequence is at least 90%, at least 95%, at least 96%, at least 97%, at least 98%, or at least 99% identical to SEQ ID NO: 3. In yet another related embodiment, the recombinant TolC transporter amino acid sequence is identical to SEQ ID NO: 7. In yet another related embodiment, the recombinant TolC transporter has an amino acid sequence at least 90%, at least 95%, at least 96%, at least 97%, at least 98%, or at least 99% identical to SEQ ID NO: 7. In yet another related embodiment, the recombinant AcrA amino acid sequence is identical to SEQ ID NO: 8. In yet another related embodiment, the recombinant AcrA amino acid sequence is at least 90%, at least 95%, at least 96%, at least 97%, at least 98%, or at least 99% identical to SEQ ID NO: 8. In yet another related embodiment, the recombinant AcrB amino acid sequence is identical to SEQ ID NO: 9. In yet another related embodiment, the recombinant AcrB amino acid sequence is at least 90%, at least 95%, at least 96%, at least 97%, at least 98%, or at least 99% identical to SEQ ID NO: 9.

In related embodiments of the above-described embodiments, an engineered photosynthetic microorganism other than a cyanobacterium can be used. In other related embodiments, a thermophilic cyanobacterium can be used.

In another embodiment, the invention provides a methods and compositions for producing fatty acids using an engineered photosynthetic microorganism. For example, in one embodiment, the invention provides a method for producing fatty acids, comprising: (a) culturing an engineered photosynthetic microorganism, wherein said engineered photosynthetic microorganism comprises a modification which reduces the expression of said microorganism's endogenous acyl-ACP synthetase; and (b) exposing said engineered photosynthetic microorganism to light and carbon dioxide, wherein said exposure results in the production of fatty acids by said engineered cyanobacterium, wherein the amount of fatty acids produced is increased relative to the amount of fatty acids produced by an otherwise identical microorganism lacking said modification. In a related embodiment, the engineered microorganism is a thermophile. In another related embodiment, the engineered microorganism is a cyanobacterium. In yet another related embodiment, the engineered microorganism is a thermophilic cyanobacterium. In yet another related embodiment, the engineered microorganism is *Thermosynechococcus elongatus* BP-1. In yet another related embodiment of the method for producing fatty acids, the modification is a knock-out or deletion of the gene encoding said endogenous acyl-ACP synthetase. In yet another related embodiment, the gene encoding said acyl-ACP synthetase is the acyl-ACP synthetase or aas gene, e.g., GenBank accession number NP_682091.1. In yet another related embodiment, the increase in fatty acid production is at least a 2 fold increase. In yet another related embodiment, the increase in fatty acid production is between 2 and 4.5 fold. In yet another related embodiment, the increase in fatty acid production includes an increase in fatty acids secreted into a culture media. In yet another related embodiment, most of said increase in fatty acid production arises from the increased production of myristic and oleic acid. In yet another related embodiment of the method for producing fatty acids, the engineered photosynthetic microorganism further comprises a TolC-AcrAB transporter.

In another embodiment, the invention provides an engineered photosynthetic microorganism, wherein said microorganism comprises a deletion or knock-out of an endogenous gene encoding a acyl-ACP synthetase or long-chain fatty acid ligase. In a related embodiment, engineered photosynthetic microorganism is a thermophile. In yet another related embodiment, the engineered photosynthetic microorganism is a cyanobacterium or a thermophilic cyanobacterium. In yet another related embodiment, the cyanobacterium is *Thermosynechococcus elongatus* BP-1. In yet another related embodiment, the acyl-ACP synthetase is the aas gene of the thermophilic cyanobacterium, e.g., GenBank accession number NP_682091.1. In yet another related embodiment, the engineered photosynthetic microorganism further comprises a TolC-AcrAB transporter.

In yet another embodiment, the invention provides an engineered cyanbacterial strain selected from the group consisting of JCC723, JCC803, JCC1215, JCC803, JCC1132, and JCC1585. In yet another embodiment, the invention provides an engineered cyanobacterial strain selected from the group consisting of the engineered *Synechococcus* sp. PCC7002 strains JCC1648 (Δaas tesA, with tesA under control of P(nir07) on pAQ4), JCC1704 (Δaas fatB, with fatB inserted at aquI under the control of P(nir07)), JCC1705 (Δaas fatB1, with fatB1 inserted at aquI under the control of P(nir07)), JCC1706 (Δaas fatB2 with fatB2 inserted at aquI under the control of P(nir07)), JCC1751 (Δaas tesA, with tesA under control of P(nir07) on pAQ3), and JCC1755 (Δaas fatB_mat, with fatB_mat under control of P(nir07) on pAQ3). In yet another embodiment, the invention provides the engineered cyanobacterial strain JCC1862 (*Thermosynechococcus elongatus* BP-1 kan$^R$ Δaas).

These and other embodiments of the invention are further described in the Figures, Description, Examples and Claims, herein.

DETAILED DESCRIPTION OF THE INVENTION

Figure 1:
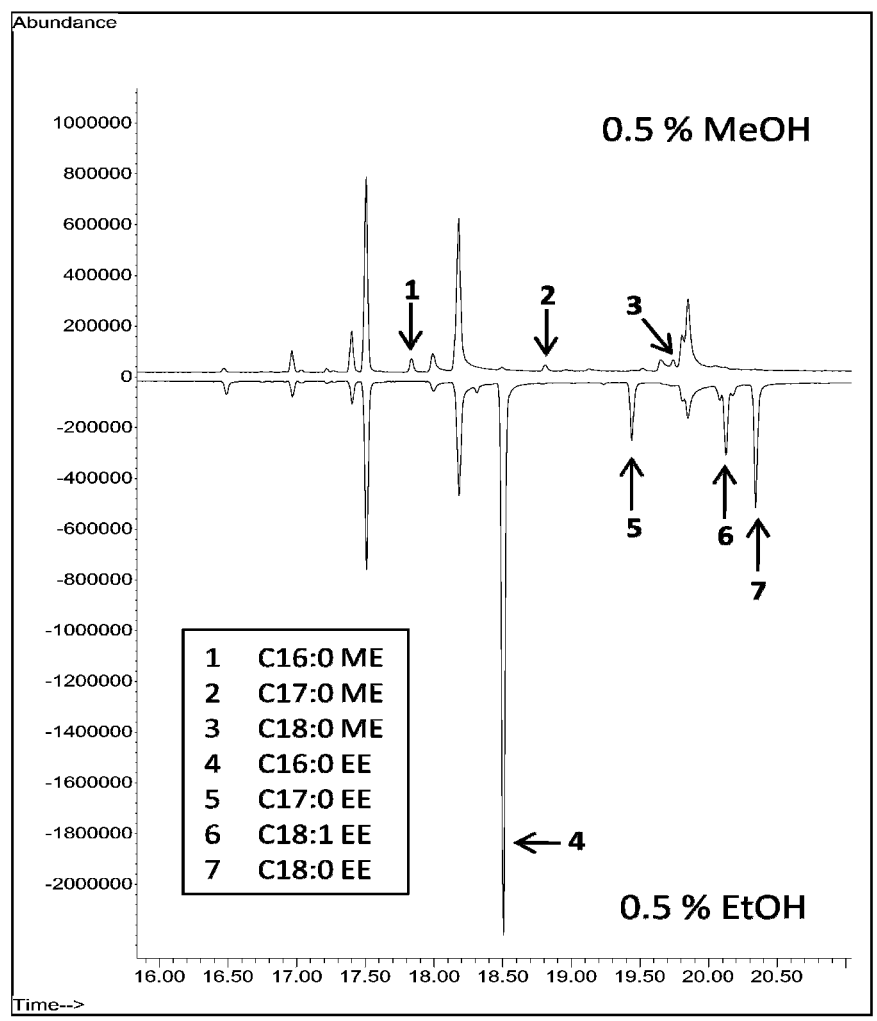
FIG. 1 depicts a GC/MS chromatogram overlay comparing cell pellet extracts of JCC803 incubated with either methanol (top trace) or ethanol (bottom traces). The peaks due to methyl esters (MEs) or ethyl esters (EEs) are labeled.

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook et al., *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); Handbook of Biochemistry: Section A Proteins, Vol II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

An "isolated" RNA, DNA or a mixed polymer is one which is substantially separated from other cellular components that naturally accompany the native polynucleotide in its natural host cell, e.g., ribosomes, polymerases and genomic sequences with which it is naturally associated.

As used herein, an "isolated" organic molecule (e.g., a fatty acid or a fatty acid ester) is one which is substantially separated from the cellular components (membrane lipids, chromosomes, proteins) of the host cell from which it originated, or from the medium in which the host cell was cultured. The term does not require that the biomolecule has been separated from all other chemicals, although certain isolated biomolecules may be purified to near homogeneity.

The term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this present invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., *Technique*, 1:11-15 (1989) and Caldwell and Joyce, *PCR Methods Applic.* 2:28-33 (1992)); and "oligonucleotide-directed mutagenesis" (a process which enables the generation of site-specific mutations in any cloned DNA segment of interest; see, e.g., Reidhaar-Olson and Sauer, *Science* 241:53-57 (1988)).

The term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

Deletion:
The removal of one or more nucleotides from a nucleic acid molecule or one or more amino acids from a protein, the regions on either side being joined together.

Knock-Out:
A gene whose level of expression or activity has been reduced to zero. In some examples, a gene is knocked-out via deletion of some or all of its coding sequence. In other examples, a gene is knocked-out via introduction of one or more nucleotides into its open reading frame, which results in translation of a non-sense or otherwise non-functional protein product.

The term "vector" as used herein is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply "expression vectors").

"Operatively linked" or "operably linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

Promoters useful for expressing the recombinant genes described herein include both constitutive and inducible/repressible promoters. Examples of inducible/repressible promoters include nickel-inducible promoters (e.g., PnrsA, PnrsB; see, e.g., Lopez-Mauy et al., *Cell* (2002) v.43:247-256, incorporated by reference herein) and urea repressible promoters such as PnirA (described in, e.g., Qi et al., *Applied and Environmental Microbiology* (2005) v.71: 5678-5684, incorporated by reference herein). In other embodiments, a PaphII and/or a lacIq-Ptrc promoter can used to control expression. Where multiple recombinant genes are expressed in an engineered cyanobacteria of the invention, the different genes can be controlled by different promoters or by identical promoters in separate operons, or the expression of two or more genes may be controlled by a single promoter as part of an operon.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}I$, $^{32}P$, $^{35}S$, and $^{3}H$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., *Current Protocols in Molecular Biology*, Greene Publishing Associates (1992, and Supplements to 2002) (hereby incorporated by reference).

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present invention have particular utility. The heterologous polypeptide included within the fusion protein of the present invention is at least 6 amino acids in length, often at least 8 amino acids in length, and usefully at least 15, 20, and 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, the term "antibody" refers to a polypeptide, at least a portion of which is encoded by at least one immunoglobulin gene, or fragment thereof, and that can bind specifically to a desired target molecule. The term includes naturally-occurring forms, as well as fragments and derivatives.

Fragments within the scope of the term "antibody" include those produced by digestion with various proteases, those produced by chemical cleavage and/or chemical dissociation and those produced recombinantly, so long as the fragment remains capable of specific binding to a target molecule. Among such fragments are Fab, Fab', Fv, F(ab').sub.2, and single chain Fv (scFv) fragments.

Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., *Intracellular Antibodies: Research and Disease Applications*, (Marasco, ed., Springer-Verlag New York, Inc., 1998), the disclosure of which is incorporated herein by reference in its entirety).

As used herein, antibodies can be produced by any known technique, including harvest from cell culture of native B lymphocytes, harvest from culture of hybridomas, recombinant expression systems and phage display.

The term "non-peptide analog" refers to a compound with properties that are analogous to those of a reference polypeptide. A non-peptide compound may also be termed a "peptide mimetic" or a "peptidomimetic." See, e.g., Jones, *Amino Acid and Peptide Synthesis*, Oxford University Press (1992); Jung, *Combinatorial Peptide and Nonpeptide Libraries: A Handbook*, John Wiley (1997); Bodanszky et al., *Peptide Chemistry—A Practical Textbook*, Springer Verlag (1993); *Synthetic Peptides: A Users Guide*, (Grant, ed., W.H. Freeman and Co., 1992); Evans et al., *J. Med. Chem.* 30:1229 (1987); Fauchere, J. Adv. Drug Res. 15:29 (1986); Veber and Freidinger, Trends Neurosci., 8:392-396 (1985); and references sited in each of the above, which are incorporated herein by reference. Such compounds are often developed with the aid of computerized molecular modeling. Peptide mimetics that are structurally similar to useful peptides of the present invention may be used to produce an equivalent effect and are therefore envisioned to be part of the present invention.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 85% overall sequence homology to its wild-type counterpart. Even more preferred are muteins having at least 90% overall sequence homology to the wild-type protein.

In an even more preferred embodiment, a mutein exhibits at least 95% sequence identity, even more preferably 98%, even more preferably 99% and even more preferably 99.9% overall sequence identity.

Sequence homology may be measured by any common sequence analysis algorithm, such as Gap or Bestfit.

Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (Golub and Gren eds., Sinauer Associates, Sunderland, Mass., 2$^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62. The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (incorporated by reference herein). For example, percent sequence identity between amino acid sequences can be determined using FASTA with its default parameters (a word size of 2 and the PAM250 scoring matrix), as provided in GCG Version 6.1, herein incorporated by reference.

"Specific binding" refers to the ability of two molecules to bind to each other in preference to binding to other molecules in the environment. Typically, "specific binding" discriminates over adventitious binding in a reaction by at least twofold, more typically by at least 10-fold, often at least 100-fold. Typically, the affinity or avidity of a specific binding reaction, as quantified by a dissociation constant, is about $10^{-7}$ M or stronger (e.g., about $10^{-8}$ M, $10^{-9}$ M or even stronger).

"Percent dry cell weight" refers to a production measurement of esters of fatty acids or fatty acids obtained as follows: a defined volume of culture is centrifuged to pellet the cells. Cells are washed then dewetted by at least one cycle of microcentrifugation and aspiration. Cell pellets are lyophilized overnight, and the tube containing the dry cell mass is weighed again such that the mass of the cell pellet can be calculated within ±0.1 mg. At the same time cells are processed for dry cell weight determination, a second sample of the culture in question is harvested, washed, and dewetted. The resulting cell pellet, corresponding to 1-3 mg of dry cell weight, is then extracted by vortexing in approximately 1 ml acetone plus butylated hydroxytolune (BHT) as antioxidant and an internal standard, e.g., ethyl arachidate. Cell debris is then pelleted by centrifugation and the supernatant (extractant) is taken for analysis by GC. For accurate quantitation of the molecules, flame ionization detection (FID) was used as opposed to MS total ion count. The concentrations of the esters or fatty acids in the biological extracts were calculated using calibration relationships between GC-FID peak area and known concentrations of authentic standards. Knowing the volume of the extractant, the resulting concentrations of the products in the extractant, and the dry cell weight of the cell pellet extracted, the percentage of dry cell weight that comprised the esters or fatty acids can be determined.

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

"Carbon-based Products of Interest" include alcohols such as ethanol, propanol, isopropanol, butanol, fatty alcohols, fatty acid esters, wax esters; hydrocarbons and alkanes such as propane, octane, diesel, Jet Propellant 8 (JP8); polymers such as terephthalate, 1,3-propanediol, 1,4-butanediol, polyols, Polyhydroxyalkanoates (PHA), poly-beta-hydroxybutyrate (PHB), acrylate, adipic acid, ε-caprolactone, isoprene, caprolactam, rubber; commodity chemicals such as lactate, Docosahexaenoic acid (DHA), 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxypropionic acid (HPA), lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; pharmaceuticals and pharmaceutical intermediates such as 7-aminodeacetoxycephalosporanic acid (7-ADCA)/cephalosporin, erythromycin, polyketides, statins, paclitaxel, docetaxel, terpenes, peptides, steroids, omega fatty acids and other such suitable products of interest. Such products are useful in the context of biofuels, industrial and specialty chemicals, as intermediates used to make additional products, such as nutritional supplements, neutraceuticals, polymers, paraffin replacements, personal care products and pharmaceuticals.

Biofuel:

A biofuel refers to any fuel that derives from a biological source. Biofuel can refer to one or more hydrocarbons, one or more alcohols, one or more fatty esters or a mixture thereof.

The term "hydrocarbon" generally refers to a chemical compound that consists of the elements carbon (C), hydrogen (H) and optionally oxygen (O). There are essentially three types of hydrocarbons, e.g., aromatic hydrocarbons, saturated hydrocarbons and unsaturated hydrocarbons such as alkenes, alkynes, and dienes. The term also includes fuels, biofuels, plastics, waxes, solvents and oils. Hydrocarbons encompass biofuels, as well as plastics, waxes, solvents and oils. A "fatty acid" is a carboxylic acid with a long unbranched aliphatic tail (chain), which is either saturated or unsaturated. Most naturally occurring fatty acids have a chain of four to 28 carbons.

Unless otherwise defined, all technical and scientific terms used herein have the same meaning as commonly understood by one of ordinary skill in the art to which this present invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

Nucleic Acid Sequences

Esters are chemical compounds with the basic formula:

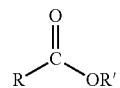

where R and R' denote any alkyl or aryl group. In one embodiment, the invention provides one or more isolated or recombinant nucleic acids encoding one or more genes which, when recombinantly expressed in a photosynthetic microorganism, catalyze the synthesis of esters by the microorganism. The first gene is a thioesterase, which catalyzes the synthesis of fatty acids from an acyl-Acyl Carrier Protein ("acyl-ACP") molecule. The second gene is an acyl-CoA synthetase, which synthesizes fatty acyl-CoA from a fatty acid. The third gene is a wax synthase, which synthesizes esters from a fatty acyl-CoA molecule and an alcohol (e.g., methanol, ethanol, proponal, butanol, etc.). In certain related embodiments, additional genes expressing a recombinant resistance nodulation cell division type ("RND-type") transporter such as TolC/AcrAB are also recombinantly expressed to facilitate the transport of ethyl esters outside of the engineered photosynthetic cell and into the culture medium.

Accordingly, the present invention provides isolated nucleic acid molecules for genes encoding thioesterase, acyl-CoA synthetases and wax synthase enzymes, and variants thereof. An exemplary full-length expression optimized nucleic acid sequence for a gene encoding a thioesterase is presented as SEQ ID NO: 4. The corresponding amino acid sequences is presented as SEQ ID NO: 1. Additional genes encoding thioesterases are presented in Table 3A. An exemplary full-length expression-optimized nucleic acid sequence for a gene encoding an acyl-CoA synthetase is presented as SEQ ID NO: 5, and the corresponding amino acid sequence is presented as SEQ ID NOs: 2. Additional genes encoding acyl-CoA synthetases are presented in Table 3B. An exemplary full-length expression-optimized nucleic acid sequence for a gene encoding an acyl-CoA synthetase is presented as SEQ ID NO: 6, and the corresponding amino acid sequence is presented as SEQ ID NOs: 3. Additional genes encoding acyl-CoA synthetases are presented in Table 3C.

One skilled in the art will recognize that the redundancy of the genetic code will allow many other nucleic acid sequences to encode the identical enzymes. The sequences of the nucleic acids disclosed herein can be optimized as needed to yield the desired expression levels in a particular photosynthetic microorganism. Such a nucleic acid sequence can have 70%, 75%, 80%, 85%, 90%, 95%, 98%, 99%, 99.9% or even higher identity to the native gene sequence.

In another embodiment, the nucleic acid molecule of the present invention encodes a polypeptide having the amino acid sequence of SEQ ID NO:1, 2, 3, 7, 8, or 9. Preferably, the nucleic acid molecule of the present invention encodes a polypeptide sequence of at least 50%, 60, 70%, 80%, 85%, 90% or 95% identity to SEQ ID NO:1, 2, 3, 7, 8 or 9 and the identity can even more preferably be 96%, 97%, 98%, 99%, 99.9% or even higher.

The present invention also provides nucleic acid molecules that hybridize under stringent conditions to the above-described nucleic acid molecules. As defined above, and as is well known in the art, stringent hybridizations are performed at about 25° C. below the thermal melting point ($T_m$) for the specific DNA hybrid under a particular set of conditions, where the $T_m$ is the temperature at which 50% of the target sequence hybridizes to a perfectly matched probe. Stringent washing is performed at temperatures about 5° C. lower than the $T_m$ for the specific DNA hybrid under a particular set of conditions.

Nucleic acid molecules comprising a fragment of any one of the above-described nucleic acid sequences are also provided. These fragments preferably contain at least 20 contiguous nucleotides. More preferably the fragments of the nucleic acid sequences contain at least 25, 30, 35, 40, 45, 50, 60, 70, 80, 90, 100 or even more contiguous nucleotides.

The nucleic acid sequence fragments of the present invention display utility in a variety of systems and methods. For example, the fragments may be used as probes in various hybridization techniques. Depending on the method, the target nucleic acid sequences may be either DNA or RNA. The target nucleic acid sequences may be fractionated (e.g., by gel electrophoresis) prior to the hybridization, or the hybridization may be performed on samples in situ. One of skill in the art will appreciate that nucleic acid probes of known sequence find utility in determining chromosomal structure (e.g., by Southern blotting) and in measuring gene expression (e.g., by Northern blotting). In such experiments, the sequence fragments are preferably detectably labeled, so that their specific hybridization to target sequences can be detected and optionally quantified. One of skill in the art will appreciate that the nucleic acid fragments of the present invention may be used in a wide variety of blotting techniques not specifically described herein.

It should also be appreciated that the nucleic acid sequence fragments disclosed herein also find utility as probes when immobilized on microarrays. Methods for creating microarrays by deposition and fixation of nucleic acids onto support substrates are well known in the art. Reviewed in *DNA Microarrays: A Practical Approach* (Practical Approach Series), Schena (ed.), Oxford University Press (1999) (ISBN: 0199637768); Nature Genet. 21(1)(suppl):1-60 (1999); *Microarray Biochip: Tools and Technology*, Schena (ed.), Eaton Publishing Company/BioTechniques Books Division (2000) (ISBN: 1881299376), the disclosures of which are incorporated herein by reference in their entireties. Analysis of, for example, gene expression using microarrays comprising nucleic acid sequence fragments, such as the nucleic acid sequence fragments disclosed herein, is a well-established utility for sequence fragments in the field of cell and molecular biology. Other uses for sequence fragments immobilized on microarrays are described in Gerhold et al., *Trends Biochem. Sci.* 24:168-173 (1999) and Zweiger, *Trends Biotechnol.* 17:429-436 (1999); *DNA Microarrays: A Practical Approach* (Practical Approach Series), Schena (ed.), Oxford University Press (1999) (ISBN: 0199637768); Nature Genet. 21(1)(suppl):1-60 (1999); *Microarray Biochip: Tools and Technology*, Schena (ed.), Eaton Publishing Company/BioTechniques Books Division (2000) (ISBN: 1881299376), the disclosure of each of which is incorporated herein by reference in its entirety.

As is well known in the art, enzyme activities can be measured in various ways. For example, the pyrophosphorolysis of OMP may be followed spectroscopically (Grubmeyer et al., (1993) *J. Biol. Chem.* 268:20299-20304). Alternatively, the activity of the enzyme can be followed using chromatographic techniques, such as by high performance liquid chromatography (Chung and Sloan, (1986) *J. Chromatogr.* 371:71-81). As another alternative the activity can be indirectly measured by determining the levels of product made from the enzyme activity. These levels can be measured with techniques including aqueous chloroform/methanol extraction as known and described in the art (Cf M. Kates (1986) *Techniques of Lipidology; Isolation, analysis and identification of Lipids.* Elsevier Science Publishers, New York (ISBN: 0444807322)). More modern techniques include using gas chromatography linked to mass spectrometry (Niessen, W. M. A. (2001). *Current practice of gas chromatography—mass spectrometry.* New York, N.Y.: Marcel Dekker. (ISBN: 0824704738)). Additional modern techniques for identification of recombinant protein activity and products including liquid chromatography-mass spectrometry (LCMS), high performance liquid chromatography (HPLC), capillary electrophoresis, Matrix-Assisted Laser Desorption Ionization time of flight-mass spectrometry (MALDI-TOF MS), nuclear magnetic resonance (NMR), near-infrared (NIR) spectroscopy, viscometry (Knothe, G (1997) *Am. Chem. Soc. Symp. Series,* 666: 172-208), titration for determining free fatty acids (Komers (1997) *Fett/Lipid,* 99(2): 52-54), enzymatic methods (Bailer (1991) *Fresenius J. Anal. Chem.* 340(3): 186), physical property-based methods, wet chemical methods, etc. can be used to analyze the levels and the identity of the product produced by the organisms of the present invention. Other methods and techniques may also be suitable for the measurement of enzyme activity, as would be known by one of skill in the art.

Vectors

Also provided are vectors, including expression vectors, which comprise the above nucleic acid molecules of the present invention, as described further herein. In a first embodiment, the vectors include the isolated nucleic acid molecules described above. In an alternative embodiment, the vectors of the present invention include the above-described nucleic acid molecules operably linked to one or more expression control sequences. The vectors of the instant invention may thus be used to express a thioesterase, an acyl-CoA synthease, and/or a wax synthase, contributing to the synthesis of esters by the cell.

In a related embodiment, vectors may include nucleic acid molecules encoding an RND-type transporter such as TolC/AcrAB to facilitate the extracellular transport of esters. Exemplary vectors of the invention include any of the vectors expressing a thioesterase, an acyl-CoA synthease, wax synthase, and/or TolC/AcrAB transporter disclosed here, e.g., pJB532, pJB634, pJB578 and pJB1074. The invention also provides other vectors such as pJB161 which are capable of receiving nucleic acid sequences of the invention. Vectors such as pJB161 comprise sequences which are homologous with sequences that are present in plasmids which are endogenous to certain photosynthetic microorganisms (e.g., plasmids pAQ7 or pAQ1 of certain *Synechococcus* species). Recombination between pJB161 and the endogenous plasmids in vivo yield engineered microbes expressing the genes of interest from their endogenous plasmids. Alternatively, vectors can be engineered to recombine with the host cell chromosome, or the vector can be engineered to replicate and express genes of interest independent of the host cell chromosome or any of the host cell's endogenous plasmids.

Vectors useful for expression of nucleic acids in prokaryotes are well known in the art.

Isolated Polypeptides

According to another aspect of the present invention, isolated polypeptides (including muteins, allelic variants, fragments, derivatives, and analogs) encoded by the nucleic acid molecules of the present invention are provided. In one embodiment, the isolated polypeptide comprises the polypeptide sequence corresponding to SEQ ID NO:1, 2, 3, 7, 8, or 9. In an alternative embodiment of the present invention, the isolated polypeptide comprises a polypeptide sequence at least 85% identical to SEQ ID NO:1, 2, 3, 7, 8, or 9. Preferably the isolated polypeptide of the present invention has at least 50%, 60, 70%, 80%, 85%, 90%, 95%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or even higher identity to SEQ ID NO:1, 2, 3, 7, 8 or 9.

According to other embodiments of the present invention, isolated polypeptides comprising a fragment of the above-described polypeptide sequences are provided. These fragments preferably include at least 20 contiguous amino acids, more preferably at least 25, 30, 35, 40, 45, 50, 60, 70, 80, 90, 100 or even more contiguous amino acids.

The polypeptides of the present invention also include fusions between the above-described polypeptide sequences and heterologous polypeptides. The heterologous sequences can, for example, include sequences designed to facilitate purification, e.g. histidine tags, and/or visualization of recombinantly-expressed proteins. Other non-limiting examples of protein fusions include those that permit display of the encoded protein on the surface of a phage or a cell, fusions to intrinsically fluorescent proteins, such as green fluorescent protein (GFP), and fusions to the IgG Fc region.

Host Cell Transformants

In another aspect of the present invention, host cells transformed with the nucleic acid molecules or vectors of the present invention, and descendants thereof, are provided. In some embodiments of the present invention, these cells carry the nucleic acid sequences of the present invention on vectors, which may but need not be freely replicating vectors. In other embodiments of the present invention, the nucleic acids have been integrated into the genome of the host cells and/or into an endogenous plasmid of the host cells.

In a preferred embodiment, the host cell comprises one or more recombinant thioesterase-, acyl-CoA synthase-, wax synthase-, or TolC/AcrAB-encoding nucleic acids which express thioesterase-, acyl-CoA synthase, wax synthase or TolC/AcrAB respectively in the host cell.

In an alternative embodiment, the host cells of the present invention can be mutated by recombination with a disruption, deletion or mutation of the isolated nucleic acid of the present invention so that the activity of a native thioesterase, acyl-CoA synthase, wax synthase, and/or TolC/AcrAB protein in the host cell is reduced or eliminated compared to a host cell lacking the mutation.

Selected or Engineered Microorganisms for the Production of Fatty Acids, Esters, and Other Carbon-Based Products of Interest Microorganism:

Includes prokaryotic and eukaryotic microbial species from the Domains *Archaea, Bacteria* and *Eucarya*, the latter including yeast and filamentous fungi, protozoa, algae, or higher Protista. The terms "microbial cells" and "microbes" are used interchangeably with the term microorganism.

A variety of host organisms can be transformed to produce a product of interest. Photoautotrophic organisms include eukaryotic plants and algae, as well as prokaryotic cyanobacteria, green-sulfur bacteria, green non-sulfur bacteria, purple sulfur bacteria, and purple non-sulfur bacteria.

Extremophiles are also contemplated as suitable organisms. Such organisms withstand various environmental parameters such as temperature, radiation, pressure, gravity, vacuum, desiccation, salinity, pH, oxygen tension, and chemicals. They include hyperthermophiles, which grow at or above 80° C. such as *Pyrolobus fumarii*; thermophiles, which grow between 60-80° C. such as *Synechococcus lividis*; mesophiles, which grow between 15-60° C. and psychrophiles, which grow at or below 15° C. such as *Psychrobacter* and some insects. Radiation tolerant organisms include *Deinococcus radiodurans*. Pressure-tolerant organisms include piezophiles, which tolerate pressure of 130 MPa. Weight-tolerant organisms include barophiles. Hypergravity (e.g., >1 g) hypogravity (e.g., <1 g) tolerant organisms are also contemplated. Vacuum tolerant organisms include tardigrades, insects, microbes and seeds. Dessicant tolerant and anhydrobiotic organisms include xerophiles such as *Artemia salina*; nematodes, microbes, fungi and lichens. Salt-tolerant organisms include halophiles (e.g., 2-5 M NaCl) *Halobacteriacea* and *Dunaliella salina*. pH-tolerant organisms include alkaliphiles such as *Natronobacterium, Bacillus firmus* OF4,

*Spirulina* spp. (e.g., pH>9) and acidophiles such as *Cyanidium caldarium, Ferroplasma* sp. (e.g., low pH). Anaerobes, which cannot tolerate $O_2$ such as *Methanococcus jannaschii*; microaerophils, which tolerate some $O_2$ such as *Clostridium* and aerobes, which require $O_2$ are also contemplated. Gas-tolerant organisms, which tolerate pure $CO_2$ include *Cyanidium caldarium* and metal tolerant organisms include metalotolerants such as *Ferroplasma acidarmanus* (e.g., Cu, As, Cd, Zn), *Ralstonia* sp. CH34 (e.g., Zn, Co, Cd, Hg, Pb). Gross, Michael. *Life on the Edge: Amazing Creatures Thriving in Extreme Environments.* New York: Plenum (1998) and Seckbach, J. "Search for Life in the Universe with Terrestrial Microbes Which Thrive Under Extreme Conditions." In Cristiano Batalli Cosmovici, Stuart Bowyer, and Dan Wertheimer, eds., *Astronomical and Biochemical Origins and the Search for Life in the Universe*, p. 511. Milan: Editrice Compositori (1997).

Plants include but are not limited to the following genera: *Arabidopsis, Beta, Glycine, Jatropha, Miscanthus, Panicum, Phalaris, Populus, Saccharum, Salix, Simmondsia* and *Zea*.

Algae and cyanobacteria include but are not limited to the following genera: *Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium, Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochloro-

*thrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis,* and *Zygonium.*

Additional cyanobacteria include members of the genus *Chamaesiphon, Chroococcus, Cyanobacterium, Cyanobium, Cyanothece, Dactylococcopsis, Gloeobacter, Gloeocapsa, Gloeothece, Microcystis, Prochlorococcus, Prochloron, Synechococcus, Synechocystis, Cyanocystis, Dermocarpella, Stanieria, Xenococcus, Chroococcidiopsis, Myxosarcina, Arthrospira, Borzia, Crinalium, Geitlerinemia, Leptolyngbya, Limnothrix, Lyngbya, Microcoleus, Oscillatoria, Planktothrix, Prochlorothrix, Pseudanabaena, Spirulina, Starria, Symploca, Trichodesmium, Tychonema, Anabaena, Anabaenopsis, Aphanizomenon, Cyanospira, Cylindrospermopsis, Cylindrospermum, Nodularia, Nostoc, Scylonema, Calothrix, Rivularia, Tolypothrix, Chlorogloeopsis, Fischerella, Geitieria, Iyengariella, Nostochopsis, Stigonema* and *Thermosynechococcus.*

Green non-sulfur bacteria include but are not limited to the following genera: *Chloroflexus, Chloronema, Oscillochloris, Heliothrix, Herpetosiphon, Roseiflexus,* and *Thermomicrobium.*

Green sulfur bacteria include but are not limited to the following genera:
*Chlorobium, Clathrochloris,* and *Prosthecochloris.*

Purple sulfur bacteria include but are not limited to the following genera: *Allochromatium, Chromatium, Halochromatium, Isochromatium, Marichromatium, Rhodovulum, Thermochromatium, Thiocapsa, Thiorhodococcus,* and *Thiocystis,*

Purple non-sulfur bacteria include but are not limited to the following genera: *Phaeospirillum, Rhodobaca, Rhodobacter, Rhodomicrobium, Rhodopila, Rhodopseudomonas, Rhodothalassium, Rhodospirillum, Rodovibrio,* and *Roseospira.*

Aerobic chemolithotrophic bacteria include but are not limited to nitrifying bacteria such as *Nitrobacteraceae* sp., *Nitrobacter* sp., *Nitrospina* sp., *Nitrococcus* sp., *Nitrospira* sp., *Nitrosomonas* sp., *Nitrosococcus* sp., *Nitrosospira* sp., *Nitrosolobus* sp., *Nitrosovibrio* sp.; colorless sulfur bacteria such as, *Thiovulum* sp., *Thiobacillus* sp., *Thiomicrospira* sp., *Thiosphaera* sp., *Thermothrix* sp.; obligately chemolithotrophic hydrogen bacteria such as *Hydrogenobacter* sp., iron and manganese-oxidizing and/or depositing bacteria such as *Siderococcus* sp., and magnetotactic bacteria such as *Aquaspirillum* sp.

Archaeobacteria include but are not limited to methanogenic archaeobacteria such as *Methanobacterium* sp., *Methanobrevibacter* sp., *Methanothermus* sp., *Methanococcus* sp., *Methanomicrobium* sp., *Methanospirillum* sp., *Methanogenium* sp., *Methanosarcina* sp., *Methanolobus* sp., *Methanothrix* sp., *Methanococcoides* sp., *Methanoplanus* sp.; extremely thermophilic S-Metabolizers such as *Thermoproteus* sp., *Pyrodictium* sp., *Sulfolobus* sp., *Acidianus* sp. and other microorganisms such as, *Bacillus subtilis, Saccharomyces cerevisiae, Streptomyces* sp., *Ralstonia* sp., *Rhodococcus* sp., *Corynebacteria* sp., *Brevibacteria* sp., *Mycobacteria* sp., and oleaginous yeast.

Preferred organisms for the manufacture of esters according to the methods disclosed herein include: *Arabidopsis thaliana, Panicum virgatum, Miscanthus giganteus,* and *Zea mays* (plants); *Botryococcus braunii, Chlamydomonas reinhardtii* and *Dunaliela salina* (algae); *Synechococcus* sp PCC 7002, *Synechococcus* sp. PCC 7942, *Synechocystis* sp. PCC 6803, *Thermosynechococcus elongatus* BP-1 (cyanobacteria); *Chlorobium tepidum* (green sulfur bacteria), *Chloroflexus auranticus* (green non-sulfur bacteria); *Chromatium tepidum* and *Chromatium vinosum* (purple sulfur bacteria); *Rhodospirillum rubrum, Rhodobacter capsulatus,* and *Rhodopseudomonas palusris* (purple non-sulfur bacteria).

Yet other suitable organisms include synthetic cells or cells produced by synthetic genomes as described in Venter et al. US Pat. Pub. No. 2007/0264688, and cell-like systems or synthetic cells as described in Glass et al. US Pat. Pub. No. 2007/0269862.

Still, other suitable organisms include microorganisms that can be engineered to fix carbon dioxide, such as *Escherichia coli, Acetobacter aceti, Bacillus subtilis,* yeast and fungi such as *Clostridium ljungdahlii, Clostridium thermocellum, Penicillium chrysogenum, Pichia pastoris, Saccharomyces cerevisiae, Schizosaccharomyces pombe, Pseudomonas fluorescens,* or *Zymomonas mobilis.*

The capability to use carbon dioxide as the sole source of cell carbon (autotrophy) is found in almost all major groups of prokaryotes. The $CO_2$ fixation pathways differ between groups, and there is no clear distribution pattern of the four presently-known autotrophic pathways. See, e.g., Fuchs, G. 1989. *Alternative pathways of autotrophic $CO_2$ fixation,* p. 365-382, in H. G. Schlegel, and B. Bowien (ed.), *Autotrophic bacteria.* Springer-Verlag, Berlin, Germany. The reductive pentose phosphate cycle (Calvin-Bassham-Benson cycle) represents the $CO_2$ fixation pathway in almost all aerobic autotrophic bacteria, for example, the cyanobacteria.

For producing esters via the recombinant expression of thioesterase, acyl-CoA synthetase and/or wax synthase enzymes, an engineered cyanobacteria, e.g., a *Synechococcus* or *Thermosynechococcus* species, is especially preferred. Other preferred organisms include *Synechocystis, Klebsiella*

*oxytoca, Escherichia coli* or *Saccharomyces cerevisiae*. Other prokaryotic, archaea and eukaryotic host cells are also encompassed within the scope of the present invention. Engineered ester-producing organisms expressing thioesterase, acyl-CoA synthetase and/or wax synthase enzymes can be further engineered to express recombinant TolC/AcrAB to enhance the extracellular transport of esters.

Carbon-Based Products of Interest: Esters

In various embodiments of the invention, desired esters or a mixture thereof can be produced. For example, by including a particular alcohol or mixture of alcohols in the culture media, methyl esters, ethyl esters, propyl esters, butyl esters, and esters of higher chain length alcohols (or mixtures thereof, depending on the substrate alcohols available to the photosynthetic microbe) can be synthesized. The carbon chain lengths of the esters can vary from $C_{10}$ to $C_{20}$, e.g., using ethanol as a substrate, diverse esters including, e.g., ethyl myristate, ethyl palmitate, ethyl oleate, and/or ethyl stearate and/or mixtures thereof can be produced by a single engineered photosynthetic microorganism of the invention. Accordingly, the invention provides methods and compositions for the production of various chain lengths of esters, each of which is suitable for use as a fuel or any other chemical use.

In preferred aspects, the methods provide culturing host cells for direct product secretion for easy recovery without the need to extract biomass. These carbon-based products of interest are secreted directly into the medium. Since the invention enables production of various defined chain length of hydrocarbons and alcohols, the secreted products are easily recovered or separated. The products of the invention, therefore, can be used directly or used with minimal processing.

Media and Culture Conditions

One skilled in the art will recognize that a variety of media and culture conditions can be used in conjunction with the methods and engineered cyanobacteria disclosed herein for the bioproduction of fatty acid esters (see, e.g., Rogers and Gallon, *Biochemistry of the Algae and Cyanobacteria*, Clarendon Press Oxford (1988); Burlwe, *Algal Culture: From Laboratory to Pilot Plant*, Carnegie Institution of Washington Publication 600 Washington, D.C., (1961); and Round, F. E. The Biology of the Algae. St Martin's Press, New York, 1965; Golden S S et al. (1987) *Methods Enzymol* 153:215-231; Golden and Sherman, *J. Bacteriology* 158:36 (1984), each of which is incorporated herein by reference). Exemplary culture conditions and media are also described in, e.g., WO/2010/068288, filed May 21, 2009, published Jun. 17, 2010, and incorporated by reference herein. Typical culture conditions for the methods of the present invention include the use of JB 2.1 culture media or A+ media. A recipe for one liter of JB 2.1 appears in Table A, below.

TABLE A

| JB 2.1 media (1 L) | | | | | |
|---|---|---|---|---|---|
| Chemical | mg/L added | FW | Molarity | Units | Source |
| NaCl | 18000 | 58.44 | 308 | mM | Fisher |
| KCl | 600 | 74.55 | 8.05 | mM | Fisher |
| NaNO$_3$ | 4000 | 84.99 | 47.06 | mM | Sigma Aldrich |
| MgSO$_4$—7H$_2$O | 5000 | 246.47 | 20.29 | mM | Sigma Aldrich |
| KH$_2$PO$_4$ | 200 | 136.09 | 1.47 | mM | Fisher |
| CaCl$_2$ | 266 | 110.99 | 2.40 | mM | Sigma |
| NaEDTA$_{tetra}$ | 30 | 372.24 | 80.59 | µM | Fisher |

TABLE A-continued

| JB 2.1 media (1 L) | | | | | |
|---|---|---|---|---|---|
| Chemical | mg/L added | FW | Molarity | Units | Source |
| Ferric Citrate | 14.1 | 244.95 | 57.48 | µM | Acros Organics |
| Tris | 1000 | 121.14 | 8.25 | mM | Fisher |
| Vitamin B$_{12}$ (Cyanocobalamin) | 0.004 | 1355.37 | 2.95E-03 | µM | Sigma Aldrich |
| H$_3$BO$_3$ | 34 | 61.83 | 554 | µM | Acros Organics |
| MnCl$_2$—4H$_2$O | 4.3 | 197.91 | 21.83 | µM | Sigma |
| ZnCl | 0.32 | 136.28 | 2.31 | µM | Sigma |
| MoO$_3$ | 0.030 | 143.94 | 0.21 | µM | Sigma Aldrich |
| CuSO$_4$—5H$_2$O | 0.0030 | 249.69 | 0.012 | µM | Sigma Aldrich |
| CoCl$_2$—6H$_2$O | 0.012 | 237.93 | 0.051 | µM | Sigma |

As described in more detail in the Examples, below, in certain embodiments one or more alcohols (e.g., methanol, ethanol, propanol, butanol, etc.) may be added during culturing to produce the desired fatty acid ester(s) of interest (e.g., a fatty acid methyl ester, a fatty acid ethyl ester, etc., and mixtures thereof). For organisms that require or metabolize most efficiently in the presence of light and carbon dioxide, either carbon dioxide or bicarbonate can be used during culturing.

Fuel Compositions

In various embodiments, compositions produced by the methods of the invention are used as fuels. Such fuels comply with ASTM standards, for instance, standard specifications for diesel fuel oils D 975-09b, and Jet A, Jet A-1 and Jet B as specified in ASTM Specification D. 1655-68. Fuel compositions may require blending of several products to produce a uniform product. The blending process is relatively straightforward, but the determination of the amount of each component to include in a blend is much more difficult. Fuel compositions may, therefore, include aromatic and/or branched hydrocarbons, for instance, 75% saturated and 25% aromatic, wherein some of the saturated hydrocarbons are branched and some are cyclic. Preferably, the methods of the invention produce an array of hydrocarbons, such as $C_{13}$-$C_{17}$ or $C_{10}$-$C_{15}$ to alter cloud point. Furthermore, the compositions may comprise fuel additives, which are used to enhance the performance of a fuel or engine. For example, fuel additives can be used to alter the freezing/gelling point, cloud point, lubricity, viscosity, oxidative stability, ignition quality, octane level, and flash point. Fuels compositions may also comprise, among others, antioxidants, static dissipater, corrosion inhibitor, icing inhibitor, biocide, metal deactivator and thermal stability improver.

In addition to many environmental advantages of the invention such as $CO_2$ conversion and renewable source, other advantages of the fuel compositions disclosed herein include low sulfur content, low emissions, being free or substantially free of alcohol and having high cetane number.

Carbon Fingerprinting

Biologically-produced carbon-based products, e.g., ethanol, fatty acids, alkanes, isoprenoids, represent a new commodity for fuels, such as alcohols, diesel and gasoline. Such biofuels have not been produced using biomass but use CO2 as its carbon source. These new fuels may be distinguishable from fuels derived form petrochemical carbon on the basis of dual carbon-isotopic fingerprinting. Such products, derivatives, and mixtures thereof may be completely distinguished from their petrochemical derived counterparts on the basis of $^{14}C$ (fM) and dual carbon-isotopic fingerprinting, indicating new compositions of matter.

There are three naturally occurring isotopes of carbon: $^{12}C$, $^{13}C$, and $^{14}C$. These isotopes occur in above-ground total carbon at fractions of 0.989, 0.011, and $10^{-12}$, respectively. The isotopes $^{12}C$ and $^{13}C$ are stable, while $^{14}C$ decays naturally to $^{14}N$, a beta particle, and an anti-neutrino in a process with a half-life of 5730 years. The isotope $^{14}C$ originates in the atmosphere, due primarily to neutron bombardment of $^{14}N$ caused ultimately by cosmic radiation. Because of its relatively short half-life (in geologic terms), $^{14}C$ occurs at extremely low levels in fossil carbon. Over the course of 1 million years without exposure to the atmosphere, just 1 part in $10^{50}$ will remain $^{14}C$.

The $^{13}C:^{12}C$ ratio varies slightly but measurably among natural carbon sources. Generally these differences are expressed as deviations from the $^{13}C:^{12}C$ ratio in a standard material. The international standard for carbon is Pee Dee Belemnite, a form of limestone found in South Carolina, with a $^{13}C$ fraction of 0.0112372. For a carbon source a, the deviation of the $^{13}C:^{12}C$ ratio from that of Pee Dee Belemnite is expressed as: $\delta_a = (R_a/R_s) - 1$, where $R_a = {}^{13}C:^{12}C$ ratio in the natural source, and $R_s = {}^{13}C:^{12}C$ ratio in Pee Dee Belemnite, the standard. For convenience, $\delta_a$ is expressed in parts per thousand, or ‰. A negative value of $\delta_a$ shows a bias toward $^{12}C$ over $^{13}C$ as compared to Pee Dee Belemnite. Table 1 shows $\delta_a$ and $^{14}C$ fraction for several natural sources of carbon.

TABLE 1

13C:12C variations in natural carbon sources

| Source | $-\delta_a$ (‰) | References |
|---|---|---|
| Underground coal | 32.5 | Farquhar et al. (1989) *Plant Mol. Biol.*, 40: 503-37 |
| Fossil fuels | 26 | Farquhar et al. (1989) *Plant Mol. Biol.*, 40: 503-37 |
| Ocean DIC* | 0-1.5 | Goericke et al. (1994) Chapter 9 in *Stable Isotopes in Ecology and Environmental Science*, by K. Lajtha and R. H. Michener, Blackwell Publishing; Ivlev (2010) *Separation Sci. Technol.* 36: 1819-1914 |
| Atmospheric CO2 | 6-8 | Ivlev (2010) *Separation Sci. Technol.* 36: 1819-1914; Farquhar et al. (1989) *Plant Mol. Biol.*, 40: 503-37 |
| Freshwater DIC* | 6-14 | Dettman et al. (1999) *Geochim. Cosmochim. Acta* 63: 1049-1057 |
| Pee Dee Belemnite | 0 | Ivlev (2010) *Separation Sci. Technol.* 36: 1819-1914 |

*DIC = dissolved inorganic carbon

Biological processes often discriminate among carbon isotopes. The natural abundance of $^{14}C$ is very small, and hence discrimination for or against $^{14}C$ is difficult to measure. Biological discrimination between $^{13}C$ and $^{12}C$, however, is well-documented. For a biological product p, we can define similar quantities to those above: $\delta_p = (R_p/R_s) - 1$, where $R_p = {}^{13}C:^{12}C$ ratio in the biological product, and $R_s = {}^{13}C:^{12}C$ ratio in Pee Dee Belemnite, the standard. Table 2 shows measured deviations in the $^{13}C:^{12}C$ ratio for some biological products.

TABLE 2

$^{13}C:^{12}C$ variations in selected biological products

| Product | $-\delta_p$(‰) | $-D$(‰)* | References |
|---|---|---|---|
| Plant sugar/starch from atmospheric $CO_2$ | 18-28 | 10-20 | Ivlev (2010) *Separation Sci. Technol.* 36: 1819-1914 |
| Cyanobacterial biomass from marine DIC | 18-31 | 16.5-31 | Goericke et al. (1994) Chapter 9 in *Stable Isotopes in Ecology and Environmental Science*, by K. Lajtha and R. H. Michener, Blackwell Publishing; Sakata et al. (1997) *Geochim. Cosmochim. Acta*, 61: 5379-89 |
| Cyanobacterial lipid from marine DIC | 39-40 | 37.5-40 | Sakata et al. (1997) *Geochim. Cosmochim. Acta*, 61: 5379-89 |
| Algal lipid from marine DIC | 17-28 | 15.5-28 | Goericke et al. (1994) Chapter 9 in *Stable Isotopes in Ecology and Environmental Science*, by K. Lajtha and R. H. Michener, Blackwell Publishing; Abelseon et al. (1961) *Proc. Natl. Acad. Sci.*, 47: 623-32 |
| Algal biomass from freshwater DIC | 17-36 | 3-30 | Marty et al. (2008) *Limnol. Oceanogr.: Methods* 6: 51-63 |
| *E. coli* lipid from plant sugar | 15-27 | near 0 | Monson et al. (1980) *J. Biol. Chem.*, 255: 11435-41 |
| Cyanobacterial lipid from fossil carbon | 63.5-66 | 37.5-40 | — |
| Cyanobacterial biomass from fossil carbon | 42.5-57 | 16.5-31 | — |

*D = discrimination by a biological process in its utilization of $^{12}C$ vs. $^{13}C$ (see text)

Table 2 introduces a new quantity, D. This is the discrimination by a biological process in its utilization of $^{12}C$ vs. $^{13}C$. We define D as follows: $D=(R_p/R_a)-1$. This quantity is very similar to $\delta_a$ and $\delta_p$, except we now compare the biological product directly to the carbon source rather than to a standard. Using D, we can combine the bias effects of a carbon source and a biological process to obtain the bias of the biological product as compared to the standard. Solving for $\delta_p$, we obtain: $\delta_p=(D)(\delta_a)+D+\delta_a$, and, because $(D)(\delta_a)$ is generally very small compared to the other terms, $\delta_p \approx \delta_a+D$.

For a biological product having a production process with a known D, we may therefore estimate $\delta_p$ by summing $\delta_a$ and D. We assume that D operates irrespective of the carbon source. This has been done in Table 1 for cyanobacterial lipid and biomass produced from fossil carbon. As shown in the Table 1 and Table 2, above, cyanobacterial products made from fossil carbon (in the form of, for example, flue gas or other emissions) will have a higher $\delta_p$ than those of comparable biological products made from other sources, distinguishing them on the basis of composition of matter from these other biological products. In addition, any product derived solely from fossil carbon will have a negligible fraction of $^{14}C$, while products made from above-ground carbon will have a $^{14}C$ fraction of approximately $10^{-12}$.

Accordingly, in certain aspects, the invention provides various carbon-based products of interest characterized as $-\delta_p(‰)$ of about 63.5 to about 66 and $-D(‰)$ of about 37.5 to about 40.

The following examples are for illustrative purposes and are not intended to limit the scope of the present invention.

Example 1

Recombinant Genes for the Biosynthesis of Biodiesel and Biodiesel-Like Compounds In one embodiment of the invention, a cyanobacterium strain is transformed or engineered to express one or more enzymes selected from the following list: a wax synthase (EC: 2.3.175), a thioesterase (EC: 3.1.2.-, 3.1.2.14), and an acyl-CoA synthase (EC:: 6.2.1.3). For example, a typical embodiment utilizes a thioesterase gene from E. coli (tesA; SEQ ID NO:1), an acyl-CoA synthetase gene from E. coli (fadD; SEQ ID NO:2), and a wax synthase gene from A. baylyi (wax; SEQ ID NO:3). Thioesterase generates fatty acid from acyl-ACP. Acyl-CoA synthetase (also referred to as acyl-CoA ligase) generates fatty acyl-CoA from fatty acid. Wax synthase (EC 2.3.1.75) generates fatty acid esters using acyl-CoA and acyl alcohol as substrates (e.g., methanol, ethanol, butanol, etc).

Additional thioesterase, acyl-CoA synthetase and wax synthases genes that can be recombinantly expressed in cyanobacteria are set forth in Table 3A, Table 3B, and Table 3C, respectively.

TABLE 3A

Exemplary Thioesterases*

| Source | Enzyme | GenBank: gene accession number | Genbank: protein accession number |
| --- | --- | --- | --- |
| E. coli | C-18:1 thioesterase | NC_000913 | NP_415027 |
| Cuphea hookeriana | C-8:0 to C-10:0 thioesterase | U39834.1 | AAC49269 |
| Umbellularia california | C-12:0 thioesterase | M94159.1 | Q41635 |
| Cinnamonum camphorum | C-14:0 thioesterase | U17076.1 | Q39473 |
| Arabidopsis thaliana | C-18:1 thioesterase | 822102 | NP_189147.1 |

*where leader sequences are present in the native protein, as in the case of E. coli tesA, the leader sequences are typically removed before the activity is recombinantly expressed

TABLE 3B

Exemplary Acyl-CoA Synthetases

| Source | Gene name | GenBank: gene accession number | Genbank: protein accession number |
| --- | --- | --- | --- |
| E. coli | Acyl-CoA synthetase | NC_000913 | NP_416319.1 |
| Geobacillus thermodenitrificans NG80-2 | Acyl-CoA synthetase | CP000557.1 | ABO66726.1 |

TABLE 3C

Exemplary Wax Synthases

| Source | Gene or protein name | GenBank: gene accession number | Genbank: protein accession number |
| --- | --- | --- | --- |
| Acinetobacter baylyi | wxs | AF529086.1 | AAO17391.1 |
| Mycobacterium tuberculosis H37Rv | acyltransferase, WS/DGAT/MGAT | | NP_218257.1 |
| Saccharomyces cerevisiae | Eeb1 | | NP_015230 |
| Saccharomyces cerevisiae | YMR210w | | NP_013937 |
| Rattus norvegicus (rat) | FAEE synthase | | P16303 |
| Fundibacter jadensis DSM 12178 | wst9 | | |
| Acinetobacter sp. H01-N | Wshn | | |
| H. sapiens | mWS | | |
| Fragaria xananassa | SAAT | | |
| Malus xdomestica | mpAAT | | |
| Simmondsia chinensis | JjWs | | Q9XGY6 |
| Mus musculus | mWS | | Q6E1M8 |

The engineered cyanobacterium expressing one or more of the thioesterase, acyl-CoA synthetase, and wax synthase genes set forth above is grown in suitable media, under appropriate conditions (e.g., temperature, shaking, light, etc.). After a certain optical density is reached, the cells are separated from the spent medium by centrifugation. The cell pellet is re-suspended and the cell suspension and the spent medium are then extracted with a suitable solvent, e.g., ethyl acetate. The resulting ethyl acetate phases from the cell suspension and the supernatant are subjected to GC-MS analysis. The fatty acid esters in the ethyl acetate phases can be quantified, e.g., using commercial palmitic acid ethyl ester as a reference standard.

Fatty acid esters can be made according to this method by adding an alcohol (e.g., methanol, propanol, isopropanol, butanol, etc.) to the fermentation media, whereby fatty acid esters of the added alcohols are produced by the engineered cyanobacterium. Alternatively, one or more alcohols can be synthesized by the engineered cyanobacterium, natively or recombinantly, and used as substrates for fatty acid ester synthesis by a recombinantly expressed wax synthase. As detailed in the Examples below, the engineered cyanobacterium can also be modified to recombinantly express a TolC/AcrAB transporter to facilitate secretion of the fatty acid esters into the culture medium.

Example 2

Synthesis of Ethyl and Methyl Fatty Acid Esters by an Engineered Cyanobacterium

Genes and Plasmids:

The pJB5 base vector was designed as an empty expression vector for recombination into *Synechococcus* sp. PCC 7002. Two regions of homology, the Upstream Homology Region (UHR) and the Downstream Homology Region (DHR), are designed to flank the construct of interest. These 500 bp regions of homology correspond to positions 3301-3800 and 3801-4300 (Genbank Accession NC_005025) for UHR and DHR respectively. The aadA promoter, gene sequence, and terminator were designed to confer spectinomycin and streptomycin resistance to the integrated construct. For expression, pJB5 was designed with the aphII kanamycin resistance cassette promoter and ribosome binding site (RBS). Downstream of this promoter and RBS, the restriction endonuclease recognition site for NdeI, EcoRI, SpeI and PacI were inserted. Following the EcoRI site, the natural terminator from the alcohol dehydrogenase gene from *Zymomonas mobilis* (adhII) terminator was included. Convenient XbaI restriction sites flank the UHR and the DHR allowing cleavage of the DNA intended for recombination from the rest of the vector.

The *E. coli* thioesterase tesA gene with the leader sequence removed (SEQ ID NO:4; Genbank #NC_000913; Chot and Cronan, 1993), the *E. coli* acyl-CoA synthetase fadD (SEQ ID NO:5; Genbank #NC_000913; Kameda and Nunn, 1981) and the wax synthase gene (wax) from *Acinetobacter baylyi* strain ADPI (SEQ ID NO:6; Genbank #AF529086.1; Stöveken et al. 2005) were purchased from DNA 2.0, following codon optimization, checking for secondary structure effects, and removal of any unwanted restriction sites (NdeI, XhoI, BamHI, NgoMIV, NcoI, Sad, BsrGI, AvrII, BmtI, MluI, EcoRI, SbfI, NotI, SpeI, XbaI, PacI, AscI, FseI). These genes were received on a pJ201 vector and assembled into a three-gene operon (tesA-fadD-wax, SEQ ID NO: 10) with flanking NdeI-EcoRI sites on the recombination vector pJB5 under the control of the PaphII kanamycin resistance cassette promoter. A second plasmid (pJB532; SEQ ID NO:11) was constructed which is identical to pJB494 except the PaphII promoter was replaced with SEQ ID NO:12, a Ptrc promoter and a lacIq repressor. As a control, a third plasmid (pJB413) was prepared with only tesA under the control of the PaphII promoter. These plasmid constructs were named pJB494, pJB532, and pJB413, respectively.

Strain Construction:

The constructs described above were integrated onto the plasmid pAQ1 in *Synechococcus* sp. PCC 7002 according to the following protocol. *Synechococcus* 7002 was grown for 48 h from colonies in an incubated shaker flask at 37° C. at 2% $CO_2$ to an $OD_{730}$ of 1 in A$^+$ medium described in Frigaard et al., *Methods Mol. Biol.*, 274:325-340 (2004). 450 µL of culture was added to a epi-tube with 50 µL of 5 µg of plasmid DNA digested with XbaI ((New England Biolabs; Ipswitch, Mass.)) that was not purified following restriction digest. Cells were incubated in the dark for four hours at 37° C. The entire volume of cells was plated on A$^+$ medium plates with 1.5% agarose and grown at 37° C. in a lighted incubator (40-60 µE/m2/s PAR, measured with a LI-250A light meter (LI-COR)) for about 24 hours. 25 µg/mL of spectinomycin was underlayed on the plates. Resistant colonies were visible in 7-10 days after further incubation, and recombinant strains were confirmed by PCR using internal and external primers to check insertion and confirm location of the genes on pAQ1 in the strains (Table 4).

TABLE 4

Joule Culture Collection (JCC) numbers of *Synechococcus* sp. PCC 7002 recombinant strains with gene insertions on the native plasmid pAQ1

| JCC # | Promoter | Genes | Marker |
|---|---|---|---|
| JCC879 | PaphII | — | aadA |
| JCC750 | PaphII | tesA | aadA |
| JCC723 | PaphII | tesA-fadD-wax | aadA |
| JCC803 | lacIq Ptrc | tesA-fadD-wax | aadA |

Ethyl Ester Production Culturing Conditions:

One colony of each of the four strains listed in Table 4 was inoculated into 10 ml of A+ media containing 50 µg/ml spectinomycin and 1% ethanol (v/v). These cultures were incubated for about 4 days in a bubble tube at 37° C. sparged at approximately 1-2 bubbles of 1% $CO_2$/air every 2 seconds in light (40-50 µE/m2/s PAR, measured with a LI-250A light meter (LI-COR)). The cultures were then diluted so that the following day they would have $OD_{730}$ of 2-6. The cells were washed with 2×10 ml JB 2.1/spec200, and inoculated into duplicate 28 ml cultures in JB 2.1/spec200+1% ethanol (v/v) media to an $OD_{730}$=0.07. IPTG was added to the JCC803 cultures to a final concentration of 0.5 mM. These cultures were incubated in a shaking incubator at 150 rpm at 37° C. under 2% $CO_2$/air and continuous light (70-130 µE m2/s PAR, measured with a LI-250A light meter (LI-COR)) for ten days. Water loss through evaporation was replaced with the addition of sterile Milli-Q water. 0.5% (v/v) ethanol was added to the cultures to replace loss due to evaporation every 48 hours. At 68 and 236 hours, 5 ml and 3 ml of culture were removed from each flask for ethyl ester analysis, respectively. The $OD_{730}$ values reached by the cultures are given in Table 5.

TABLE 5

$OD_{730}$s reached by recombinant *Synechococcus* sp. PCC 7002 strains at timepoints 68 and 236 h

| Time point | JCC879 #1 | JCC879 #2 | JCC750 #1 | JCC750 #2 | JCC723 #1 | JCC723 #2 | JCC803 #1 | JCC803 #2 |
|---|---|---|---|---|---|---|---|---|
| 68 h | 3.6 | 4.0 | 4.6 | 5.0 | 6.6 | 6.0 | 5.4 | 5.8 |
| 236 h | 21.2 | 18.5 | 19.4 | 20.9 | 22.2 | 21.4 | 17.2 | 17.7 |

The culture aliquots were pelleted using a Sorvall RC6 Plus superspeed centrifuge (Thermo Electron Corp) and a F13S-14X50CY rotor (5000 rpm for 10 min). The spent media supernatant was removed and the cells were resuspended in 1 ml of Milli-Q water. The cells were pelleted again using a benchtop centrifuge, the supernatant discarded and the cell pellet was stored at −80° C. until analyzed for the presence of ethyl esters.

Detection and Quantification of Ethyl Esters in Strains:

Cell pellets were thawed and 1 ml aliquots of acetone (Acros Organics 326570010) containing 100 mg/L butylated hydroxytoluene (Sigma-Aldrich B1378) and 50 mg/L ethyl valerate (Fluka 30784) were added. The cell pellets were mixed with the acetone using a Pasteur pipettes and vortexed twice for 10 seconds (total extraction time of 1-2 min). The suspensions were centrifuged for 5 min to pellet debris, and the supernatants were removed with Pasteur pipettes and subjected to analysis with a gas chromatograph using flame ionization detection (GC/FID).

An Agilent 7890A GC/FID equipped with a 7683 series autosampler was used to detect the ethyl esters. One μL of each sample was injected into the GC inlet (split 5:1, pressure: 20 psi, pulse time: 0.3 min, purge time: 0.2 min, purge flow: 15 mL/min) and an inlet temperature of 280° C. The column was a HP-5MS (Agilent, 30 m×0.25 mm×0.25 μm) and the carrier gas was helium at a flow of 1.0 mL/min. The GC oven temperature program was 50° C., hold one minute; 10°/min increase to 280° C.; hold ten minutes. The GC/MS interface was 290° C., and the MS range monitored was 25 to 600 amu. Ethyl myristate [C14:0; retention time (rt): 17.8 min], ethyl palmitate (C16:0; rt: 19.8 min) and ethyl stearate (C18:0; rt: 21.6 min) were identified based on comparison to a standard mix of $C_4$-$C_{24}$ even carbon saturated fatty acid ethyl esters (Supelco 49454-U). Ethyl oleate (C18:1; rt: 21.4 min) was identified by comparison with an ethyl oleate standard (Sigma Aldrich 268011). These identifications were confirmed by GC/MS (see following Methyl Ester Production description for details). Calibration curves were constructed for these ethyl esters using the commercially available standards, and the concentrations of ethyl esters present in the extracts were determined and normalized to the concentration of ethyl valerate (internal standard).

Four different ethyl esters were found in the extracts of JCC723 and JCC803 (Table 6 and Table 7). In general, JCC803 produced 2-10× the amount of each ethyl ester than JCC723, but ethyl myristate (C14:0) was only produced in low quantities of 1 mg/L or less for all these cultures. Both JCC723 and JCC803 produced ethyl esters with the relative amounts C16:0>C18:0>C18:1 (cis-9)>C14:0. No ethyl esters were found in the extracts of JCC879 or JCC750, indicating that the strain cannot make ethyl esters naturally and that expression of only the tesA gene is not sufficient to confer production of ethyl esters.

TABLE 6

Amounts of respective ethyl esters found in the cell pellet extracts of JCC723 given as mg/L of culture

| Sample | C14:0 myristate | C16:0 palmitate | C18:1 (cis-9) oleate | C18:0 stearate | % Yield* |
|---|---|---|---|---|---|
| JCC723 #1 68 h | 0.08 | 0.34 | 0.22 | 0.21 | 0.04 |
| JCC723 #2 68 h | 0.12 | 1.0 | 0.43 | 0.40 | 0.1 |
| JCC803 #1 68 h | 0.45 | 6.6 | 1.4 | 0.74 | 0.6 |
| JCC803 #2 68 h | 0.63 | 8.6 | 2.0 | 0.94 | 0.7 |
| JCC723 #1 236 h | 1.04 | 15.3 | 2.1 | 4.5 | 0.3 |

TABLE 6-continued

Amounts of respective ethyl esters found in the cell pellet extracts of JCC723 given as mg/L of culture

| Sample | C14:0 myristate | C16:0 palmitate | C18:1 (cis-9) oleate | C18:0 stearate | % Yield* |
|---|---|---|---|---|---|
| JCC723 #2 236 h | 0.59 | 9.0 | 1.3 | 3.7 | 0.2 |
| JCC803 #1 236 h | 0.28 | 35.3 | 13.4 | 19.2 | 1.3 |
| JCC803 #2 236 h | 0.49 | 49.4 | 14.9 | 21.2 | 1.6 |

*Yield (%) = ((sum of EEs)/dry cell weight) * 100

TABLE 7

% of total ethyl esters by mass

| Sample | C14:0 myristate | C16:0 palmitate | C18:1 oleate | C18:0 stearate |
|---|---|---|---|---|
| JCC723 #1 68 h | 9.4 | 40.0 | 25.9 | 24.7 |
| JCC723 #2 68 h | 6.2 | 51.3 | 22.1 | 20.5 |
| JCC803 #1 68 h | 4.9 | 71.8 | 15.2 | 8.1 |
| JCC803 #2 68 h | 5.2 | 70.7 | 16.4 | 7.7 |
| JCC723 #1 236 h | 4.5 | 66.7 | 9.2 | 19.6 |
| JCC723 #2 236 h | 4.0 | 61.7 | 8.9 | 25.4 |
| JCC803 #1 236 h | 0.4 | 51.8 | 19.7 | 28.2 |
| JCC803 #2 236 h | 0.6 | 57.4 | 17.3 | 24.7 |

Methyl Ester Production Culturing Conditions:

One colony of JCC803 (Table 1) was inoculated into 10 mL of A+ media containing 50 μg/ml spectinomycin and 1% ethanol (v/v). This culture was incubated for 3 days in a bubble tube at 37° C. sparged at approximately 1-2 bubbles of 1% $CO_2$/air every 2 seconds in light (40-50 μE/m2/s PAR, measured with a LI-250A light meter (LI-COR)). The culture was inoculated into two flasks to a final volume of 20.5 ml and $OD_{730}$=0.08 in A+ media containing 200 μg/ml spectinomycin and 0.5 mM IPTG with either 0.5% methanol or 0.5% ethanol (v/v). These cultures were incubated in a shaking incubator at 150 rpm at 37° C. under 2% $CO_2$/air and continuous light (70-130 μE m2/s PAR, measured with a LI-250A light meter (LI-COR)) for three days. Water loss through evaporation was replaced with the addition of sterile Milli-Q water. Samples of 5 ml of these cultures ($OD_{730}$=5-6) were analyzed for the presence of ethyl or methyl esters.

Detection of Methyl Esters and Comparison with Ethyl Ester Production in the Same Strain:

Cell pellets were thawed and 1 ml aliquots of acetone (Acros Organics 326570010) containing 100 mg/L butylated hydroxytoluene (Sigma-Aldrich B1378) and 50 mg/L ethyl valerate (Fluka 30784) were added. The cell pellets were mixed with the acetone using a Pasteur pipette and vortexed twice for 10 seconds (total extraction time of 1-2 min). The suspensions were centrifuged for 5 min to pellet debris, and the supernatants were removed with Pasteur pipettes and subjected to analysis with a gas chromatograph using mass spectral detection (GC/MS).

An Agilent 7890A GC/5975C EI-MS equipped with a 7683 series autosampler was used to measure the ethyl esters. One μL of each sample was injected into the GC inlet using pulsed splitless injection (pressure: 20 psi, pulse time: 0.3 min, purge time: 0.2 min, purge flow: 15 mL/min) and an inlet temperature of 280° C. The column was a HP-5MS (Agilent, 30 m×0.25 mm×0.25 μm) and the carrier gas was helium at a flow of 1.0 mL/min. The GC oven temperature program was 50° C., hold one minute; 10°/min increase to 280° C.; hold ten minutes. The GC/MS interface was 290° C., and the MS range monitored was 25 to 600 amu. Compounds indicated by peaks present in total ion chromatograms were identified by matching experimentally determined mass spectra associated with the peaks with mass spectral matches found by searching in a NIST 08 MS database.

The culture of JCC803 incubated with ethanol contained ethyl palmitate [C16:0; retention time (rt): 18.5 min], ethyl heptadecanoate (C17rt: 19.4 min), ethyl oleate (C18:1; rt: 20.1 min) and ethyl stearate (C18:0; rt: 20.3 min) (FIG. 1). The relative amounts produced were C16:0>C18:0>C18:1>C17:0. The production of low levels of C17:0 and the absence of measured levels of C14:0/myristate in this experiment is likely a result of the use of A+ medium (JB 2.1 was used to generate the date in Table 7, above).

No ethyl esters were detected in the strain incubated with methanol. Instead, methyl palmitate (C16:0; retention time ("rt"): 17.8 min), methyl heptadecanoate (C17:0; rt: 18.8 min) and methyl stearate (C18:0) were found (FIG. 1; methyl palmitate: 0.1 mg/L; methyl heptadecanoate: 0.062 mg/L; methyl stearate: 0.058 mg/L; total FAMEs: 0.22 mg/L; % of DCW: 0.01).

The data presented herein shows that JCC803 and other cyanobacterial strains engineered with tesA-fadD-wax genes can utilize methanol, ethanol, butanol, and other alcohols, including exogenously added alcohols, to produce a variety of fatty acid esters. In certain embodiments, multiple types of exogenous or endogenous alcohols (e.g., methanol and ethanol; butanol or ethanol; methanol and butanol; etc.) could be added to the culture medium and utilized as substrates.

Example 3

Production of Fatty-Acid Esters Through Heterologous Expression of an Acyl-CoA Synthetase and a Wax Synthase In order to compare the yields of fatty-acid esters produced by recombinant strains expressing tesA-fadD or fadD-wax (i.e., two of the three genes in the tesA-fadD-wax synthetic operon), fadD-wax and tesA-fadD and were assembled as two-gene operons and inserted into pJB5 to yield pJB634 and pJB578, respectively. These recombination plasmids were transformed into Synechococcus sp. PCC 7002 as described in Example 1, above to generate the strains listed in Table 8. Table 8 also lists JCC723, described above.

TABLE 8

Joule Culture Collection (JCC) numbers of the Synechococcus sp. PCC 7002 recombinant strains with gene insertions on the native plasmid AQ1.

| Strain # | Promoter | Genes | Promoter-operon sequences | Marker | $OD_{730}$ | % DCW FAEE |
|---|---|---|---|---|---|---|
| JCC723 | PaphII | tesA-fadD-wax | SEQ ID NO: 10 | aadA | 15.35 | 0.20 |
| JCC1215 | PaphII | fadD-wax | SEQ ID NO: 13 | aadA | 10.10 | 0.04 |
| JCC1216 | PaphII | tesA-fadD | SEQ ID NO: 14 | aadA | 10.00 | 0.00 |

One 30-ml culture of each strain listed in Table 1 was prepared in JB 2.1 medium containing 200 mg/L spectinomycin and 1% ethanol (vol/vol) at an $OD_{730}=0.1$ in 125 ml flasks equipped with foam plugs (inocula were from five ml A+ cultures containing 200 mg/L spectinomyin started from colonies incubated for 3 days in a Multitron II Infors shaking photoincubator under continuous light of ~100 μE $m^{-2}s^{-1}$ photosynthetically active radiation (PAR) at 37° C. at 150 rpm in 2% $CO_2$-enriched air). The cultures were incubated for seven days in the Infors incubators under continuous light of ~100 μE $m^{-2}s^{-1}$ photosynthetically active radiation (PAR) at 37° C. at 150 rpm in 2% $CO_2$-enriched air. Fifty percent of the starting volume of ethanol was added approximately at day 5 based on experimentally determined stripping rates of ethanol under these conditions. Water loss was compensated by adding back milli-Q water (based on weight loss of flasks). Optical density measurements at 730 nm ($OD_{730}$) were taken (Table 8), and esters were extracted from cell pellets using the acetone procedure detailed in Example 2, above. Ethyl arachidate (Sigma A9010) at 100 mg/L was used as an internal standard instead of ethyl valerate. The dry cell weights (DCWs) were estimated based on the OD measurement using an experimentally determined average of 300 mg $L^{-1} OD_{730}^{-1}$.

Figure 2:
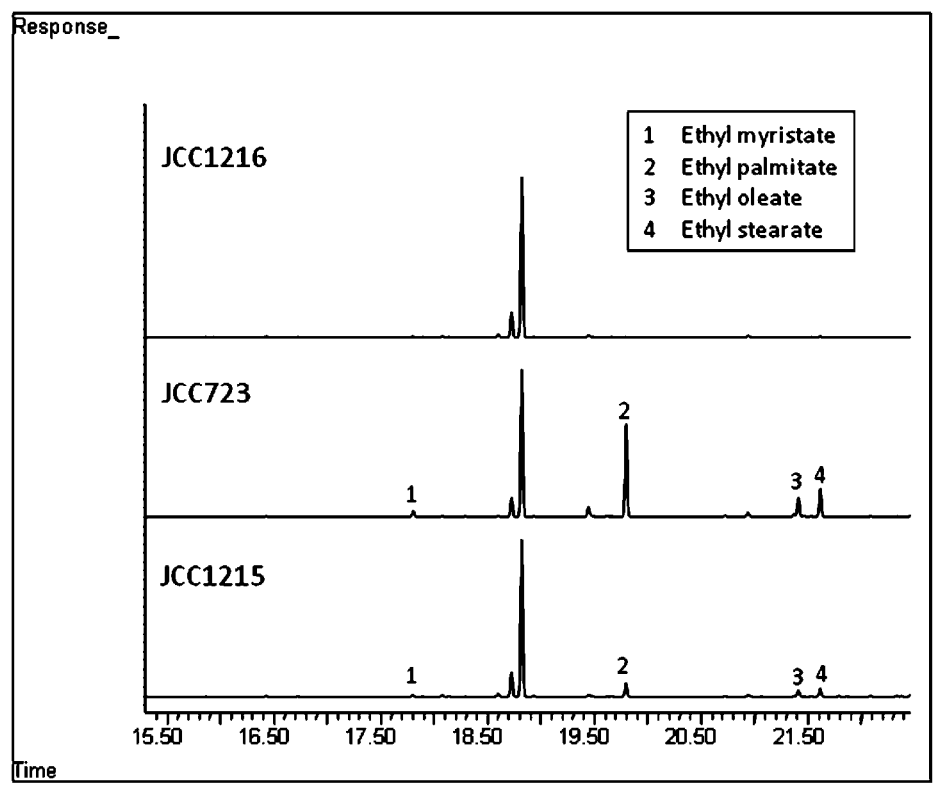
FIG. 2 shows three stacked GC/FID chromatograms comparing cell pellet extracts of the indicated cyanobacterial strains when cultured in the presence of ethanol. The interval between tick marks on the FID response axis is 20,000.

The acetone extracts were analyzed by GC/FID (for instrument conditions, see Example 2). In order to quantify the various esters, response factors (RF) were estimated from RFs measured for authentic ethyl ester standards and these RFs were used to determine the titres in the acetone extracts. The % DCW of the fatty-acid esters and the sum of the esters as % DCW is given in Table 8. Expression of fadD-wax was sufficient to allow production of fatty-acid ethyl esters (FAEEs), while expression of tesA-fadD did not result in any FAEEs (FIG. 2). The overall yield was lower than JCC723, indicating that the co-expression of tesA is beneficial for increasing yields of FAEEs in this strain.

Example 4

Production of Longer-Chain Fatty-Acid Esters by Addition of Respective Alcohols to tesA-fadD-Wax Cultures Seven 30-ml cultures of JCC803 (prepared from a single JCC803 culture that was diluted into 250 ml of JB 2.1 media containing 200 mg/L spectinomycin at an $OD_{730}=0.1$) in 125-ml flasks were used to evaluate the ability of JCC803 to esterify different alcohols with fatty acids. Seven different alcohols were added at concentrations previously determined to allow growth of JCC803 (Table 9). The cultures were incubated for seven days in a Multitron II Infors shaking photoincubator under continuous light of ~100 μE $m^{-2}s^{-1}$ photosynthetically active radiation (PAR) at 37° C. at 150 rpm in 2% $CO_2$-enriched air. Water loss was compensated by adding back milli-Q water (based on weight loss of flasks). Optical density measurements at 730 nm ($OD_{730}$) were taken (Table 3), and esters were extracted from cell pellets using the acetone procedure detailed in Example 2, above. Ethyl arachidate (Sigma A9010) at 100 mg/L was used as an internal standard instead of ethyl valerate. The dry cell weights (DCWs) were also determined for each culture so that the % DCW of the esters could be reported.

TABLE 9

| Alcohol | Catalog # | Concentration % (vol/vol) | Final $OD_{730}$ |
|---|---|---|---|
| Propanol | 256404 (Sigma) | 0.25 | 12.6 |
| Isopropanol | BP2632 (Fisher) | 0.25 | 12.6 |
| Butanol | 34867 (Sigma) | 0.1 | 12.5 |
| Hexanol | H13303 (Sigma) | 0.01 | 8.6 |
| Cyclohexanol | 105899 (Sigma) | 0.01 | 13.6 |
| Isoamyl alcohol | A393 (Fisher) | 0.05 | 13.6 |
| Ethanol | 2716 (Decon Labs Inc.) | 1.0 | 14.0 |

Figure 3:
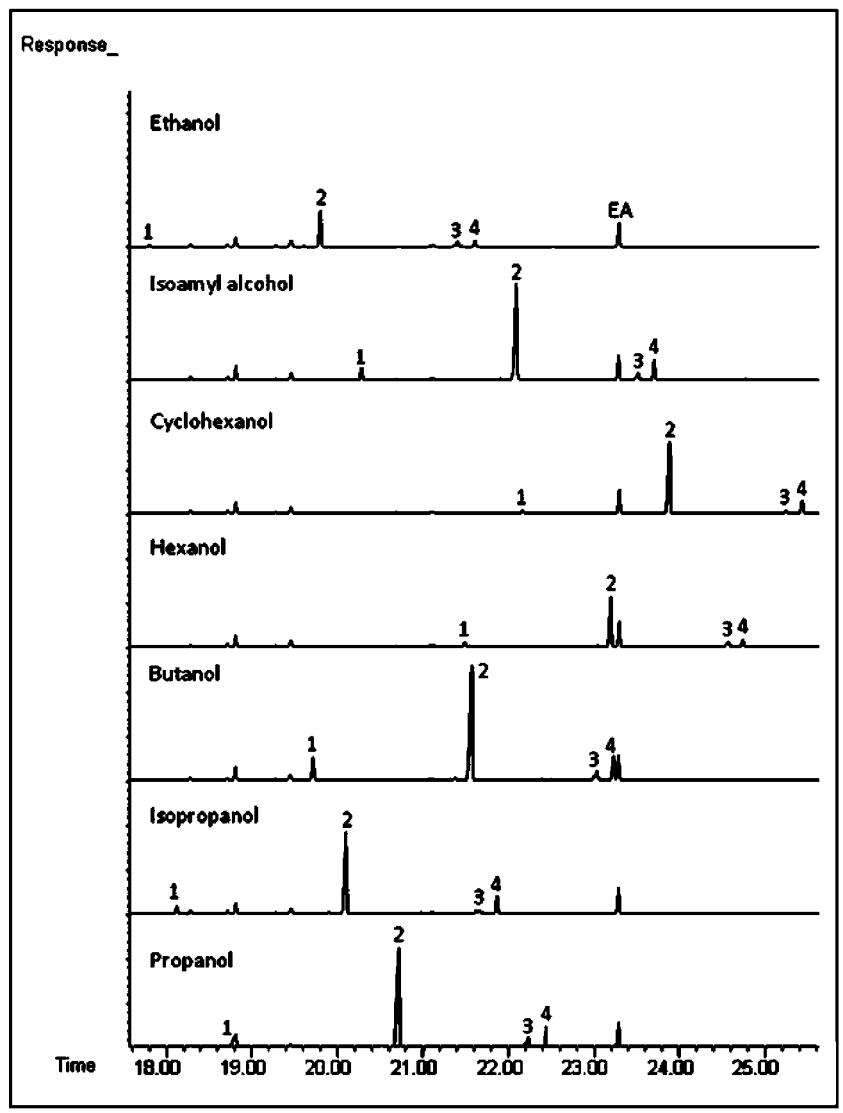
FIG. 3 depicts stacks of GC/FID chromatograms comparing cell pellet extracts of JCC803 cultures incubated with different alcohols (indicated on respective chromatograms). Numbers indicate the respective fatty acid ester corresponding to the alcohol added (1=myristate; 2=palmitate; 3=oleate; 4=stearate). EA=ethyl arachidate. The interval between tick marks on the FID response axis is 400,000.
Figure 4:
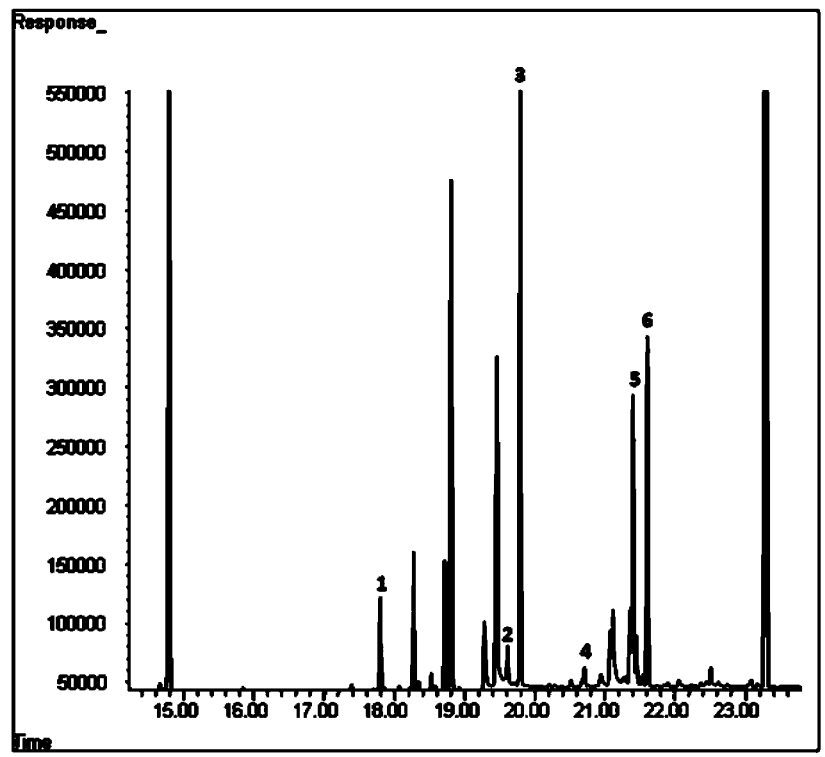
FIG. 4 depicts a GC/chromatogram of a cell pellet extract from a JCC803 culture incubated with ethanol. 1=ethyl myristate; 2=ethyl palmitoleate; 3=ethyl palmitate; 4=ethyl margarate; 5=ethyl oleate; 6=ethyl stearate.
Figure 5:
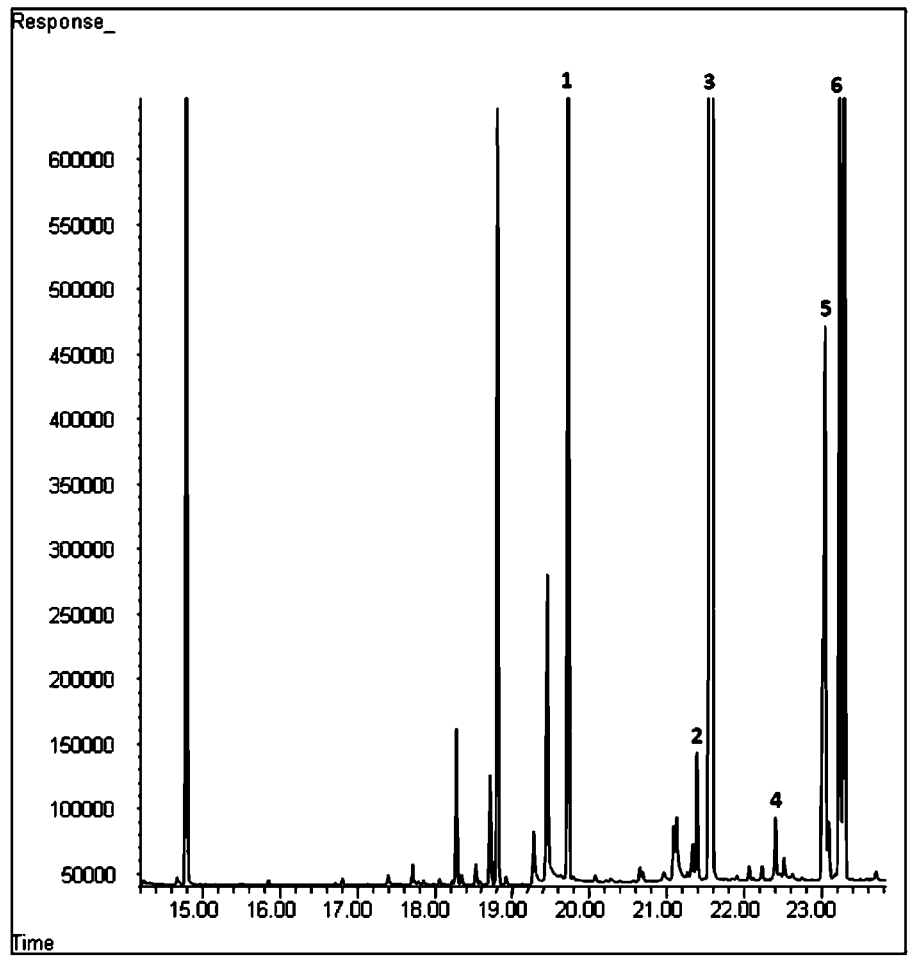
FIG. 5 depicts a GC/chromatogram of a cell pellet extract from a JCC803 culture incubated with butanol. 1=butyl myristate, 2=butyl palmitoleate, 3=butyl palmitate, 4=butyl margarate, 5=butyl oleate, 6=butyl stearate.

The acetone extracts were analyzed by GC/MS and GC/FID, as described above. The compounds indicated by peaks present in the total ion chromatograms were identified by matching the mass spectra associated with the peaks with mass spectral matches found by searching the NIST 08 MS database or by interpretation of the mass spectra when a respective mass spectrum of an authentic standard was not available in the database. In all cases, the corresponding alcohol esters of fatty acids were produced by JCC803 (FIG. 3). Six fatty-acid esters were detected and quantified in the cell pellet extracts: myristate (C14:0), palmitoleate (C16:1Δ9), palmitate (C16:0), margarate (C17:0), oleate (C18:1Δ9) and stearate (C18:0). Magnified chromatograms for JCC803 incubated with ethanol and butanol are shown in FIG. 4 and FIG. 5, respectively, so that the lower-yielding palmitoleate and margarate esters could be indicated on the chromatograms. In order to quantify the various esters, response factors (RF) were estimated from RFs measured for authentic ethyl ester and these RFs were used to determine the titres in the acetone extracts. The % DCW of the different esters and the sum of the esters as % DCW is given in Table 10. The % of the individual esters by weight and the total ester yield in mg/L is given in Table 11.

In general, the provision of longer-chain alcohols increased the yields of fatty-acid esters. The addition of butanol resulted in the highest yields of fatty-acid esters. Because butanol can be made biosynthetically (Nielsen et al. 2009, and references therein), exogenous butanol biosynthetic pathways could be expressed by one skilled in the art to generate a photosynthetic strain which can produce butyl esters without the addition of butanol. The use of butanol and butanol-producing pathways in other microbes containing the tesA-fadD-wax pathway would also be expected to increase yields of fatty-acid esters.

Example 5

Reproducibility of Butanol Yields in tesA-fadD-Wax Cultures

Six 30-ml cultures of JCC803 (prepared from a single JCC803 culture that was diluted into 200 ml of JB 2.1 media/spec200 at an $OD_{730}$=0.1) in 125 ml flasks were used to evaluate the ability of JCC803 cultures to produce butyl esters when containing different concentrations of butanol. Six different concentrations were tested (Table 12). The cultures were incubated for 21 days in a Multitron II Infors shaking photoincubator under continuous light at ~100 µE $m^{-2}s^{-1}$ PAR at 37° C. at 150 rpm in 2% $CO_2$-enriched air. Fifty percent of the starting volume of butanol was added approximately every 3.5 days based on experimentally determined stripping rates of butanol under these conditions. Water loss was compensated by adding back milli-Q water (based on weight loss of flasks). $OD_{730}$s were taken and esters were extracted from cell pellets using the acetone procedure detailed above. 100 mg/L ethyl arachidate (Sigma A9010) was used as an internal standard instead of ethyl valerate. The dry cell weights (DCWs) were also determined for each culture so that the % DCW of the esters could be reported.

An Agilent 7890A GC/FID equipped with a 7683 series autosampler was used to quantify the butyl esters. One microliter of each sample was injected into the GC inlet (split 5:1, pressure: 20 psi, pulse time: 0.3 min, purge time: 0.2 min, purge flow: 15 mL/min), which was at a temperature of 280° C. The column was an HP-5MS (Agilent, 30 m×0.25 mm×0.25 µm), and the carrier gas was helium at a flow of 1.0 mL/min. The GC oven temperature program was: 50° C., hold one minute; 10°/min increase to 280° C.; hold ten minutes. Butyl myristate, butyl palmitate, butyl margarate, butyl oleate

TABLE 10

The yield of the fatty acid-esters individually and total as % dry cell weight

|  | Myristate | Palmitoleate | Palmitate | Margarate | Oleate | Stearate | Total Ester |
|---|---|---|---|---|---|---|---|
| Ethyl | 0.05 | 0.02 | 0.94 | 0.01 | 0.11 | 0.15 | 1.3 |
| Propyl | 0.26 | 0.06 | 3.22 | 0.03 | 0.21 | 0.48 | 4.3 |
| Isopropyl | 0.20 | 0.04 | 2.42 | 0.02 | 0.08 | 0.42 | 3.2 |
| Butyl | 0.59 | 0.06 | 3.67 | 0.03 | 0.19 | 0.56 | 5.1 |
| Hexyl | 0.11 | 0.04 | 1.33 | 0.02 | 0.17 | 0.19 | 1.8 |
| Cyclohexyl | 0.09 | 0.03 | 1.88 | 0.01 | 0.09 | 0.31 | 2.4 |
| Isoamyl | 0.31 | 0.05 | 2.84 | 0.02 | 0.15 | 0.46 | 3.8 |

TABLE 11

The % of the individual esters by weight and total ester yield in mg/L.

|  | Myristate | Palmitoleate | Palmitate | Margarate | Oleate | Stearate | Total Ester |
|---|---|---|---|---|---|---|---|
| Ethyl | 4.2 | 1.2 | 73.4 | 0.7 | 8.6 | 12.0 | 77.6 |
| Propyl | 6.0 | 1.3 | 76.0 | 0.7 | 4.9 | 11.1 | 251.7 |
| Isopropyl | 6.2 | 1.2 | 76.4 | 0.8 | 2.4 | 13.0 | 188.5 |
| Butyl | 11.4 | 1.1 | 72.6 | 0.5 | 3.7 | 10.8 | 308.9 |
| Hexyl | 6.0 | 2.1 | 71.9 | 1.1 | 8.9 | 10.0 | 65.3 |
| Cyclohexyl | 3.6 | 1.1 | 78.5 | 0.6 | 3.6 | 12.7 | 139.6 |
| Isoamyl | 8.1 | 1.2 | 74.6 | 0.5 | 3.9 | 11.8 | 226.8 | and butyl stearate were quantified by determining appropriate response factors for the number of carbons present in the butyl esters from commercially available fatty-acid ethyl esters ("FAEEs") and fatty acid butyl esters ("FABEs"). The calibration curves were prepared for ethyl laurate (Sigma 61630), ethyl myristate (Sigma E39600), ethyl palmitate (Sigma P9009), ethyl oleate (Sigma 268011), ethyl stearate (Fluka 85690), butyl laurate (Sigma W220604) and butyl stearate (Sigma S5001). The concentrations of the butyl esters present in the extracts were determined and normalized to the concentration of ethyl arachidate (internal standard).

The yields of the JCC803 cultures as given by the % DCW of the fatty acid butyl esters is given in Table 12. The highest yield of 14.7% resulted from the culture incubated with 0.05% butanol (vol/vol) although the 0.075% butanol-containing culture was approximately the same.

TABLE 12

Yield of total FABES as % DCW for the JCC803 cultures containing different concentrations of butanol and final $OD_{730}$ of the cultures.

| Concentration of butanol % (vol/vol) | $OD_{730}$ | % DCW |
|---|---|---|
| 0.2 | 10.6 | 11.75 |
| 0.1 | 9.0 | 12.43 |
| 0.075 | 12.8 | 14.53 |
| 0.05 | 12.0 | 14.71 |
| 0.025 | 13.4 | 10.43 |
| 0.01 | 16.0 | 6.12 |

Example 6

Secretion of Esters Produced by an Engineered Cyanobacterium

Plasmids. *Escherichia coli* exports alkanes and other hydrophobic molecules out of the cell via the TolC-AcrAB transporter complex (Tsukagoshi and Aono, 2000; Chollet et al. 2004). PCR primer sets were designed to amplify tolC (Genbank #NC_000913.2, locus b3035) and acrA-acrB as an operon (Genbank #NC_000913.2, loci b0463, b0462) from *E. coli* MG1655 (ATCC #700926). The tolC and acrAB genes were amplified from MG1655 genomic DNA using the Phusion High-Fidelity PCR kit F-553 from New England BioLabs (Ipswich, Mass.) following the manufacturer's instructions. Buffer GC and 3% dimethyl sulfoxide (DMSO) were used for the PCR reactions. The amplicons were assembled into a three-gene, two-promoter construct ("transporter insert"; $P_{psaA}$-tolC-$P_{tsr2142}$-acrAB) and placed in multiple cloning site of recombination vector pJB161 (SEQ ID #15) to yield pJB1074. pJB161 (and pJB161-derived plasmids, including pJB1074) contain an upstream homology region (UHR) and a downstream homology region (DHR) that allows recombination into the pAQ7 plasmid of *Synechococcus* sp. PCC7002 at the lactate dehydrogenase locus (for pAQ7 plasmid sequence, see Genbank # CP000957). The homology regions flank a multiple cloning site (mcs), the natural terminator from the alcohol dehydrogenase gene from *Zymomonas mobilis* (adhII) and a kanamycin cassette which provides resistance in both *E. coli* and *Synechococcus* sp. PCC 7002. The transporter insert with flanking homology regions is provided as SEQ ID 16.

Strain Construction.

As described above, JCC803 is a strain of *Synechococcus* sp. PCC 7002 that has been engineered to produce esters of fatty acids (such as those found in biodiesel) when incubated in the presence of alcohols. The strain contains a thioesterase (tesA), an acyl-CoA synthetase (fadD) and a wax synthase (wxs) inserted into plasmid pAQ1 by homologous recombination.

The genes present in pJB161 and pJB1074 were integrated into the plasmid pAQ7 in *Synechococcus* sp. PCC 7002 (specifically, strain JCC803) using the following procedure. A 5 ml culture of JCC803 in A+ medium containing 200 mg/L spectinomycin was incubated in an Infors shaking incubator at 150 rpm at 37° C. under 2% CO2/air and continuous light (70-130 E $m^{-2}$ $s^{-1}$ PAR, measured with a LI-250A light meter (LI-COR)) until it reached an OD730 of 1.14. For each plasmid, 500 µl of culture and 5 µg of plasmid DNA were added into a microcentrifuge tube. The tubes were then incubated at 37° C. in the dark rotating on a Rotamix RKSVD (ATR, Inc.) on a setting of approximately 20. After 4 hours for pJB161 or 7 hours for pJB1074, the cells were pelleted using a microcentrifuge. All but ~100 µl of the supernatants were removed and the cell pellets were resuspended using the remaining supernatant and plated on A+ agar plates. The plates were incubated overnight in a Percival lighted incubator under constant illumination (40-60 µE $m^{-2}$ $s^{-1}$ PAR, measured with a LI-250A light meter (LI-COR)) at 37° C. for about 24 hours. On the following day, spectinomycin and kanamycin solution was added underneath the agar of the plates to estimated concentration of 25 mg/L spectinomycin and 50 mg/L kanamycin (assuming 40 ml A+ agar in the plate). These plates were placed back into the incubator until tiny colonies became visible. The plates were moved to another Percival incubator under the same conditions except that 1% $CO_2$ was maintained in the air (allows for faster growth). Approximately 110 colonies formed for recombinant strains resulting from the pJB1074 transformation and 2800 colonies resulting from the pJB160 transformation. A colony from the pJB161 transformation plate was designated JCC1132.

Thirty colonies were picked from the tolC-acrAB transformation plate and streaked onto both an A+ plate with 100 mg/L spectinomycin and 0.05 mg/L erythromycin and an A+ plate with 100 mg/L spectinomycin and 0.1 mg/L erythromycin. Erythromycin is a substrate for the TolC-AcrAB transporter (Chollet et al. 2004) and served to verify function of the transporter in naturally erythromycin-sensitive *Synechococcus* sp. PCC 7002. The plates were incubated in Percival lighted incubator at 37° C. under constant illumination (40-60 µE $m^{-2}$ $s^{-1}$ PAR, measured with a LI-250A light meter (LI-COR)) at 37° C. After two days, slight growth was visible on both plates. Eight days after streaking, variable growth and survival was evident on most of the streaks on the 0.05 mg/L erythromycin plate. On the 0.1 mg/L erythromycin plate, all of the streaks except for two had become nonviable. The same source colonies that produced the two viable streaks on 0.1 mg/L erythromycin produced streaks that were healthy on the 0.05 mg/L erythromycin plate. One of these strains on the 0.1 mg/L erythromycin plate was designated JCC1585 (see Table 13 for a list of strains).

TABLE 13

Strains and control strain investigated for the secretion of butyl esters.

| JCC # | Parent strain | Recombinant genes/Promoters with loci | Marker |
|---|---|---|---|
| JCC1132 | JCC803 | pAQ1:: $p_{trc}$-tesa-fadd-wxs-aada; pAQ7::$kan^r$ | spectinomycin kanamycin |
| JCC1585 | JCC803 | pAQ1:: $p_{trc}$-tesa-fadd-wxs-aada; pAQ7:: $p_{psaa}$-tolc-$p_{tsr2142}$-acrab-kanr | spectinomycin kanamycin |

Erythromycin Tolerance in Liquid Culture.

To verify the improved tolerance of JCC1585 to erythromycin compared to JCC1132, a 5 ml A+ culture containing 200 mg/L spectinomycin and 0.5 mg/L erythromycin (JCC1585) or containing 200 mg/L spectinomycin and 50 mg/L kanamycin (JCC1132) were used to inoculate 30 ml of JB 2.1 containing 200 mg/L spectinomycin and 0.5, 0.6, 0.7, 0.8, 0.9, or 1 mg/L erythromycin in 125 ml culture flasks at an $OD_{730}$ of 0.1. These cultures were incubated in an Infors shaking incubator at 150 rpm at 37° C. under 2% $CO_2$/air and continuous light (70-130 µE m$^{-2}$ s$^{-1}$ PAR, measured with a LI-250A light meter (LI-COR)). Timepoints were taken at 5 and 10 days of growth, during which water loss was replaced through addition of milli-Q water. Table 14 shows $OD_{730}$ values of JCC1132 and JCC1585 cultures at day 5 and 10 with different concentrations of erythromycin present in the medium. The JCC1585 cultures were tolerant of erythromycin concentrations of up to 1 mg/L (highest concentration tested) after 10 days while the JCC1132 cultures had bleached under all concentrations of erythromycin tested.

TABLE 14

| Strain | Erythromycin Concentration (mg/L) | $OD_{730}$ Start of Experiment | $OD_{730}$ Day 5 | $OD_{730}$ Day 10* |
|---|---|---|---|---|
| JCC1132 | 0.5 | 0.1 | 5.72 | — |
|  | 0.6 | 0.1 | 4.76 | — |
|  | 0.7 | 0.1 | 4.98 | — |
|  | 0.8 | 0.1 | 2.94 | — |
|  | 0.9 | 0.1 | 2.50 | — |
|  | 1.0 | 0.1 | 2.26 | — |
| JCC1585 | 0.5 | 0.1 | 6.60 | 7.34 |
|  | 0.6 | 0.1 | 6.34 | 6.20 |
|  | 0.7 | 0.1 | 5.82 | 5.74 |
|  | 0.8 | 0.1 | 5.80 | 4.84 |
|  | 0.9 | 0.1 | 5.34 | 5.04 |
|  | 1.0 | 0.1 | 5.58 | 5.12 |

*"—" indicates culture had bleached

To verify the improved tolerance of JCC1585 to erythromycin compared to JCC1132, a 5 ml A+ culture containing 200 mg/L spectinomycin and 0.5 mg/L erythromycin (JCC1585) or containing 200 mg/L spectinomycin and 50 mg/L kanamycin (JCC1132) were used to inoculate 30 ml of JB 2.1 media containing 200 mg/L spectinomycin and 0.5, 0.6, 0.7, 0.8, 0.9, or 1 mg/L erythromycin in 125 ml culture flasks at an OD730 of 0.1. These cultures were incubated in an Infors shaking incubator at 150 rpm at 37° C. under 2% CO2/air and continuous light (70-130 µE m2/s PAR, measured with a LI-250A light meter (LI-COR)). Timepoints were taken at 5 and 10 days of growth, during which water loss was replaced through addition of milli-Q water. The JCC1585 cultures were tolerant of erythromycin concentrations of up to 1 mg/L (highest concentration tested) after 10 days while the JCC1132 cultures had bleached under all concentrations of erythromycin tested (Table 14).

Culture Conditions.

To test for secretion of butyl esters, 5 ml A+ cultures with 200 mg/L spectinomycin and 50 mg/L kanamycin were inoculated from colonies for JCC1132 and JCC1585. These cultures were used to inoculate duplicate 30 ml cultures in JB2.1 medium containing 200 mg/L spectinomycin and 50 mg/L kanamycin. At the beginning of the experiment, 15 µl butanol (Sigma 34867) was added to each flask so that fatty acid butyl esters (FABEs) would be produced by the cultures. These cultures were incubated in an Infors shaking incubator at 150 rpm at 37° C. under 2% $CO_2$/air and continuous light (70-130 µE m$^{-2}$ s$^{-1}$ PAR, measured with a LI-250A light meter (LI-COR)) for three days. At day 4 of the experiment, 7.5 µl butanol was added to the cultures to compensate for the experimentally determined stripping rate of butanol under these conditions. Water loss through evaporation was replaced with the addition of sterile Milli-Q water at day 7 and $OD_{730}$ readings were taken for each culture.

Detection of Butyl Esters.

An aliquot of 250 µl was removed from each culture and centrifuged at 1500 rpm in Microcentrifuge 5424 (Eppendorf) for ~2 min. The supernatants were removed and the pellets were suspended in 500 µl milli-Q $H_2O$. The samples were centrifuged and the supernatants discarded. An additional centrifugation step for 4 min was performed, and any remaining supernatant was removed. The weight of the tube and the cell pellet were measured. One milliliter of acetone (Acros Organics 326570010) containing 100 mg/L butylated hydroxytoluene (BHT, Sigma-Aldrich B1378) and 100 mg/L ethyl arachidate (Sigma A9010) were added to each pellet, and the mixture was pipetted up and down until none of the pellet remained on the wall of the tube. Each tube was then vortexed for 15 s, and the weight of the tube, acetone solution, and cells was taken. The tubes were then spun down and 500 µl of supernatant was submitted for GC analysis. From these samples, the percent dry cell weights of fatty acid butyl esters in the cell pellets were determined.

In order to quantify FABE's in the medium, 300 µL of a 20% (v/v) Span80 (Fluka 85548) solution was added to each flask and mixed by swirling for 30 seconds. These mixtures were then poured into 50 mL Falcon tubes. Five mL of isooctane containing 0.01% BHT and 0.005% ethyl arachidate was added to the flasks and swirled for several seconds. The solutions were then poured into the appropriate 50 mL Falcon tubes containing the culture from the flasks. The tube was then shaken for 10 seconds and centrifuged using a Sorvall RC6 Plus superspeed centrifuge (Thermo Electron Corp) and a F13S-14X50CY rotor (6000 rpm for 20 min). One milliliter of the organic phase (upper phase) was removed and submitted for GC analysis.

The butyl esters produced by JCC803 and JCC803-derived strains were identified by GC/MS employing an Agilent 7890A GC/5975C ELMS equipped with a 7683 series autosampler. One microliter of each sample was injected into the GC inlet using a pulsed splitless injection (pressure: 20 psi, pulse time: 0.3 min, purge time: 0.2 min, purge flow: 15 mL/min) and an inlet temperature of 280° C. The column was a HP-5MS (Agilent, 30 m×0.25 mm×0.25 µm) and the carrier gas was helium at a flow of 1.0 mL/min. The GC oven temperature program was 50° C., hold one minute; 10°/min increase to 280° C.; hold ten minutes. The GC/MS interface was 290° C., and the MS range monitored was 25 to 600 amu. Butyl myristate [retention time (rt): 19.72 min], butyl palmitate (rt: 21.58 min) butyl heptadecanoate (rt: 22.40 min), butyl oleate (rt: 23.04 min) and butyl stearate (rt: 23.24 min) were identified by matching experimentally determined mass spectra associated with the peaks with mass spectral matches found by searching in a NIST 08 MS database.

An Agilent 7890A GC/FID equipped with a 7683 series autosampler was used to quantify the butyl esters. One microliter of each sample was injected into the GC inlet (split 5:1, pressure: 20 psi, pulse time: 0.3 min, purge time: 0.2 min, purge flow: 15 mL/min), which was at a temperature of 280° C. The column was an HP-5MS (Agilent, 30 m×0.25 mm×0.25 µm), and the carrier gas was helium at a flow of 1.0 mL/min. The GC oven temperature program was 50° C., hold one minute; 10°/min increase to 280° C.; hold ten minutes. Butyl myristate (rt: 19.68 min], butyl palmitate (rt: 21.48 min), butyl heptadecanoate (rt: 22.32 min), butyl oleate (rt: 22.95 min) and butyl stearate (rt: 23.14 min) were quantified by determining appropriate response factors for the number of carbons present in the butyl esters from commercially-available fatty acid ethyl esters (FAEEs) and FABEs. The calibration curves were prepared for ethyl laurate (Sigma 61630), ethyl myristate (Sigma E39600), ethyl palmitate (Sigma P9009), ethyl oleate (Sigma 268011), ethyl stearate (Fluka 85690), butyl laurate (Sigma W220604) and butyl stearate (Sigma S5001). The concentrations of the butyl esters present in the extracts were determined and normalized to the concentration of ethyl arachidate (internal standard).

Peaks with areas greater than 0.05 could be integrated by the Chemstation™ software (Agilent®), and the concentrations of the butyl esters in both media and supernatant were determined from these values. The dry cell weight (DCW) of these strains was based on a measurement of $OD_{730}$ and calculated based on the observed average DCW/OD relationship of 0.29 g $L^{-1}$ $OD^{-1}$. In the case of the JCC1585 culture supernatant, small peaks for butyl myristate (flask 1 area: 1.26, flask 2: 2.23) and butyl palmitate (flask 1 area: 5.16, flask 2: 5.62) were observed while no peak with an area greater than 0.05 at these retention times was found in the media extraction of the JCC1132 cultures. The $OD_{730}$ percent dry cell weights of the FABEs in the cell pellets and the media are given in Table 15. The total % DCW of FABE's found in the cell pellets is indicated, as is the % DCW of butyl myristate and butyl palmitate found in the pellets and the media.

TABLE 15

| Strain (flask) | OD730 | FABEs (% DCW) | Pellet butyl myristate + butyl palmitate (% DCW) | Media butyl myristate + butyl palmitate (% DCW) |
|---|---|---|---|---|
| JCC1585 (1) | 9.65 | 7.76 | 6.59 | 0.013 |
| JCC1132 (1) | 5.44 | 4.93 | 4.20 | 0 |
| JCC1585 (2) | 8.50 | 7.79 | 6.65 | 0.018 |
| JCC1132 (2) | 4.48 | 4.60 | 3.85 | 0 |

Table 15 shows that the recombinant expression of to/C in an engineered cyanobacterium provides for the secretion of a detectable fraction of esters (in this case, butyl esters) synthesized by the engineered cell. The amount of secretion achieved can be modulated by increasing concentrations of erythromycin or other transporter substrates, and/or through optimization of expression levels (promoter strength and codon optimization strategies) and/or specifically targeting a cyanobacterial membrane by employing appropriate cyanobacterial N-terminal leader sequences.

Example 7

Secretion of Fatty Acids in *Thermosynechococcus Elongatis* BP-1 (Δaas)

Strain Construction.

*Thermosynechoccocus elongatus* BP-1 long-chain-fatty-acid CoA ligase gene (aas, GenBank accession number NP_682091.1) was replaced with a thermostable kanamycin resistance marker (kan_HTK, GenBank accession number AB121443.1) as follows:

Regions of homology flanking the BP-1 aas gene (Accession Number: NP_682091.1) were amplified directly from BP-1 genomic DNA using the primers in Table 16. PCR amplifications were performed with Phusion High Fidelity PCR Master Mix (New England BioLabs) and standard amplification conditions.

TABLE 16

| Primer | Sequence | SEQ ID NO: | Restriction site added |
|---|---|---|---|
| Upstream forward | 5'-GCTATGCCTGCAGGGGCCTTTTATGAGGAGCGGTA-3' | 21 | SbfI |
| Upstream reverse | 5'-GCTATGGCGGCCGCTCTTCATGACAGACCCTATGGATACTA-3' | 22 | NotI |
| Downstream forward | 5'-GCTATGGGCGCGCCTTATCTGACTCCAGACGCAACA-3' | 23 | AscI |
| Downstream reverse | 5'-GCTATGGGCCGGCCGATCCTTGGATCAACTCACCCT-3' | 24 | FseI |

The amplified upstream homologous region (UHR) was cloned into the UHR of a pJB5 expression vector containing kan_HTK by digesting the insert and vector individually with SbfI and NotI restriction endonucleases (New England BioLabs) following well known laboratory techniques. Digestions were isolated on 1% TAE agarose gel, purified using a Gel Extraction Kit (Qiagen), and ligated with T4 DNA Ligase (New England BioLabs) incubated at room temperature for 1 hour. The ligated product was transformed into NEB 5-alpha chemically competent *E. coli* cells (New England BioLabs) using standard techniques and confirmed by PCR. The downstream homologous region (DHR) was cloned into the resulting plasmid following a similar protocol using AscI and FseI restriction endonucleases (New England BioLabs). The final plasmid (pJB1349) was purified using QIAprep Spin Miniprep kit (Qiagen) and the construct was confirmed by digestion with HindIII, AseI and PstI restriction endonucleases (New England BioLabs).

BP-1 was grown in 5 ml B-HEPES liquid media in a glass test tube (45° C., 120 rpm, 2% $CO_2$) to $OD_{730}$ 1.28. A 1 ml aliquot of culture was transferred to a fresh tube and combined with 1 ug of purified pJB1349. The culture was incubated in the dark (45° C., 120 rpm, 2% $CO_2$) for 4 hours. 4 ml of fresh B-HEPES liquid media were added and the culture was incubated with light (45° C., 120 rpm, 2% $CO_2$) overnight. 500 µl of the resulting culture were plated in 3 ml of B-HEPES soft agar on B-HEPES plates containing 60 µg/ml kanamycin and placed in an illuminated incubator (45° C., ambient $CO_2$) until colonies appeared (1 week), then moved into a 2% $CO_2$ illuminated incubator for an additional week.

Four randomly selected colonies (samples A-D) were independently grown in 5 ml B-HEPES liquid media with 60 µg/ml kanamycin in glass test tubes (45° C., 120 rpm, 2% $CO_2$) for one week. Replacement of aas gene was confirmed by PCR of whole cell genomic DNA by a culture PCR protocol as follows. Briefly, 100 µl of each culture was resuspended in 50 µl lysis buffer (96.8% di$H_2O$, 1% Triton X-100, 2% 1M Tris pH 8.5, 0.2% 1M EDTA). 10 µl of each suspension were heated 10 min at 98° C. to lyse cells. 1 µl of lysate was used in 15 µl standard PCR reactions using Quick-Load Taq 2× Master Mix (New England BioLabs). The PCR product showed correct bands for an unsegregated knockout.

All cultures were maintained in fresh B-HEPES liquid media with 60 µg/ml kanamycin for an additional week. The PCR reaction described above was repeated, again showing correct bands for an unsegregated knockout. Cultures were maintained in liquid culture, and one representative culture was saved as JCC1862.

Detection and Quantification of Free Fatty Acids in Strains.

Each of the four independently inoculated cultures described above (samples A-D), as well as BP-1, was analyzed for secretion of free fatty acids. $OD_{730}$ was measured, and the volume in each culture tube was recorded. Fresh B-HEPES liquid media was added to each tube to bring the total volume to 5 ml and free fatty acids were extracted as follows:

Samples were acidified with 50 µl 1N HCl. 500 µl of 250 g/L methyl-β-cyclodextrin solution was added and samples were transferred to 15-ml conical tubes after pulse-vortexing. 1 ml of 50 mg/L butylated hydroxytoluene in isooctane was added to each tube. Samples were vortexed 20 s, then centrifuged 5 min at 6000 RCF to fractionate. 500 µl of the isooctane layer were placed into a new tube and submitted for GC analysis.

Concentrations of octanoic acid, decanoic acid, lauric acid, myristic acid, palmitoleic acid, palmitic acid, oleic acid, stearic acid, and 1-nonadecene extractants were quantitated by gas chromatography/flame ionization detection (GC/FID). Unknown peak areas in biological samples were converted to concentrations via linear calibration relationships determined between known authentic standard concentrations and their corresponding GC-FID peak areas. Standards were obtained from Sigma. GC-FID conditions were as follows. An Agilent 7890A GC/FID equipped with a 7683 series autosampler was used. 1 µl of each sample was injected into the GC inlet (split 5:1, pressure: 20 psi, pulse time: 0.3 min, purge time: 0.2 min, purge flow: 15 ml/min) and an inlet temperature of 280° C. The column was a HP-5MS (Agilent, 30 m×0.25 mm×0.25 µm) and the carrier gas was helium at a flow of 1.0 ml/min. The GC oven temperature program was 50° C., hold one minute; 10° C./min increase to 280° C.; hold ten minutes.

GC results showed that the unsegregated aas knockout increased fatty acid production relative to BP-1 (Table 17), with myristic and oleic acid making up the majority of the increase (Table 18).

TABLE 17

Fatty Acid Production by Sample

| Sample | $OD_{730}$ | Fatty acids (% DCW in media) | Fatty acids (mg/L) |
|---|---|---|---|
| A | 6.25 | 0.20 | 3.66 |
| B | 5.20 | 0.11 | 1.71 |
| C | 5.60 | 0.24 | 3.85 |
| D | 5.80 | 0.23 | 3.83 |
| BP-1 | 6.90 | 0.04 | 0.88 |

TABLE 18

Fatty Acid Production by Type

| Sample | Myristic (mg/L) | Palmitic (mg/L) | Oleic (mg/L) |
|---|---|---|---|
| A | 0.119 | 0.051 | 0.032 |
| B | 0.000 | 0.072 | 0.042 |
| C | 0.134 | 0.063 | 0.040 |
| D | 0.130 | 0.060 | 0.038 |
| BP-1 | 0.000 | 0.044 | 0.000 |

Example 8

Increased Production of Fatty Acids and Fatty Esters in *Thermosynechococcus Elongatis* BP-1 (Δaas)

Transformation of BP-1.

As disclosed in PCT/US2010/042667, filed Jul. 20, 2010, *Thermosynechococcus elongatus* BP-1 is transformed with integration or expression plasmids using the following protocol. 400 ml *Thermosynechococcus elongatus* BP-1 in B-HEPES medium is grown in a 2.8 l Fernbach flask to an $OD_{730}$ of 1.0 in an Infors Multritron II shaking photoincubator (55° C.; 3.5% $CO_2$; 150 rpm). For each transformation, 50 ml cell culture is pelleted by centrifugation for 20 min (22° C.; 6000 rpm). After removing the supernatant, the cell pellet is resuspended in 500 µl B-HEPES and transferred to a 15 ml Falcon tube. To each 500 µl BP-1 cell suspension ($OD_{730}$ of ~100), 25 µg undigested plasmid (or no DNA) is added. The cell-DNA suspension is incubated in a New Brunswick shaking incubator (45° C.; 250 rpm) in low light (~3 µmol photons $m^{-2}$ $s^{-1}$). Following this incubation, the cell-DNA suspension is made up to 1 ml by addition of B-HEPES, mixed by gentle vortexing with 2.5 ml of molten B-HEPES 0.82% top agar solution equilibrated at 55° C., and spread out on the surface of a B-HEPES 1.5% agar plate (50 ml volume). Plates are left to sit at room temperature for 10 min to allow solidification of the top agar, after which time plates are placed in an inverted position in a Percival photoincubator and left to incubate for 24 hr (45° C.; 1% $CO_2$; 95% relative humidity) in low light (7-12 µmol photons $m^{-2} s^1$). After 24 hr, the plates are underlaid with 300 µl of 10 mg/ml kanamycin so as to obtain a final kanamycin concentration of 60 µg/ml following complete diffusion in the agar. Underlaid plates are placed back in the Percival incubator and left to incubate (45° C.; 1% $CO_2$; 95% relative humidity; 7-12 µmol photons $m^{-2} s^1$) for twelve days.

Increased Fatty Acids in BP-1.

*Thermosynechococcus elongatus* BP-1 (Δaas) is first constructed as described in the above Example. BP-1 (Δaas) is shown to have elevated levels of both intracellular and extracellular levels of free fatty acids relative to wild-type because mechanistic analysis suggests that cells lacking an acyl-ACP synthetase have the inability to recycle exogenous or extracellular fatty acids; the extracellular fatty acid chains are diverted away from transport into the inner cellular membrane while other transport systems are thought to continue to export fatty acids. Therefore, to up-regulate fatty acid production, BP-1 (Δaas) is transformed with a plasmid (e.g., pJB1349) carrying a thioesterase gene (see Table 3A). Increased cellular level of fatty acid production may be attributed to the combination of the aas deletion decreasing extracellular import of fatty acids and the addition of the thioesterase gene and/or thioesterase gene homologues.

Fatty Acid Esters.

The thioesterase gene with or without the leader sequence removed (Genbank #NC 000913, ref: Chot and Cronan, 1993), the *E. coli* acyl-CoA synthetase fadD (Genbank #NC 000913, ref: Kameda and Nunn, 1981) and the wax synthase (wxs) from *Acinetobacter* baylyi strain ADPI (Genbank #AF529086.1, ref: Stöveken et al. 2005) genes are designed for codon optimization, checking for secondary structure effects, and removal of any unwanted restriction sites (NdeI, XhoI, BamHI, NgoMIV, NcoI, SadI, BsrGI, AvrII, BmtI, MiuI, EcoRI, SbfI, Nod, SpeI, XbaI, Pad, AscI, FseI). These genes are engineered into plasmid or integration vectors (e.g., pJB1349) and assembled into a two gene operon (fadD-wxs) or a three gene operon (tesA-fadD-wxs) with flanking sites on the integration vector corresponding to integration sites for transformation into *Thermosynechococcus elongatus* BP-1. Integration sites include TS1, TS2, TS3 and TS4. A preferred integration site is the site of the aas gene. Host cells are cultured in the presence of small amounts of ethanol (1-10%) in the growth media under an appropriate promoter such as Pnir for the production of fatty acid esters.

In another embodiment, *Thermosynechococcus elongatus* BP-1 host cell with a two gene operon (fadD-wxs) or a three gene operon (tesA-fadD-wxs) is engineered to have ethanol producing genes (PCT/US2009/035937, filed Mar. 3, 2009; PCT/US2009/055949, filed Sep. 3, 2009; PCT/US2009/057694, filed Sep. 21, 2009) conferring the ability to produce fatty acid esters. In one plasmid construct, genes for ethanol production, including pyruvate decarboxylase from *Zymomonas mobilis* ($pdc_{Zm}$) and alcohol dehydrogenase from *Moorella* sp. HUC22-1 ($adhA_M$), are engineered into a plasmid and transformed into BP-1. In an alternate plasmid construct, the pyruvate decarboxylase from *Zymobacter palmae* ($pdc_{Zp}$) and alcohol dehydrogenase from *Moorella* sp. HUC22-1 ($adhA_M$), are engineered into a plasmid and transformed into BP-1. These genes are engineered into plasmid or integration vectors (e.g., pJB1349) with flanking sites on the integration vector corresponding to integration sites for transformation into *Thermosynechococcus elongatus* BP-1. Integration sites include TS1, TS2, TS3 and TS4. A preferred integration site is the site of the aas gene. In one configuration, expression of $pdcZm$ and $adhAM$ are driven by λ phage cI ("PcI") and pEM7 and in another expression strain driven by PcI and $PtRNA^{Glu}$. In one embodiment, a single promoter is used to control the expression of both genes. In another embodiment each gene expression is controlled by separate promoters with PaphII or Pcpcb controlling one and PcI controlling the other.

Example 9

*Synechococcus* sp. PCC 7002 (Δaas) with Various Thioesterases

Strain Construction.

DNA sequences for thioesterase genes tesA, fatB, fatB1, and fatB2 were obtained from Genbank and were purchased from DNA 2.0 following codon optimization, checking for secondary structure effects, and removal of any unwanted restriction sites. Thioesterase gene fatB_mat is a modified form of fatB with its leader sequence removed.

TABLE 19

Thioesterase sources

| Gene name | Organism origin | GenBank protein seq |
|---|---|---|
| tesA | *Escherichia coli* | AAC73596 |
| fatB | *Umbellularia californica* (California bay) | Q41635 |
| fatB1 | *Cinnamomum camphora* (camphor tree) | Q39473 |
| fatB2 | *Cuphea hookeriana* | AAC49269 |

The thioesterase genes were cloned into a pJB5 expression vector containing upstream and downstream regions of homology to aquI (SYNPCC7002_A1189), pAQ3, and pAQ4 by digesting the inserts and vectors individually with AscI and NotI restriction endonucleases (New England BioLabs) following known laboratory techniques. Digestions were isolated on 1% TAE agarose gel, purified using a Gel Extraction Kit (Qiagen), and ligated with T4 DNA Ligase (New England BioLabs) incubated at room temperature for one hour. The ligated product was transformed into NEB 5-alpha chemically competent *E. coli* cells (New England BioLabs) using standard techniques. Purified plasmid was extracted using the QIAprep Spin Miniprep kit (Qiagen) and constructs were confirmed by PCR.

*Synechococcus* sp. PCC 7002 (Δaas) was grown in 5 ml A+ liquid media with 25 µg/ml gentamicin in a glass test tube (37° C., 120 rpm, 2% $CO_2$) to $OD_{730}$ of 0.98-1.1. 500 µl of culture was combined with 1 µg purified plasmid in 1.5 ml microcentrifuge tubes and incubated in darkness 3-4 hours. Samples were then plated on A+ agar plates with 3 or 6 mM urea and incubated overnight 37° C. in the light. Selective antibiotics were introduced to the plates by placing stock solution spectinomycin under the agar at a final concentration of 10 µg/mL, and incubating to allow diffusion of the antibiotic. Plates were incubated at 37° C. with light until plates cleared and individual colonies formed. Plates were then moved to an illuminated incubator at 2% $CO_2$. Cultures were maintained on liquid or agar A+ media containing 3-6 mM urea with 25 µg/ml gentamicin, 100-200 µg/ml spectomycin, to promote plasmid segregation.

Thioesterase integration and attenuation was confirmed by PCR of whole-cell genomic DNA by a "culture PCR" protocol. Briefly, 100 µl of each culture was resuspended in 50 µl water or lysis buffer (96.8% diH$_2$O, 1% Triton X-100, 2% 1M tris pH 8.5, 0.2% 1M EDTA). 10 µl of each suspension were heated 10 min at 98° C. to lyse cells. 1 µl of lysate was used in 10 µl standard PCR reactions using Quick-Load Taq 2× Master Mix (New England BioLabs) or Platinum PCR Supermix HiFi (Invitrogen). PCR products showed correct bands for segregated aquI, pAQ4 and unsegregated (pAQ3) integrants.

Detection and Quantification of Free Fatty Acids in Strains.

Individual colonies were grown in A+ liquid media with 3 mM urea, 50 µg/ml gentamicin, 200 µg/ml spectomycin in glass test tubes (see Table 20). Cultures were maintained in liquid culture to promote segregation (37° C., 120 rpm, 2% CO$_2$). Liquid cultures were diluted to OD$_{730}$=0.2 in 5 ml A+ liquid media with 3 mM urea and no antibiotics in glass test tubes and incubated for seven days (37° C., 120 rpm, 2% CO$_2$). After one week, OD$_{730}$ was recorded and free fatty acids were extracted as follows:

Samples were acidified with 50 µl 1N HCl. 500 µl of 250 g/L methyl-β-cyclodextrin solution was added, and samples were transferred to 15-ml conical tubes after pulse-vortexing. 1 ml of 50 mg/L butylated hydroxytoluene in isooctane was added to each tube. Samples were vortexed 20 s and immediately centrifuged 5 min at 6000 RCF to fractionate. 500 µl of the isooctane layer were sub-sampled into a new tube and submitted for GC analysis.

Concentrations of octanoic acid, decanoic acid, lauric acid, myristic acid, palmitoleic acid, palmitic acid, oleic acid, stearic acid, and 1-nonadecene extractants were quantitated by gas chromatography/flame ionization detection (GC/FID). Unknown peak areas in biological samples were converted to concentrations via linear calibration relationships determined between known authentic standard concentrations and their corresponding GC-FID peak areas. Standards were obtained from Sigma. GC-FID conditions were as follows. An Agilent 7890A GC/FID equipped with a 7683 series autosampler was used. 1 µl of each sample was injected into the GC inlet (split 5:1, pressure: 20 psi, pulse time: 0.3 min, purge time: 0.2 min, purge flow: 15 ml/min) and an inlet temperature of 280° C. The column was a HP-5MS (Agilent, 30 m×0.25 mm×0.25 µm) and the carrier gas was helium at a flow of 1.0 ml/min. The GC oven temperature program was 50° C., hold one minute; 10° C./min increase to 280° C.; hold ten minutes.

GC results showed increased fatty acid secretion in the thioesterase strains relative to *Synechococcus* sp. PCC 7002 JCC138 (Table 20). The specific enrichment profile of each culture was thioesterase dependent (Table 21).

TABLE 20

Fatty acid secretion in tesA, fatB_mat strains

| Sample | Location | Promoter | Thioesterase | Δaas | OD$_{730}$ | Fatty Acids (% DCW in media) | Fatty acids (mg/ml) |
|---|---|---|---|---|---|---|---|
| JCC138 | — | — | — | — | 11.80 | 0.11 | 3.81 |
| JCC1648 | pAQ4 | P(nir07) | tesA | yes | 5.56 | 2.76 | 44.45 |
| JCC1751 | pAQ3 | P(nir07) | tesA | yes | 7.68 | 2.29 | 51.10 |
| JCC1755 | pAQ3 | P(nir07) | fatB_mat | yes | 3.92 | 1.79 | 20.38 |

TABLE 21

Fatty acids by type

| | % DCW of compounds | | | | | |
|---|---|---|---|---|---|---|
| Sample | Lauric | Myristic | Palmitoleic | Palmitic | Oleic | Stearic |
| JCC138 | 0.000 | 0.061 | 0.000 | 0.000 | 0.000 | 0.050 |
| JCC1648 | 0.342 | 1.557 | 0.238 | 0.000 | 0.260 | 0.360 |
| JCC1751 | 0.146 | 0.539 | 0.165 | 1.145 | 0.158 | 0.143 |
| JCC1755 | 0.940 | 0.224 | 0.289 | 0.143 | 0.197 | 0.000 |

Individual colonies of JCC1704, JCC1705, and JCC1706 were grown for three days in A+ liquid media with 3 mM urea, 25 µg/ml gentamicin, 100 µg/ml spectomycin in glass test tubes (37° C., 120 rpm, 2% CO$_2$). Cultures were diluted to OD$_{730}$=0.2 in 5 ml A+ liquid media with 3 mM urea and no antibiotics in glass test tubes and incubated at 37° C., 120 rpm, 2% CO$_2$. After 11 days, OD$_{730}$ was recorded and free fatty acids were extracted as follows:

Samples were acidified with 50 µl 1N HCl. 500 µl of 250 g/L methyl-β-cyclodextrin solution was added and samples were transferred to 15-ml conical tubes after pulse-vortexing. 1 ml of 50 mg/L butylated hydroxytoluene in isooctane was added to each tube. Samples were vortexed 20 s and immediately centrifuged 5 min at 6000 RCF to fractionate. 500 µl of the isooctane layer were sub-sampled into a new tube and submitted for GC analysis.

Concentrations of octanoic acid, decanoic acid, lauric acid, myristic acid, palmitoleic acid, palmitic acid, oleic acid, stearic acid, and 1-nonadecene extractants were quantitated by gas chromatograph/flame ionization detection (GC/FID). Unknown peak areas in biological samples were converted to concentrations via linear calibration relationships determined between known authentic standard concentrations and their corresponding GC-FID peak areas. Standards were obtained from Sigma. GC-FID conditions were as follows. An Agilent 7890A GC/FID equipped with a 7683 series autosampler was used. 1 µl of each sample was injected into the GC inlet (split 5:1, pressure: 20 psi, pulse time: 0.3 min, purge time: 0.2 min, purge flow: 15 ml/min) and an inlet temperature of 280° C. The column was a HP-5MS (Agilent, 30 m×0.25 mm×0.25 µm) and the carrier gas was helium at a flow of 1.0 ml/min. The GC oven temperature program was 50° C., hold one minute; 10° C./min increase to 280° C.; hold ten minutes.

GC results showed increased fatty acid secretion relative to JCC138 but to a lesser degree than tesA or fatB_mat (Table 22). The specific enrichment profile of each culture was thioesterase dependent (Table 23).

TABLE 22

Fatty acid secretion in fatB, fatB1, fatB2 strains

| Sample | Location | Promoter | Thioesterase | Δaas | OD$_{730}$ | Fatty Acids (% DCW in media) | Fatty acids (mg/ml) |
|---|---|---|---|---|---|---|---|
| JCC1648 | pAQ4 | P(nir07) | tesA | yes | 11.2 | 6.66 | 216.283 |
| JCC1648 | pAQ4 | P(nir07) | tesA | yes | 11.6 | 5.74 | 193.236 |
| JCC1704 | aquI | P(nir07) | fatB | yes | 15.80 | 0.39 | 17.72 |
| JCC1704 | aquI | P(nir07) | fatB | yes | 16.80 | 0.40 | 19.56 |
| JCC1705 | aquI | P(nir07) | fatB1 | yes | 15.6 | 0.42 | 19.19 |
| JCC1705 | aquI | P(nir07) | fatB1 | yes | 16.3 | 0.43 | 20.44 |
| JCC1706 | aquI | P(nir07) | fatB2 | yes | 17.5 | 0.40 | 20.25 |
| JCC1706 | aquI | P(nir07) | fatB2 | yes | 16.5 | 0.41 | 19.86 |

TABLE 23

Fatty acids by type

| | % DCW of compounds | | | | | |
|---|---|---|---|---|---|---|
| Sample | Lauric | Myristic | Palmitoleic | Palmitic | Oleic | Stearic |
| JCC1648 | 0.233 | 1.408 | 0.264 | 3.919 | 0.223 | 0.611 |
| JCC1648 | 0.201 | 1.196 | 0.183 | 3.564 | 0.131 | 0.470 |
| JCC1704 | 0.000 | 0.057 | 0.107 | 0.073 | 0.087 | 0.063 |
| JCC1704 | 0.000 | 0.062 | 0.113 | 0.073 | 0.094 | 0.060 |
| JCC1705 | 0.000 | 0.058 | 0.110 | 0.089 | 0.099 | 0.068 |
| JCC1705 | 0.000 | 0.058 | 0.107 | 0.092 | 0.101 | 0.074 |
| JCC1706 | 0.000 | 0.054 | 0.098 | 0.090 | 0.085 | 0.071 |
| JCC1706 | 0.000 | 0.056 | 0.106 | 0.086 | 0.100 | 0.068 |

Example 10

Fatty Acid Production Under Inducible or Repressible System

Construction of the Promoter-uidA Expression Plasmid.

The *E. coli* uidA gene (Genbank AAB30197) was synthesized by DNA 2.0 (Menlo Park, Calif.), and was subcloned into pJB5. The DNA sequences of the ammonia-repressible nitrate reductase promoters P(nirA) (SEQ ID NO:17), P(nir07) (SEQ ID NO:18), and P(nir09) (SEQ ID NO:19) were obtained from Genbank. The nickel-inducible P(nrsB) promoter (SEQ ID NO:20), nrsS and nrsR were amplified from *Synechocystis* sp. PCC 6803. The promoters were cloned between NotI and NdeI sites immediately upstream of uidA, which is flanked by NdeI and EcoRI.

In addition, plasmids containing two 750-bp regions of homology designed to remove the native aquI (A1189) or the ldh (G0164) gene from *Synechococcus* sp. PCC 7002 were obtained by contract synthesis from DNA 2.0 (Menlo Park, Calif.). Using these vectors, 4 constructs were engineered and tested for GUS activity. Final transformation constructs are listed in Table 24. All restriction and ligation enzymes were obtained from New England Biolabs (Ipswich, Mass.). Ligated constructs were transformed into NEB 5-α competent *E. coli* (High Efficiency) (New England Biolabs: Ipswich, Mass.).

TABLE 24

Genotypes of JCC138 transformants

| Insert location | Promoter | Marker |
|---|---|---|
| ldh | P(nirA) | kanamycin |
| aquI | P(nir07) | spectinomycin |
| aquI | P(nir09) | spectinomycin |
| ldh | P(nrsB) | kanamycin |

Plasmid Transformation into JCC138.

The constructs as described above were integrated onto either the genome or pAQ7 of JCC138, both of which are maintained at approximately 7 copies per cell. The following protocol was used for integrating the DNA cassettes. JCC138 was grown in an incubated shaker flask at 37° C. at 1% CO$_2$ to an OD$_{730}$ of 0.8 in A$^+$ medium. 500 µl of culture was added to a microcentrifuge tube with 1 µg of DNA. DNA was prepared using a Qiagen Qiaprep Spin Miniprep Kit (Valencia, Calif.) for each construct. Cells were incubated in the dark for one hour at 37° C. The entire volume of cells was plated on A$^+$ plates with 1.5% agar supplemented with 3 mM urea when necessary and grown at 37° C. in an illuminated incubator (40-60 µE/m2/s PAR, measured with a LI-250A light meter (LI-COR)) for approximately 24 hours. 25 µg/mL of spectinomycin or 50 µg/mL of kanamycin was introduced to the plates by placing the stock solution of antibiotic under the agar, and allowing it to diffuse up through the agar. After further incubation, resistant colonies became visible in 6 days. One colony from each plate was restreaked onto A$^+$ plates with 1.5% agar supplemented with 6 mM urea when necessary and 200 µg/mL spectinomycin or 50 µg/mL of kanamycin.

Measurement of GUS Activity.

The GUS (beta-glucuronidase) reporter system was used to test the inducibility or repressibility of several promoters. This system measures the activity of beta-glucuronidase, an enzyme from *E. coli* that transforms colorless or non-fluorescent substrates into colored or fluorescent products. In this case, MUG (4-methylumbelliferyl β-D-glucuronide) is the substrate, and is hydrolyzed by beta-glucuronidase to produce the florescent product MU (4-methylumbelliferone), which is subsequently detected and quantified with a fluorescent spectrophotometer.

Strains containing uidA constructs under urea repression were incubated to OD$_{730}$ between 1.8 and 4. These cells were subcultured to OD$_{730}$ 0.2 in 5 mL A+ media supplemented with 0, 3, 6, or 12 mM urea plus either 100 µg/mL spectinomycin or 50 µg/ml kanamycin and incubated for 24 hours. JCC138 was cultured in 5 mL A+ media for 24 hours. The strain containing gus under nickel-inducible expression was cultured for 3 days, then subcultured to OD$_{730}$ 0.2 in 5 mL A+ supplemented with 0, 2, 4, or 8 M NiSO$_4$. These cells were incubated for 6 hours. To harvest cells, cultures were spun for 5 minute at 6000 rpm. Pellets were resuspended in 1 mL 1×GUS extraction buffer (1 mM EDTA, 5.6 mM 2-mercaptoethanol, 0.1 M sodium phosphate, pH 7) and lysed with microtip sonication pulsing 0.5 seconds on and 0.5 seconds off for 2 min. Total protein was analyzed with Bio-Rad (Hercules, Calif.) Quick Start Bradford assay, and extracts were subsequently analyzed for GUS activity using a Sigma (St Louis, Mo.) β-Glucuronidase Fluorescent Activity Detection Kit. Relative activities of the 4 promoters are found in Table 25.

TABLE 25

GUS activities of inducible/repressible promoters

| promoter | mM urea | uM NiSO$_4$ | (ABS/mg × 10$^6$) |
|---|---|---|---|
| P(nirA) | 0 | — | 121.9 |
|  | 3 | — | 8 |
|  | 6 | — | 11.62 |
|  | 12 | — | 7.81 |
| P(nir07) | 0 | — | 396.39 |
|  | 3 | — | 23.61 |
|  | 6 | — | 30.89 |
|  | 12 | — | 33.13 |
| P(nir09) | 0 | — | 97.77 |
|  | 3 | — | 12.47 |
|  | 6 | — | 12.35 |
|  | 12 | — | 12.1 |
| P(nrsB) | — | 0 | 24.97 |
|  | — | 2 | 286.96 |
|  | — | 4 | 257.26 |
|  | — | 8 | 423.77 |
| no uidA gene | — | — | 6.4 |

A number of embodiments of the invention have been described. Nevertheless, it will be understood that various modifications may be made without departing from the spirit and scope of the invention. All publications, patents and other references mentioned herein are hereby incorporated by reference in their entirety.

REFERENCES

Cho, H. and Cronan, J. E. (1993) *The Journal of Biological Chemistry* 268: 9238-9245.
Chollet, R et al. (2004) *Antimicrobial Agents and Chemotherapy* 48: 3621-3624.
Kalscheuer, R., et al. (2006a) *Microbiology* 152: 2529-2536.
Kalscheuer, R. et al. (2006b) *Applied and Environmental Microbiology* 72: 1373-1379.
Kameda, K. and Nunn, W. D. (1981) *The Journal of Biological Chemistry* 256: 5702-5707.
Lopez-Mauy et al., *Cell* (2002) v.43:247-256
Nielsen, D. R et al. (2009) *Metabolic Engineering* 11: 262-273.
Qi et al., *Applied and Environmental Microbiology* (2005) v.71: 5678-5684
Stöveken, T. et al. (2005) *Journal of Bacteriology* 187:1369-1376
Tsukagoshi, N. and Aono, R. (2000) *Journal of Bacteriology* 182: 4803-4810

INFORMAL SEQUENCE LISTING

SEQ ID NO: 1
E. coli TesA amino acid sequence (leader sequence removed)
MADTLLILGDSLSAGYRMSASAAWPALLNDKWQSKTSVVNASISGDTSQQGLARLPAL
LKQHQPRWVLVELGGNDGLRGFQPQQTEQTLRQILQDVKAANAEPLLMQIRLPANYGR
RYNEAFSAIYPKLAKEFDVPLLPFFMEEVYLKPQWMQDDGIHPNRDAQPFIADWMAKQ
LQPLVNHDS SEQ ID NO: 2
E. coli FadD amino acid sequence
MKKVWLNRYPADVPTEINPDRYQSLVDMFEQSVARYADQPAFVNMGEVMTFRKLEER
SRAFAAYLQQGLGLKKGDRVALMMPNLLQYPVALGILRAGMIVVNVNPLYTPRELEH
QLNDSGASAIVIVSNFAHTLEKVVDKTAVQHVILTRMGDQLSTAKGTVVNFVVKYIKRL
VPKYHLPDAISFRSALHNGYRMQYVKPELVPEDLAFLQYTGGTTGVAKGAMLTHRNM
LANLEQVNATYGPLLHPGKELVVTALPLYHIFALTINCLLFIELGGQNLLITNPRDIPGLV
KELAKYPFTAITGVNTLFNALLNNKEFQQLDPSSLHLSAGGGMPVQQVVAERWVKLTG
QYLLEGYGLTECAPLVSVNPYDIDYHSGSIGLPVPSTEAKLVDDDDNEVPPGQPGELCV
KGPQVMLGYWQRPDATDEIIKNGWLHTGDIAVMDEEGFLRIVDRKKDMILVSGFNVYP
NEIEDVVMQHPGVQEVAAVGVPSGSSGEAVKIFVVKKDPSLTEESLVTFCRRQLTGYKV
PKLVEFRDELPKSNVGKILRRELRDEARGKVDNKA SEQ ID NO: 3
A. baylyi ADP1 wax synthase amino acids sequence
MRPLHPIDFIFLSLEKRQQPMHVGGLFLFQIPDNAPDTFIQDLVNDIRISKSIPVPPFNNKL
NGLFWDEDEEFDLDHHFRHIALPHPGRIRELLIYISQEHSTLLDRAKPLWTCNIIEGIEGNR
FAMYFKIHHAMVDGVAGMRLIEKSLSHDVTEKSIVPPWCVEGKRAKRLREPKTGKIKKI
MSGIKSQLQATPTVIQELSQTVFKDIGRNPDHVSSFQAPCSILNQRVSSSRRFAAQSFDLD
RFRNIAKSLNVTINDVVLAVCSGALRAYLMSHNSLPSKPLIAMVPASIRNDDSDVSNRIT
MILANLATHKDDPLQRLEIIRRSVQNSKQRFKRMTSDQILNYSAVVYGPAGLNIISGMMP
KRQAFNLVISNVPGPREPLYWNGAKLDALYPASIVLDGQALNITMTSYLDKLEVGLIAC
RNALPRMQNLLTHLEEEIQLFEGVIAKQEDIKTAN SEQ ID NO: 4
E. coli tesA optimized nucleic acid sequence
ATGGCGGATACTCTGCTGATTCTGGGTGATTCTCTGTCTGCAGGCTACCGTATGTCCG
CCTCCGCGGCCTGGCCAGCTCTGCTGAATGATAAGTGGCAGTCTAAGACGTCCGTTG

```
TGAACGCATCCATCTCTGGCGACACGAGCCAGCAGGGCCTGGCCCGTCTGCCTGCAC
TGCTGAAACAGCACCAACCGCGCTGGGTCCTGGTGGAGCTGGGCGGTAACGACGGT
CTGCGCGGCTTCCAGCCGCAGCAGACCGAACAGACTCTGCGTCAGATTCTGCAGGA
CGTGAAAGCTGCTAACGCGGAACCGCTGCTGATGCAGATTCGTCTGCCAGCGAACT
ATGGCCGCCGTTACAACGAAGCGTTCTCTGCAATCTACCCAAAACTGGCGAAAGAG
TTTGACGTCCCGCTGCTGCCGTTCTTCATGGAGGAAGTATACCTGAAACCGCAGTGG
ATGCAAGATGACGGCATCCACCCGAACCGTGATGCGCAGCCGTTCATCGCTGACTG
GATGGCGAAGCAACTGCAGCCGCTGGTAAACCACGATTCCTAA
```

SEQ ID NO: 5

E. coli fadD optimized nucleic acid sequence
```
ATGAAGAAAGTTTGGCTGAACCGTTATCCGGCAGATGTACCGACTGAAATTAACCC
AGATCGTTACCAGTCCCTGGTTGACATGTTCGAACAGTCCGTGGCTCGCTACGCCGA
TCAGCCTGCTTTCGTCAACATGGGTGAGGTAATGACCTTTCGCAAACTGGAGGAGCG
TTCCCGTGCTTTCGCGGCATACCTGCAGCAGGGTCTGGGCCTGAAGAAAGGCGACC
GCGTGGCCCTGATGATGCCGAACCTGCTGCAATATCCTGTGGCGCTGTTCGGTATCC
TGCGTGCTGGTATGATCGTTGTCAATGTTAACCCTCTGTATACCCCTCGTGAACTGGA
GCACCAGCTGAATGACTCTGGTGCGTCTGCTATCGTTATCGTTTCCAATTTCGCACAT
ACGCTGGAGAAAGTGGTTGATAAAACCGCAGTGCAGCATGTCATTCTGACTCGCAT
GGGTGACCAGCTGTCCACCGCTAAAGGTACTGTAGTCAACTTCGTTGTTGAAATACAT
TAAGCGCCTGGTTCCGAAATACCACCTGCCAGATGCAATTAGCTTTCGCTCTGCACT
GCATAACGGTTACCGTATGCAGTACGTAAAACCAGAGCTGGTGCCGGAAGACCTGG
CCTTTCTGCAGTATACCGGCGGCACCACCGGCGTGGCAAAGGGCGCGATGCTGACC
CATCGTAACATGCTGGCGAACCTGGAGCAGGTTAACGCAACGTACGGCCCCGCTGCT
GCACCCGGGTAAAGAACTGGTAGTTACGGCACTGCCTCTGTATCACATCTTTGCACT
GACGATCAACTGTCTGCTGTTCATTGAACTGGGTGGTCAGAACCTGCTGATCACCAA
CCCGCGTGACATTCCGGGCCTGGTAAAAGAGCTGGCTAAGTACCCGTTCACCGCCAT
TACTGGCGTAAACACTCTGTTTAACGCGCTGCTGAACAACAAAGAGTTTCAGCAGCT
GGACTTCTCTAGCCTGCACCTGAGCGCTGGCGGTGGCATGCCGGTTCAGCAGGTTGT
GGCAGAGCGTTGGGTGAAACTGACCGGCCAGTATCTGCTGGAGGGTTATGGTCTGA
CCGAGTGTGCACCGCTGGTCAGCGTTAACCCGTATGATATTGATTACCACTCTGGTT
CTATTGGTCTGCCGGTTCCGTCCACGAAGCCAAACTGGTGGACGATGACGACAAC
GAAGTACCTCCGGGCCAGCCGGGTGAGCTGTGTGTCAAGGGTCCGCAGGTTATGCT
GGGCTACTGGCAGCGCCCGGACGCCACCGACGAAATCATTAAAAACGGTTGGCTGC
ATACCGGTGATATCGCTGTAATGGACGAAGAAGGTTTCCTGCGTATCGTGGACCGTA
AGAAAGATATGATTCTGGTGAGCGGTTTCAACGTGTACCCGAACGAAATTGAGGAC
GTAGTTATGCAACACCCTGGCGTGCAGGAGGTGGCAGCCGTGGGCGTGCCGTCCGG
TTCTTCTGGTGAGGCTGTGAAAATCTTTGTCGTTAAAAAGGACCCGTCCCTGACCGA
AGAATCTCTGGTGACGTTTTGCCGCCGTCAACTGACTGGCTACAAAGTGCCGAAACT
GGTCGAGTTCCGCGATGAGCTGCCAAAATCTAACGTGGGTAAGATCCTGCGCCGCG
AGCTGCGTGACGAGGCACGTGGCAAAGTTGACAATAAAGCATAA
```

SEQ ID NO: 6

A. baylyi wsadp1 optimized nucleic acid sequence
```
ATGCGCCCACTTCATCCGATCGATTTCATTTTCCTGTCCGTGGAGAAACGCCAGCAG
CCGATGCACGTAGGTGGTCTGTTCCTGTTCCAGATCCCGGATAACGCTCCGGACACC
TTTATTCAGGACCTGGTGAACGATATCCGTATCTCCAAGTCTATTCCGGTTCCGCCGT
TCAACAACAAGCTGAACGGTCTGTTCTGGGACGAAGACGAGGAGTTCGATCTGGAT
CACCATTTCCGTCATATTGCGCTGCCGCACCCGGGTCGCATCCGTGAGCTGCTGATT
TACATCTCTCAGGAACACAGCACTCTCCTCGATCGCGCTAAACCTCTGTGGACTTGC
AACATCATTGAAGGTATCGAGGGTAACCGTTTCGCCATGTACTTCAAGATTCATCAT
GCGATGGTGGATGGTGTGGCGGGTATGCGTCTGATTGAGAAAAGCCTGTCCCATGAT
GTTACTGAAAAGAGCATCGTACCGCCGTGGTGCGTTGAGGGCAAACGTGCTAAACG
CCTGCGTGAACCGAAGACCGGCAAAATTAAGAAAATCATGTCTGGTATTAAATCTC
AGCTCCAGGCCACCCCGACCGTTATTCAAGAACTGTCTCAGACGGTCTTCAAAGACA
TCGGCCGTAATCCGGACCACGTTTCCTCTTTCCAGGCGCCGTGCTCCATCCTCAACC
AGCGTGTGTCTTCTTCGTCGTTTCGCAGCACAGAGCTTTGACCTGGACCGTTTCCG
CAACATCGCCAAATCTCTGAACGTGACCATTAACGACGTTGTCCTGGCTGTGTGTAG
CGGTGCTCTGCGCGCTTATCTGATGTCTCATAACTCTCTGCCATCCAAACCGCTGATC
GCTATGGTCCCAGCAAGCATCCGCAACGATGATTCTGATGTGTCCAACCGTATTACT
ATGATTCGGCCAACCTCGCTACTCACAAAGACGACCCTCTGCAGCGTCTGGAAATC
ATCCGCCGCTCCGTCCAGAACTCTAAACAGCGTTTTAAACGCATGACTTCCGACCAG
ATTCTGAACTATTCTGCGGTTGTATACGGCCCGGCTGGTCTGAACATTATCAGCGGT
ATGATGCCGAAACGTCAGGCTTTTAACCTGGTAATCAGCAACGTTCCTGGCCCGCGT
GAGCCGCTGTACTGGAACGGCGCAAAACTGGACGCACTGTACCCGGCTTCCATCGTT
CTGGATGCCAGGCTCTGAACATCACTATGACCTCTTACCTGGACAAACTGGAAGTA
GGTCTGATCGCGTGTCGCAATGCACTGCCGCGCATGCAGAACCTGCTGACCCACCTG
GAGGAGGAAATCCAGCTGTTTGAGGGCGTTATCGCCAAACAGGAAGATATCAAAAC
GGCGAACTAA
```

SEQ ID NO: 7

E. coli TolC amino acid sequence
```
MKKLLPILIGLSLSGFSSLSQAENLMQVYQQARLSNPELRKSAADRDAAFEKINEARSPL
LPQLGLGADYTYSNGYRDANGINSNATSASLQLTQSIFDMSKWRALTLQEKAAGIQDVT
YQTDQQTLILNTATAYFNVLNAIDVLSYTQAQKEAIYRQLDQTTQRFNVGLVAITDVQN
ARAQYDTVLANEVTARNNLDNAVEQLRQITGNYYPELAALNVENFKTDKPQPVNALLK
EAEKRNLSLLQARLSQDLAREQIRQAQDGHLPTLDLTASTGISDTSYSGSKTRGAAGTQ
```

```
                        INFORMAL SEQUENCE LISTING

YDDSNMGQNKVGLSFSLPIYQGGMVNSQVKQAQYNFVGASEQLESAHRSVVQTVRSSF
NNINASISSINAYKQAVVSAQSSLDAMEAGYSVGTRTIVDVLDATTTLYNAKQELANAR
YNYLINQLNIKSALGTLNEQDLLALNNALSKPVSTNPENVAPQTPEQNAIADGYAPDSPA
PVVQQTSARTTTSNGHNPFRN

SEQ ID NO: 8
E. coli AcrA amino acid sequence
MNKNRGFTPLAVVLMLSGSLALTGCDDKQAQQGGQQMPAVGVVTVKTEPLQITTELP
GRTSAYRIAEVRPQVSGIILKRNFKEGSDIEAGVSLYQIDPATYQATYDSAKGDLAKAQA
AANIAQLTVNRYQKLLGTQYISKQEYDQALADAQQANAAVTAAKAAVETARINLAYT
KVTSPISGRIGKSNVTEGALVQNGQATALATVQQLDPIYVDVTQSSNDFLRLKQELANG
TLKQENGKAKVSLITSDGIKFPQDGTLEFSDVTVDQTTGSITLRAIFPNPDHTLLPGMFVR
ARLEEGLNPNAILVPQQGVTRTPRGDATVLVVGADDKVETRPIVASQAIGDKWLVTEGL
KAGDRVVISGLQKVRPGVQVKAQEVTADNNQQAASGAQPEQSKS SEQ ID NO: 9
E. coli AcrB amino acid sequence
MPNFFIDRPIFAWVIAIIIMLAGGLAILKLPVAQYPTIAPPAVTISASYPGADAKTVQDTVT
QVIEQNMNGIDNLMYMSSNSDSTGTVQITLTFESGTDADIAQVQVQNKLQLAMPLLPQE
VQQQGVSVEKSSSSFLMVVGVINTDGTMTQEDISDYVAANMKDAISRTSGVGDVQLFG
SQYAMRIWMNPNELNKFQLTPVDVITAIKAQNAQVAAGQLGGTPPVKGQQLNASIIAQT
RLTSTEEFGKILLKVNQDGSRVLLRDVAKIELGGENYDIIAEFNGQPASGLGIKLATGAN
ALDTAAAIRAELAKMEPFFPSGLKIVYPYDTTPFVKISIHEVVKTLVEAIILVFLVMYLFL
QNFRATLIPTIAVPVVLLGTFAVLAAFGFSINTLTMFGMVLAIGILVDDAIVVVENVERV
MAEEGLPPKEATRKSMGQIQGALVGIAMVLSAVFVPMAFFGGSTGAIYRQFSITIVSAM
ALSVLVALILTPALCATMLKPIAKGDHGEGKKGFFGWFNRMFEKSTHHYTDSVGGILRS
TGRYLVLYLIIVVGMAYLFVRLPSSFLPDEDQGVFMTMVQLPAGATQERTQKVLNEVT
HYYLTKEKNNVESVFAVNGFGFAGRGQNTGIAFVSLKDWADRPGEENKVEAITMRATR
AFSQIKDAMVFAFNLPAIVELGTATGFDFELIDQAGLGHEKLTQARNQLLAEAAKHPDM
LTSVRPNGLEDTPQFKIDIDQEKAQALGVSINDINTTLGAAWGGSYVNDFIDRGRVKKV
YVMSEAKYRMLPDDIGDWYVRAADGQMVPFSAFSSSRWEYGSPRLERYNGLPSMEILG
QAAPGKSTGEAMELMEQLASKLPTGVGYDWTGMSYQERLSGNQAPSLYAISLIVVFLC
LAALYESWSIPFSVMLVVPLGVIGALLAATFRGLTNDVYFQVGLLTTIGLSAKNAILIVEF
AKDLMDKEGKGLIEATLDAVRMRLRPILMTSLAFILGVMPLVISTGAGSGAQNAVGTGV
MGGMVTATVLAIFFVPVFFVVRRRFSRKNEDIEHSHTVDHH SEQ ID NO: 10
PaphII underlined; tesA, fadD and wsadp1 are in bold and follow the
promoter in order
GCGGCCGCGGGGGGGGGGGAAAGCCACGTTGTGTCTCAAAATCTCTGATGTTACATTGCACAAGAT
AAAAATATATCATCATGAACAATAAAACTGTCTGCTTACATAAACAGTAATACAAGGGGTCATATGG
CGGATACTCTGCTGATTCTGGGTGATTCTCTGTCTGCAGGCTACCGTATGTCCGCCTCCGCGGC
CTGGCCAGCTCTGCTGAATGATAAGTGGCAGTCTAAGACGTCCGTTGTGAACGCATCCATCTCT
GGCGACACGAGCCAGCAGGGCCTGGCCCGTCTGCCTGCACTGCTGAAACAGCACCAACCGCGC
TGGGTCCTGGTGGAGCTGGGCGGTAACGACGGTCTGCGCGGCTTCAGCCGCAGCAGACCGAA
CAGACTCTGCGTCAGATTCTGCAGGACGTGAAAGCTGCTAACGCGGAACCGCTGCTGATGCAGA
TTCGTCTGCCAGCGAACTATGCCGCCGTTACAACGAAGCGTTCTCTGCAATCTACCCAAAACT
GGCGAAAGAGTTTGACGTCCCGCTGCTGCCGTTCTTCATGGAGGAAGTATACCTGAAACCGCAG
TGGATGCAAGATGACGGCATCCACCCGAACCGTGATGCGCAGCCGTTCATCGCTGACTGGATGG
CGAAGCAACTGCAGCCGCTGGTAAACCACGATTCCTAATTAAAGATCTGTAGTAGGATCCATGTAG
GGTGAGGTTATAGCTATGAAGAAAGTTTGGCTGAACCGTTATCCGGCAGATGTACCGACTGAAAT
TAACCCAGATCGTTACCAGTCCCTGGTTGACATGTTCGAACAGTCCGTGGCTCGCTACGCCGAT
CAGCCTGCTTTCGTCAACATGGGTGAGGTAATGACCTTTCGCAAACTGGAGGAGCGTTCCGGTG
CTTTCGCGGCATACCTGCAGCAGGGTCTGGGCCTGAAGAAAGGCGACCGCGTGGCCCTGATGAT
GCCGAACCTGCTGCAATATCCTGTGGCGCTGTTCGGTATCCTGCGTGCTGGTATGATCGTTGTC
AATGTTAACCCTCTGTATACCCCTCGTGAACTGGAGCACCAGCTGAATGACTCTGGTGCGTCTG
CTATCGTTATCGTTTCCAATTTCGCACATACGCTGGAGAAAGTGGTTGATAAAACCGCAGCAG
CATGTCATTCTGACTCGCATGGGTGACCAGCTGTCCACCGCTAAAGGTACTGTAGTCAACTTCGT
TGTGAAATACATTAAGCGCCTGGTTCCGAAATACCACCTGCCAGATGCAATTAGCTTTCGCTCTG
CACTGCATAACGGTTACCGTATGCAGTACGTAAAACCAGAGCTGGTGCCGGAAGACCTGGCCTT
TCTGCAGTATACCGGCGGCACCACCGGCGTGGCAAAGGGCGATGCTGACCCATCGTAACATG
CTGGCGAACCTGGAGCAGGTTAACGCAACGTACGGCCCGCTGCTGCACCCGGGTAAAGAACTG
GTAGTTACGGCACTGCCTCTGTATCACATCTTTGCACTGACGATCAACTGTCTGCTGTTCATTGA
ACTGGGTGGTCAGAACCTGCTGATCACCAACCCGCGTGACATTCCGGGCCTGGTAAAAGAGCTG
GCTAAGTACCCGTTCACCGCCATTACTGGCGTAAACACTCTGTTTAACGCGCTGCTGAACAACAA
AGAGTTTCAGCAGCTGGACTTCTCTAGCCTGCACCTGAGCGCTGGCGGTGGCATGCCGGTTCAG
CAGGTTGTGGCAGAGCGTTGGGTGAAACTGACCGGCCAGTATCTGCTGGAGGGTTATGGTCTGA
CCGAGTGTGCACCGCTGGTCAGCGTTAACCCGTATGATATTGATTACCACTCTGGTTCTATTGGT
CTGCCGGTTCCGTCCACGGAAGCCAAACTGGTGGACGATGACGACAACGAAGTACCTCCGGGCC
AGCCGGGTGAGCTGTGTGTCAAGGGTCCGCAGGTTATGCTGGGCTACTGGCAGCGCCCGGACG
CCACCGACGAAATCATTAAAAACGGTTGGCTGCATACCGGTGATATCGTCTGTAATGACGAAGA
AGGTTTCCTGCGTATCGTGGACCGTAAGAAAGATATGATTCTGGTGAGCGGTTTCAACGTGTAC
CCGAACGAAATTGAGGACTAGTTATGCAACACCCTGGCGTGCAGGAGGTGGCAGCCGTGGGC
GTGCCGTCCGGTTCTTCTGGTGAGGCTGTGAAATCTTTGTCGTTAAAAGGACCCGTCCCTGA
CCGAAGAATCTCTGGTGACGTTTTGCCGCCGTCAACTGACTGGCTACAAAGTGCCGAAACTGGT
CGAGTTCCGCGATGAGCTGCCAAAATCTAACGTGGGTAAGATCCTGCGCCGCGAGCTGCGTGAC
GAGGCACGTGGCAAAGTTGACAATAAAGCATAACCGCGTAGGAGGACAGCTATGCGCCCACTTCA
```

```
TCCGATCGATTTCATTTTCCTGTCCCTGGAGAAACGCCAGCAGCCGATGCACGTAGGTGGTCTG
TTCCTGTTCCAGATCCCGGATAACGCTCCGGACACCTTTATTCAGGACCTGGTGAACGATATCCG
TATCTCCAAGTCTATTCCGGTTCCGCCGTTCAACAACAAGCTGAACGGTCTGTTCTGGGACGAA
GACGAGGAGTTCGATCTGGATCACCATTTCCGTCATATTGCGCTGCCGCACCCGGGTCGCATCC
GTGAGCTGCTGATTTACATCTCTCAGGAACACAGCACTCTCCTCGATCGCGCTAAACCTCTGTGG
ACTTGCAACATCATTGAAGGTATCGAGGGTAACCGTTTCGCCATGTACTTCAAGATTCATCATGC
GATGGTGGATGGTGTGGCGGGTATGCGTCTGATTGAGAAAAGCCTGTCCCATGATGTTACTGAA
AAGAGCATCGTACCGCCGTGGTGCGTTGAGGGCAAACGTGCTAAACGCCTGCGTGAACCGAAG
ACCGGCAAAATTAAGAAAATCATGTCTGGTATTAAATCTCAGCTCCAGGCCACCCCGACCGTTAT
TCAAGAACTGTCTCAGACGGTCTTCAAAGACATCGGCCGTAATCCGGACCACGTTTCCTCTTTCC
AGGCGCCGTGCTCCATCCTCAACCAGCGTGTGTCTTCTTTCCGTCGTTTCGCAGCACAGAGCTTT
GACCTGGACCGTTTCCGCAACATCGCCAAATCTCTGAACGTGACCATTAACGACGTTGTCCTGG
CTGTGTGTAGCGGTGCTCTGCGCGCTTATCTGATGTCTCATAACTCTCTGCCATCCAAACCGCTG
ATCGCTATGGTCCCAGCAAGCATCCGAACGATGATTCTGATGTGTCCAACCGTATTACTATGAT
TCTGGCCAACCTCGCTACTCACAAAGACGACCCTCTGCAGCGTCTGGAAATCATCCGCCGCTCC
GTCCAGAACTCTAAACAGCGTTTTAAACGCATGACTTCCGACCAGATTCTGAACTATTCTGCGGT
TGTATACGGCCCGGCTGGTCTGAACATTATCAGCGGTATGATGCCGAAACGTCAGGCTTTTAAC
CTGGTAATCAGCAACGTTCCTGGCCCGCGTGAGCCGCTGTACTGGAACGGCGCAAAACTGGACG
CACTGTACCCGGCTTCCATCGTTCTGGATGGCCAGGCTCTGAACATCACTATGACCTCTTACCTG
GACAAACTGGAAGTAGGTCTGATCGCGTGTCGCAATGCACTGCCGCGCATGCAGAACCTGCTGA
CCCACCTGGAGGAGGAAATCCAGCTGTTTGAGGGCGTTATCGCCAAACAGGAAGATATCAAAAC
GGCGAACTAACCATGGTTGAATTC
```

SEQ ID NO: 11
pJB532 (UHR and DHR are lowercase; lacIq with promoter and P<sub>trc</sub>
underlined; tesA, fadD and wsadp1 are in bold and underlined and
follow the promoter in order; aadA marker is italicized and underlined)

```
CCTGCAGGGtcagcaagctctggaatttcccgattctctgatgggagatccaaaaattctcgcagtccctc
aatcacgatatcggtatggatcgccctgtagcttccgacaactgctcaatttttttcgagcatctctaccgg
gcatcggaatgaaattaacggtgttttagccatgtgttatacagtgtttacaacttgactaacaaataccct
gctagtgtatacatattgtattgcaatgtatacgctattttcactgctgtctttaatggggattatcgcaa
gcaagtaaaaaagcctgaaaacccaataggtaagggattccgagcttactcgataattatcacattgagc
gccctaggaggaggcgaaaagctatgtagacaaggggtttgaccctgaagtcgttgcgcgagcattaag
gtctgcggatagccataacatactttgttgaacttgtgcgcttttatcaaccccttaagggcttgggag
cgttttatGCGGCCGCTCACTGCCCGCTTTCCAGTCGGGAAACCTGTCGTGCCAGCTGCATTAATGAATCG
GCCAACGCGCGGGAGAGGCGGTTTGCGTATTGGGCGCCAGGGTGGTTTTTCTTTTCACCAGTG
AGACGGGCAACAGCTGATTGCCCTTCACCGCCTGGCCCTGAGAGAGTTGCAGCAAGCGGTC
CACGCTGGTTTGCCCCAGCAGGCGAAAATCCTGTTTGATGGTGGTTGACGGCGGGATATAAC
ATGAGCTGTCTTCGGTATCGTCGTATCCCACTACCGAGATATCCGCACCAACGCGCAGCCCG
GACTCGGTAATGGCGCGCATTGCGCCCAGCGCCATCTGATCGTTGGCAACCAGCATCGCAGT
GGGAACGATGCCCTCATTCAGCATTTGCATGGTTTGTTGAAAACCGGACATGGCACTCCAGT
CGCCTTCCCGTTCCGCTATCGGCTGAATTTGATTGCGAGTGAGATATTTATGCCAGCCAGCCA
GACGCAGACGCGCCGAGACAGAACTTAATGGGCCCGCTAACAGCGCGATTTGCTGGTGACC
CAATGCGACCAGATGCTCCACGCCCAGTCGCGTACCGTCTTCATGGGAGAAAATAATACTGT
TGATGGGTGTCTGGTCAGAGACATCAAGAAATAACGCCGGAACATTAGTGCAGGCAGCTTC
CACAGCAATGGCATCCTGGTCATCCAGCGGATAGTTAATGATCAGCCCACTGACGCGCTGCG
CGAGAAGATTGTGCACCGCCGCTTTACAGGCTTCGACGCCGCTTCGTTCTACCATCGACACC
ACCACGCTGGCACCCAGTTGATCGGCGCGAGATTTAATCGCCGCGACAATTTGCGACGGCGC
GTGCAGGGCCAGACTGGAGGTGGCAACGCCAATCAGCAACGACTGTTTGCCCGCCAGTTGTT
GTGCCACGCGGTTGGGAATGTAATTCAGCTCCGCCATCGCCGCTTCCACTTTTTCCCGCGTTT
TCGCAGAAACGTGGCTGGCCTGGTTCACCACGCGGGAAACGGTCTGATAAGAGACACCGGC
ATACTCTGCGACATCGTATAACGTTACTGGTTTCATATTCACCACCCTGAATTGACTCTCTTC
CGGGCGCTATCATGCCATACCGCGAAAGGTTTTGCACCATTCGATGGTGTCAACGTAAATGC
ATGCCGCTTCGCCTTCCAATTGGACTGCACGGTGCACCAATGCTTCTGGCGTCAGGCAGCCA
TCGGAAGCTGTGGTATGGCTGTGCAGGTCGTAAATCACTGCATAATTCGTGTCGCTCAAGGC
GCACTCCCGTTCTGGATAATGTTTTTTGCGCCGACATCATAACGGTTCTGGCAAATATTCTGA
AATGAGCTGTTGACAATTAATCATCCGGCTCGTATAATGTGTGGAATTGTGAGCGGATAACA
ATTTCACACAGGAAACAGCATGGCCAAGGAGGCCCATATGGCGGATACTCTGCTGATTCT
GGGTGATTCTCTGTCTGCAGGCTACCGTATGTCCGCCTCCGCGGCCTGGCCAGCTCTG
CTGAATGATAAGTGGCAGTCTAAGACGTCCGTTGTGAACGCATCCATCTCTGGCGACA
CGAGCCAGCAGGGCCTGGCCCGTCTGCCTGCACTGCTGAAACAGCACCAACCGCGCTG
GGTCCTGGTGGAGCTGGGCGGTAACGACGGTCTGCGCGGCTTCCAGCCGCAGCAGAC
CGAACAGACTCTGCGTCAGATTCTGCAGGACGTGAAAGCTGCTAACGCGGAACCGCTG
CTGATGCAGATTCGTCTGCCAGCGAACTATGGCCGCCGTTACAACGAAGCGTTCTCTG
CAATCTACCCAAAACTGGCGAAAGAGTTTGACGTCCCGCTGCTGCCGTTCTTCATGGA
GGAAGTATACCTGAAACCGCAGTGGATGCAAGATGACGGCATCCACCCGAACCGTGAT
GCGCAGCCGTTCATCGCTGACTGGATGGCGAAGCAACTGCAGCCGCTGGTAAACCACG
ATTCCTAATTAAAGATCTGTAGTAGGATCCATGTAGGGTGAGGTTATAGCTATGAAGAAAG
TTTGGCTGAACCGTTATCCGGCAGATGTACCGACTGAAATTAACCCAGATCGTTACCAG
TCCCTGGTTGACATGTTCGAACAGTCCGTGGCTCGCTACGCCGATCAGCCTGCTTTCGT
CAACATGGGTGAGGTAATGACCTTTCGCAAACTGGAGGAGCGTTCCCGTGCTTTCGCG
GCATACCTGCAGCAGGGTCTGGGCCTGAAGAAAGGCGACCGCGTGGCCCTGATGATG
CCGAACCTGCTGCAATATCCTGTGGCGCTGTTCGGTATCCTGCGTGCTGGTATGATCG
TTGTCAATGTTAACCCTCTGTATACCCCTCGTGAACTGGAGCACCAGCTGAATGACTCT
GGTGCGTCTGCTATCGTTATCGTTTCCAATTTCGCACATACGCTGGAAAAGTGGTTGA
TAAAACCGCAGTGCAGCATGTCATTCTGACTCGCATGGGTGACCAGCTGTCCACCGCT
AAAGGTACTGTAGTCAACTTCGTTGTGAAATACATTAAGCGCCTGGTTCCGAAATACCA
```

INFORMAL SEQUENCE LISTING

```
CCTGCCAGATGCAATTAGCTTTCGCTCTGCACTGCATAACGGTTACCGTATGCAGTACG
TAAAACCAGAGCTGGTGCCGGAAGACCTGGCCTTTCTGCAGTATACCGGCGGCACCAC
CGGCGTGGCAAAGGGCGCGATGCTGACCCATCGTAACATGCTGGCGAACCTGGAGCA
GGTTAACGCAACGTACGGCCCGCTGCTGCACCCGGGTAAAGAACTGGTAGTTACGGCA
CTGCCTCTGTATCACATCTTTGCACTGACGATCAACTGTCTGCTGTTCATTGAACTGGG
TGGTCAGAACCTGCTGATCACCAACCCGCGTGACATTCCGGGCCTGGTAAAAGAGCTG
GCTAAGTACCCGTTCACCGCCATTACTGGCGTAAACACTCTGTTTAACGCGCTGCTGAA
CAACAAAGAGTTTCAGCAGCTGGACTTCTCTAGCCTGCACCTGAGCGCTGGCGGTGGC
ATGCCGGTTCAGCAGGTTGTGGCAGAGCGTTGGGTGAAACTGACCGGCCAGTATCTGC
TGGAGGGTTATGGTCTGACCGAGTGTGCACCGCTGGTCAGCGTTAACCCGTATGATAT
TGATTACCACTCTGGTTCTATTGGTCTGCCGGTTCCGTCCACGGAAGCCAAACTGGTG
GACGATGACGACAACGAAGTACCTCCGGGCCAGCCGGGTGAGCTGTGTGTCAAGGGT
CCGCAGGTTATGCTGGGCTACTGGCAGCGCCCGGACGCCACCGACGAAATCATTAAAA
ACGGTTGGCTGCATACCGGTGATATCGCTGTAATGGACGAAGAAGGTTTCCTGCGTAT
CGTGGACCGTAAGAAAGATATGATTCTGGTGAGCGGTTTCAACGTGTACCCGAACGAA
ATTGAGGACGTAGTTATGCAACACCCTGGCGTGCAGGAGGTGGCAGCCGTGGCGTG
CCGTCCGGTTCTTCTGGTGAGGCTGTGAAAATCTTTGTCGTTAAAAAGGACCCGTCCCT
GACCGAAGAATCTCTGGTGACGTTTTGCCGCCGTCAACTGACTGGCTACAAAGTGCCG
AAACTGGTCGAGTTCCGCGATGAGCTGCCAAAATCTAACGTGGGTAAGATCCTGCGCC
GCGAGCTGCGTGACGAGGCACGTGGCAAAGTTGACAATAAAGCATAACCGCGTAGGAG
GACAGCTATGCGCCCACTTCATCCGATCGATTTCATTTTCCTGTCCCTGGAGAAACGCC
AGCAGCCGATGCACGTAGGTGGTCTGTTCCTGTTCCAGATCCCGGATAACGCTCCGGA
CACCTTTATTCAGGACCTGGTAACGATATCCGTATCTCCAAGTCTATTCCGGTTCCGC
CGTTCAACAACAAGCTGAACGGTCTGTTCTGGGACGAAGACGAGGAGTTCGATCTGAA
TCACCATTTCCGTCATATTGCGCTGCCGCACCCGGGTCGCATCCGTGAGCTGCTGATTT
ACATCTCTCAGGAACACAGCACTCTCCTCGATCGCGCTAAACCTCTGTGGACTTGCAAC
ATCATTGAAGGTATCGAGGGTAACCGTTTCGCCATGTACTTCAAGATTCATCATGCGAT
GGTGGATGGTGGCGGGTATGCGTCTGATTGAGAAAAGCCTGTCCCATGATGTTACT
GAAAAGAGCATCGTACCGCCGTGGTGCGTTGAGGGCAAACGTGCTAAACGCCTGCGTG
AACCGAAGACCGGCAAAATTAAGAAAATCATGTCTGGTATTAAATCTCAGCTCCAGGC
CACCCCGACCGTTATTCAAGAACTGTCTCAGACGGTCTTCAAAGACATCGGCCGTAATC
CGGACCACGTTTCCTCTTTCCAGGCGCCGTGCTCCATCCTCAACCAGCGTGTGTCTTCT
TCTCGTCGTTTCGCAGCACAGAGCTTTGACCTGGACCGTTTCCGCAACATCGCCAAATC
TCTGAACGTGACCATTAACGACGTTGTCCTGGCTGTGTGTAGCGGTGCTCTGCGCGCT
TATCTGATGTCTCATAACTCTCTGCCATCCAAACCGCTGATCGCTATGGTCCCAGCAAG
CATCCGCAACGATGATTCTGATGTGTCCAACCGTATTACTATGATTCTGGCCAACCTCG
CTACTCACAAAGACGACCCTCTGCAGCGTCTGGAAATCATCCGCCGCTCCGTCCAGAA
CTCTAAACAGCGTTTTAAACGCATGACTTCCGACCAGATTCTGAACTATTCTGCGGTTG
TATACGGCCCGGCTGGTCTGAACATTATCAGCGGTATGATGCCGAAACGTCAGGCTTT
TAACCTGGTAATCAGCAACGTTCCTGGCCCGCGTGAGCCGCTGTACTGGAACGGCGCA
AAACTGGACGCACTGTACCCGGCCTTCCATCGTTCTGGATGGCCAGGCTCTGAACATCA
CTATGACCTCTTACCTGGACAAACTGGAAGTAGGTCTGATCGCGTGTCGCAATGCACT
GCCGCGCATGCAGAACCTGCTGACCCACCTGGAGGAGGAAATCCAGCTGTTTGAGGGC
GTTATCGCCAAACAGGAAGATATCAAAACGGCGAACTAACCATGGTTGAATTCGGTTTTC
CGTCCTGTCTTGATTTTCAAGCAAACAATGCCTCCGATTTCTAATCGGAGGCATTTGTTTTG
TTTATTGCAAAAACAAAAAATATTGTTACAAATTTTTACAGGCTATTAAGCCTACCGTCATA
AATAATTTGCCATTTACTAGTTTTTAATTAACCAGAACCTTGACCGAACGCAGCGGTGGTAACG
GCGCAGTGGCGGTTTTCATGGCTTGTTATGACTGTTTTTTTGGGGTACAGTCTATGCCTCGGGCAT
CCAAGCAGCAAGCGCGTTACGCCGTGGGTCGATGTTTGATGTTATGGAGCAGCAACGATGTTACG
CAGCAGGGCAGTCGCCCTAAAACAAAGTTAAACATCATGAGGGAAGCGGTGATCGCCGAAGTATC
GACTCAACTATCAGAGGTAGTTGGCGTCATCGAGCGCCATCTCGAACCGACGTTGCTGGCCGTAC
ATTTGTACGGCTCCGCAGTGGATGGCGGCCTGAAGCCACACAGTGATATTGATTTGCTGGTTACGG
TGACCGTAAGGCTTGATGAAACAACGCGGCGAGCTTTGATCAACGACCTTTTGGAAACTTCGGCTT
CCCCTGGAGAGAGCGAGATTCTCCGCGCTGTAGAAGTCACCATTGTTGTGCACGACGACATCATTC
CGTGGCGTTATCCAGCTAAGCGCGAACTGCAATTTGGAGAATGGCAGCGCAATGACATTCTTGCAG
GTATCTTCGAGCCAGCCACGATCGACATTGATCTGGCTATCTTGCTGACAAAAGCAAGAGAACATA
GCGTTGCCTTGGTAGGTCCAGCGGCGGAGGAACTCTTTGATCCGGTTCCTGAACAGGATCTATTTG
AGGCGCTAAATGAAACCTTAACGCTATGGAACTCGCCGCCCGACTGGGCTGGCGATGAGCGAAAT
GTAGTGCTTACGTTGTCCCGCATTTGGTACAGCGCAGTAACCGGCAAAATCGCGCCGAAGGATGT
CGCTGCCGACTGGGCAATGGAGCGCCTGCCGGCCCAGTATCAGCCCGTCATACTTGAAGCTAGAC
AGGCTTATCTTGGACAAGAAGAAGATCGCTTGGCCTCGCGCGCAGATCAGTTGGAAGAATTTGTCC
ACTACGTGAAAGGCGAGATCACCAAGGTAGTCGGCAAATAATGTCTAACAATTCGTTCAAGCCGAC
GCCGCTTCGCGGCGCGGCTTAACTCAAGCGTTAGATGCACTAAGCACATAATTGCTCACAGCCAAA
CTATCAGGTCAAGTCTGCTTTTATTATTTTTAAGCGTGCATAATAAGCCCTACACAATTGGGAGATA
TATCATGAGGCGCGCCacgagtgcggggaaatttcggggcgatcgcccctatatcgcaaaaggagt
taccccatcagagctatagtcgagaagaaaaccatcattcactcaacaaggctatgtcagaagagaaa
ctagaccggatcgaagcagccctagagcaattggataaggatgtgcaaacgctccaaacagagcttca
gcaatcccaaaaatggcaggacaggacatgggatgttgtgaagtgggtaggcggaatctcagcgggcc
tagcggtgagcgcttccattgccctgttcgggttggtattagattttctgtttccagccataaaagca
cattcttataagtcatacttgtttacatcaaggaacaaaaacggcattgtgccttgcaaggcacaatg
tctttctcttatgcacagatggggactggaaaccacacgcacaattcccttaaaaagcaaccgcaaaa
aataaccatcaaaataaaactggacaaattctcatgtgGGCCGGCC
```

SEQ ID NO: 12
Ptrc promoter and lacIq repressor
```
TCACTGCCCGCTTTCCAGTCGGGAAACCTGTCGTGCCAGCTGCATTAATGAATCGGCCAACG
CGCGGGGAGAGGCGGTTTGCGTATTGGGCGCCAGGGTGGTTTTTCTTTTCACCAGTGAGACG
```

-continued

INFORMAL SEQUENCE LISTING

```
GGCAACAGCTGATTGCCCTTCACCGCCTGGCCCTGAGAGAGTTGCAGCAAGCGGTCCACGCT
GGTTTGCCCCAGCAGGCGAAAATCCTGTTTGATGGTGGTTGACGGCGGGATATAACATGAGC
TGTCTTCGGTATCGTCGTATCCCACTACCGAGATATCCGCACCAACGCGCAGCCCGGACTCG
GTAATGGCGCGCATTGCGCCCAGCGCCATCTGATCGTTGGCAACCAGCATCGCAGTGGGAAC
GATGCCCTCATTCAGCATTTGCATGGTTTGTTGAAAACCGGACATGGCACTCCAGTCGCCTTC
CCGTTCCGCTATCGGCTGAATTTGATTGCGAGTGAGATATTTATGCCAGCCAGCCAGACGCA
GACGCGCCGAGACAGAACTTAATGGGCCCGCTAACAGCGCGATTTGCTGGTGACCCAATGC
GACCAGATGCTCCACGCCCAGTCGCGTACCGTCTTCATGGGAGAAAATAATACTGTTGATGG
GTGTCTGGTCAGAGACATCAAGAAATAACGCCGGAACATTAGTGCAGGCAGCTTCCACAGC
AATGGCATCCTGGTCATCCAGCGGATAGTTAATGATCAGCCCACTGACGCGCTGCGCGAGAA
GATTGTGCACCGCCGCTTTACAGGCTTCGACGCCGCTTCGTTCTACCATCGACACCACCACG
CTGGCACCCAGTTGATCGGCGCGAGATTTAATCGCCGCGACAATTTGCGACGGCGCGTGCAG
GGCCAGACTGGAGGTGGCAACGCCAATCAGCAACGACTGTTTGCCCGCCAGTTGTTGTGCCA
CGCGGTTGGGAATGTAATTCAGCTCCGCCATCGCCGCTTCCACTTTTTCCCGCGTTTTCGCAG
AAACGTGGCTGGCCTGGTTCACCACGCGGGAAACGGTCTGATAAGAGACACCGGCATACTC
TGCGACATCGTATAACGTTACTGGTTTCATATTCACCACCCTGAATTGACTCTCTTCCGGGCG
CTATCATGCCATACCGCGAAAGGTTTTGCACCATTCGATGGTGTCAACGTAAATGCATGCCG
CTTCGCCTTCCAATTGGACTGCACGGTGCACCAATGCTTCTGGCGTCAGGCAGCCATCGGAA
GCTGTGGTATGGCTGTGCAGGTCGTAAATCACTGCATAATTCGTGTCGCTCAAGGCGCACTC
CCGTTCTGGATAATGTTTTTTGCGCCGACATCATAACGGTTCTGGCAAATATTCTGAAATGAG
CTGTTGACAATTAATCATCCGGCTCGTATAATGTGTGGAATTGTGAGCGGATAACAATTTCA
CACAGGAAACAGCAT
```

SEQ ID NO: 13

(UHR and DHR in lowercase; P$_{aphII}$ underlined; fadD and wsadp1 are in bold and underlined and follow the promoter in order; aadA marker is italicized and underlined)

```
CCTGCAGGgtcagcaagctctggaatttcccgattctctgatgggagatccaaaaattctcgcagt
ccctcaatcacgatatcggtcttggatcgccctgtagcttccgacaactgctcaattttttcgagc
atctctaccgggcatcggaatgaaattaacggtgttttagccatgtgttatacagtgtttacaact
tgactaacaaatacctgctagtgtatacatattgtattgcaatgtatacgctattttcactgctgt
ctttaatgggattatcgcaagcaagtaaaaaagcctgaaaacccaataggtaagggattccgag
cttactcgataattatcacctttgagcgccccataggaggaggcgaaaagctatgtctgacaagggg
tttgacccctgaagtcgttgcgcgagcattaaggtctgcggatagcccataacatactttgttga
acttgtgcgcttttatcaacccctttaagggcttgggagcgttttatGCGGCCGC
GGGGGGGGGGGGAAAGCCACGTTGTGTCTCAAAATCTCTGATGTTACATTGCACA
AGATAAAAATATATCATCATGAACAATAAAACTGTCTGCTTACATAAACAGTAATACAAGG
GGTCATAGATCTGTAGTAGGATCCATGTAGGGTGAGGTTATAGCTATGAAGAAAGTTTGGC
TGAACCGTTATCCGGCAGATGTACCGACTGAAATTAACCCAGATCGTTACCAGTCCCTG
GTTGACATGTTCGAACAGTCCGTGGCTCGCTACGCCGATCAGCCTGCTTTCGTCAACAT
GGGTGAGGTAATGACCTTTCGCAAACTGGAGGAGCGTTCCCGTGCTTTCGCGGCATAC
CTGCAGCAGGGTCTGGGCCTGAAGAAAGGCGACCGCGTGGCCCTGATGATGCCGAAC
CTGCTGCAATATCCTGTGGCGCTGTTCGGTATCCTGCGTGCTGGTATGATCGTTGTCAA
TGTTAACCCTCTGTATACCCCTCGTGAACTGGAGCACCAGCTGAATGACTCTGGTGCGT
CTGCTATCGTTATCGTTTCCAATTTCGCACATACGCTGGAGAAAGTGGTTGATAAAACC
GCAGTGCAGCATGTCATTCTGACTCGCATGGGTGACCAGCTGTCCACCGCTAAAGGTA
CTGTAGTCAACTTCGTTGTGAAATACATTAAGCGCCTGGTTCCGAAATACCACCTGCCA
GATGCAATTAGCTTTCGCTCTGCACTGCATAACGGTTACCGTATGCAGTACGTAAAACC
AGAGCTGGTGCCGGAAGACCTGGCCTTTCTGCAGTATACCGGCGGCACCACCGGCGTG
GCAAAGGGCGCGATGCTGACCCATCGTAACATGCTGGCGAACCTGGAGCAGGTTAACG
CAACGTACGGCCCGCTGCTGCACCCGGGTAAAGAACTGGTAGTTACGGCACTGCCTCT
GTATCACATCTTTGCACTGACGATCAACTGTCTGCTGTTCATTGAACTGGGTGGTCAGA
ACCTGCTGATCACCAACCCGCGTGACATTCCGGGCCTGGTAAAAGAGCTGGCTAAGTA
CCCGTTCACCGCCATTACTGGCGTAAACACTCTGTTTAACGCGCTGCTGAACAACAAAG
AGTTTCAGCAGCTGGACTTCTCTAGCCTGCACCTGAGCGCTGGCGGTGGCATGCCGGT
TCAGCAGGTTGTGGCAGAGCGTTGGGTGAAACTGACCGGCCAGTATCTGCTGGAGGGT
TATGGTCTGACCGAGTGTGCACCGCTGGTCAGCGTTAACCCGTATGATATTGATTACCA
CTCTGGTTCTATTGGTCTGCCGGTTCCGTCCACGGAAGCCAAACTGGTGGACGATGAC
GACAACGAAGTACCTCCGGGCCAGCCGGGTGAGCTGTGTGTCAAGGGTCCGCAGGTTA
TGCTGGGCTACTGGCAGCGCCCGGACGCCACCGACGAAATCATTAAAAACGGTTGGCT
GCATACCGGTGATATCGCTGTAATGGACGAAGAAGGTTTCCTGCGTATCGTGGACCGT
AAGAAAGATATGATTCTGGTGAGCGGTTTCAACGTGTACCCGAACGAAATTGAGGACG
TAGTTATGCAACACCCTGGCGTGCAGGAGGTGGCAGCCGTGGGCGTGCCGTCCGGTTC
TTCTGGTGAGGCTGTGAAAATCTTTGTCGTTAAAAAGGACCCGTCCCTGACCGAAGAA
TCTCTGGTGACGTTTTGCCGCCGTCAACTGACTGGCTACAAAGTGCCGAAACTGGTCG
AGTTCCGCGATGAGCTGCCAAAATCTAACGTGGGTAAGCTTCGCCGCGAGCTGCG
TGACGAGGCACGTGGCAAAGTTGACAATAAAGCATAACTCGACGCGTAGGAGGACAGCT
ATGCGCCCACTTCATCCGATCGATTTCATTTTCCTGTCCCTGGAGAAACGCCAGCAGCC
GATGCACGTAGGTGGTCTGTTCCTGTTCCAGATCCCGGATAACGCTCCGGACACCTTT
ATTCAGGACCTGGTGAACGATATCCGTATCTCCAAGTCTATTCCGGTTCCGCCGTTCAA
CAACAAGCTGAACGGTCTGTTCTGGGACGAAGACGAGGAGTTCGATCTGGATCACCAT
TTCCGTCATATTGCGCTGCCGCACACCCGGGTCGCATCCGTGAGCTGCTGATTTACATCTC
TCAGGAACACAGCACTCTCCTCGATCGCGCTAAACCTCTGTGGACTTGCAACATCATTG
AAGGTATCGAGGGTAACCGTTTCGCCATGTACTTCAAGATTCATCATGCGATGGTGGA
TGGTGTGGCGGGTATGCGTCTGATTGAGAAAAGCCTGTCCCATGATGTTACTGAAAAG
AGCATCGTACCGCCGTGGTGCGTTGAGGGCAAACGTGCTAAACGCCTGCGTGAACCGA
AGACCGGCAAAATTAAGAAAATCATGTCTGGTATTAAATCTCAGCTCCAGGCCACCCC
```

-continued

INFORMAL SEQUENCE LISTING

GACCGTTATTCAAGAACTGTCTCAGACGGTCTTCAAAGACATCGGCCGTAATCCGGAC
CACGTTTCCTCTTTCCAGGCGCCGTGCTCCATCCTCAACCAGCGTGTGTCTTCTTCTCG
TCGTTTCGCAGCACAGAGCTTTGACCTGGACCGTTTCCGCAACATCGCCAAATCTCTGA
ACGTGACCATTAACGACGTTGTCCTGGCTGTGTGTAGCGGTGCTCTGCGCGCTTATCT
GATGTCTCATAACTCTCTGCCATCCAAACCGCTGATCGCTATGGTCCCAGCAAGCATCC
GCAACGATGATTCTGATGTGTCCAACCGTATTACTATGATTCTGGCCAACCTCGCTACT
CACAAAGACGACCCTCTGCAGCGTCTGGAAATCATCCGCCGCTCCGTCCAGAACTCTA
AACAGCGTTTTAAACGCATGACTTCCGACCAGATTCTGAACTATTCTGCGGTTGTATAC
GGCCCGGCTGGTCTGAACATTATCAGCGGTATGATGCCGAAACGTCAGGCTTTTAACC
TGGTAATCAGCAACGTTCCTGGCCCGCGTGAGCCGCTGTACTGGAACGGCGCAAAACT
GGACGCACTGTACCCGGCTTCCATCGTTCTGGATGGCCAGGCTCTGAACATCACTATG
ACCTCTTACCTGGACAAACTGGAAGTAGGTCTGATCGCGTGTCGCAATGCACTGCCGC
GCATGCAGAACCTGCTGACCCACCTGGAGGAGGAAATCCAGCTGTTTGAGGGCGTTAT
CGCCAAACAGGAAGATATCAAAACGGCGAACTAACCATGGTTGAATTCGGTTTTCCGTCC
TGTCTTGATTTTCAAGCAAACAATGCCTCCGATTTCTAATCGGAGGCATTTGTTTTTGTTTATT
GCAAAAACAAAAAATATTGTTACAAATTTTTACAGGCTATTAAGCCTACCGTCATAAATAAT
TTGCCATTTACTAGTTTTTAATTAA*CCAGAACCTTGACCGAACGCAGCGGTGGTAACGGCGCAG*
*TGGCGGTTTTCATGGCTTGTTATGACTGTTTTTTTGGGGTACAGTCTATGCCTCGGGCATCCAAGCA*
*GCAAGCGCGTTACGCCGTGGGTCGATGTTTGATGTTATGGAGCAGCAACGATGTTACGCAGCAGG*
*GCAGTCGCCCTAAAACAAAGTTAAACATCATGAGGGAAGCGGTGATCGCCGAAGTATCGACTCAAC*
*TATCAGAGGTAGTTGGCGTCATCGAGCGCCATCTCGAACCGACGTTGCTGGCCGTACATTTGTACG*
*GCTCCGCAGTGGATGGCGGCCTGAAGCCACACAGTGATATTGATTTGCTGGTTACGGTGACCGTA*
*AGGCTTGATGAAACAACGCGGCGAGCTTTGATCAACGACCTTTTGGAAACTTCGGCTTCCCCTGGA*
*GAGAGCGAGATTCTCCGCGCTGTAGAAGTCACCATTGTTGTGCACGACGACATCATTCCGTGGCGT*
*TATCCAGCTAAGCGCGAACTGCAATTTGGAGAATGGCAGCGCAATGCATTCTTGCAGGTATCTTC*
*GAGCCAGCCACGATCGACATTGATCTGGCTATCTTGCTGACAAAAGCAAGAGAACATAGCGTTGCC*
*TTGGTAGGTCCAGCGGCGGAGGAACTCTTTGATCCGGTTCCTGAACAGGATCTATTTGAGGCGCTA*
*AATGAAACCTTAACGCTATGGAACTCGCCGCCCGACTGGGCTGGCGATGAGCGAAATGTAGTGCT*
*TACGTTGTCCCGCATTTGGTACAGCGCAGTAACCGGCAAAATCGCGCCGAAGGATGTCGCTGCCG*
*ACTGGGCAATGGAGCGCCTGCCGGCCCAGTATCAGCCCGTCATACTTGAAGCTAGACAGGCTTAT*
*CTTGGACAAGAAGAAGATCGCTTGGCCTCGCGCGCAGATCAGTTGGAAGAATTTGTCCACTACGTG*
*AAAGGCGAGATCACCAAGGTAGTCGGCAAATAATGTCTAACAATTCGTTCAAGCCGACGCCGCTTC*
*GCGGCGCGGCTTAACTCAAGCGTTAGATGCACTAAGCACATAATTGCTCACAGCCAAACTATCAGG*
*TCAAGTCTGCTTTTATTATTTTTAAGCGTGCATAATAAGCCCTACACAAATTGGGAGATATATCATGA*
GGCGCGCCacgagtgcggggaaatttcggggcgatcgcccctatatcgcaaaaaggagttacccat
cagagctatagtcgagaagaaaaccatcattcactcaacaaggctatgtcagaagagaaactagaccg
gatcgaagcagccctagagcaattggataaggatgtgcaaacgctccaaacagagcttcagcaatccc
aaaaatggcaggacaggacatgggatgttgtgaagtgggtaggcggaatctcagcgggcctagcggtg
agcgcttccattgccctgttcgggttggtctttagattttctgtttccctgccataaaagcacattct
ttataagtcatacttgtttacatcaaggaacaaaaacggcattgtgcctgcaaggcacaatgtattct
cttatgcacagatggggactggaaaccacacgcacaattcccttaaaaagcaaccgcaaaaaataacc
atcaaaataaaactggacaaattctcatgtgGGCCGGCC SEQ ID NO: 14
(UHR and DHR in lowercase; P<sub>aphII</sub> underlined; tesA and fadD are in
bold and underlined and follow the promoter in order; aadA marker
is italicized and underlined)
CCTGCAGGGtcagcaagactggaatttcccgattctctgatgggagatccaaaaattctcgcagtccc
tcaatcacgatatcggtatggatcgccctgtagcttccgacaactgctcaatttttttcgagcatctct
accgggcatcggaatgaaattaacggtgttttagccatgtgttatacagtgtttacaacttgactaac
aaatacctgctagtgtatacatattgtattgcaatgtatacgctattttcactgctgtctttaatggg
gattatcgcaagcaagtaaaaaagcctgaaaaccccaataggtaagggattccgagcttactcgataa
ttatcacattgagcgcccctaggaggaggcgaaaagctatgtagacaagggggtttgaccccctgaagtc
gttgcgcgagcattaaggtctgcggatagcccataacatacttttgttgaacttgtgcgcttttatca
acccccttaagggcttgggagcgttttatGCGGCCGC
GGGGGGGGGGGGGAAAGCCACGTTGTGTCTCAAAATCTCTGATGTTACATTGCACA
AGATAAAAATATATCATCATGAACAATAAAACTGTCTGCTTACATAAACAGTAATACAAGG
GGTCATATGGCGGATACTCTGCTGATTCTGGGTGATTCTCTGTCTGCAGGCTACCGTAT
GTCCGCTCCGCGGCCTGGCCAGCTCTGCTGAATGATAAGTGGCAGTCTAAGACGTCC
GTTGTGAACGCATCCATCTCTGGCGACACGAGCCAGCAGGGCCTGGCCCGTCTGCCTG
CACTGCTGAAACAGCACCAACCGCGCTGGGTCCTGGTGGAGCTGGGCGGTAACGACG
GTCTGCGCGGCTTCCAGCCGCAGCAGACCGAACAGACTCTGCGCCTGCAGATTCTGCAGGA
CGTGAAAGCTGCTAACGCGGAACCGCTGCTGATGCAGATTCGTCTGCCAGCGAACTAT
GGCCGCCGTTACAACGAAGCGTTCTCTGCAATCTACCCAAAACTGGCGAAAGAGTTTG
ACGTCCCGCTGCTGCCGTTCTTCATGGAGGAAGTATACCTGAAACCGCAGTGGATGCA
AGATGACGGCATCCACCCGAACCGTGATGCGCAGCCGTTCATCGCTGCTGACTGGATGGCG
AAGCAACTGCAGCCGCTGGTAAACCACGATTCCTAATTAAAGATCTGTAGTAGGATCCAT
GTAGGGTGAGGTTATAGCTATGAAGAAAGTTTGGCTGAACCGTTATCCGGCAGATGTAC
CGACTGAAATTAACCCAGATCGTTACCAGTCCCTGGTTGACATGTTCGAACAGTCCGTG
GCTCGCTACGCCGATCAGCCTGCTTTCGTCAACATGGGTGAGGTAATGACCTTTCGCA
AACTGGAGGAGCGTTCCCGTGCTTTCGCGGCATACCTGCAGCAGGGTCTGGGCCTGAA
GAAAGGCGACCGCGTGGCCCTGATGATGCCGAACCTGCTGCAATATCCTGTGGCGCTG
TTCGGTATCCTGCGTGCTGGTATGATCGTTGTCAATGTTAACCCTCTGTATACCCCTCG
TGAACTGGAGCACCAGCTGAATGACTCTGGTGCGTCTGCTATCGTTATCGTTTCCAATT
TCGCACATACGCTGGAGAAAGTGGTTGATAAAACCGCAGTGCAGCATGTCATTCTGAC
TCGCATGGGTGACCAGCTGTCCACCGCTAAAGGTACTGTAGTCAACTTCGTTGTGAAA
TACATTAAGCGCCTGGTTCCGAAATACCACCTGCCAGATGCAATTAGCTTTCGCTCTGC

-continued

INFORMAL SEQUENCE LISTING

ACTGCATAACGGTTACCGTATGCAGTACGTAAAACCAGAGCTGGTGCCGGAAGACCTG
GCCTTTCTGCAGTATACCGGCGGCACCACCGGCGTGGCAAAGGGCGCGATGCTGACCC
ATCGTAACATGCTGGCGAACCTGGAGCAGGTTAACGCAACGTACGGCCCGCTGCTGCA
CCCGGGTAAAGAACTGGTAGTTACGGCACTGCCTCTGTATCACATCTTTGCACTGACG
ATCAACTGTCTGCTGTTCATTGAACTGGGTGGTCAGAACCTGCTGATCACCAACCCGC
GTGACATTCCGGGCCTGGTAAAAGAGCTGGCTAAGTACCCGTTCACCGCCATTACTGG
CGTAAACACTCTGTTTAACGCGCTGCTGAACAACAAAGAGTTTCAGCAGCTGGACTTCT
CTAGCCTGCACCTGAGCGCTGGCGGTGGCATGCCGGTTCAGCAGGTTGTGGCAGAGC
GTTGGGTGAAACTGACCGGCCAGTATCTGCTGGAGGGTTATGGTCTGACCGAGTGTGC
ACCGCTGGTCAGCGTTAACCCGTATGATATTGATTACCACTCTGGTTCTATTGGTCTGC
CGGTTCCGTCCACGGAAGCCAAACTGGTGGACGATGACGACAACGAAGTACCTCCGGG
CCAGCCGGGTGAGCTGTGTGTCAAGGGTCCGCAGGTTATGCTGGGCTACTGGCAGCGC
CCGGACGCCACCGACGAAATCATTAAAAACGGTTGGCTGCATACCGGTGATATCGCTG
TAATGGACGAAGAAGGTTTCCTGCGTATCGTGGACCGTAAGAAAGATATGATTCTGGT
GAGCGGTTTCAACGTGTACCCGAACGAAATTGAGGACGTAGTTATGCAACACCCTGGC
GTGCAGGAGGTGGCAGCCGTGGGCGTGCCGTCCGGTTCTTCTGGTGAGGCTGTGAAA
ATCTTTGTCGTTAAAAAGGACCCGTCCTGACCGAAGAATCTCTGGTGACGTTTTGCCG
CCGTCAACTGACTGGCTACAAAGTGCCGAAACTGGTCGAGTTCCGCGATGAGCTGCCA
AAATCTAACGTGGGTAAGATCCTGCGCCGCGAGCTGCGTGACGAGGCACGTGGCAAAG
TTGACAATAAAGCATAACAATTCGGTTTTCCGTCCTGTCTTGATTTTCAAGCAAACAATGCC
TCCGATTTCTAATCGGAGGCATTTGTTTTTGTTTATTGCAAAAACAAAAAATATTGTTACAAA
TTTTTACAGGCTATTAAGCCTACCGTCATAAATAATTTGCCATTTACTAGTTTTTAATTAA*CC
AGAACCTTGACCGAACGCAGCGGTGGTAACGGCGCAGTGGCGGTTTTCATGGCTTGTTATGACTG
TTTTTTTGGGGTACAGTCTATGCCTCGGGCATCCAAGCAGCAGCGCGTTACGCCGTGGGTCGAT
GTTTGATGTTATGGAGCAGCAACGATGTTACGCAGCAGGGCAGTCGCCCTAAAACAAAGTTAAACA
TCATGAGGGAAGCGGTGATCGCCGAAGTATCGACTCAACTATCAGAGGTAGTTGGCGTCATCGAG
CGCCATCTCGAACCGACGTTGCTGGCCGTACATTTGTACGGCTCCGCAGTGGATGGCGGCCTGAA
GCCACACAGTGATATTGATTTGCTGGTTACGGTGACCGTAAGGCTTGATGAAACAACGCGGCGAGC
TTTGATCAACGACCTTTTGGAAACTTCGGCTTCCCCTGGAGAGAGCGAGATTCTCCGCGCTGTAGA
AGTCACCATTGTTGTGCACGACGACATCATTCCGTGGCGTTATCCAGCTAAGCGCGAACTGCAATT
TGGAGAATGGCAGCGCAATGACATTCTTGCAGGTATCTTCGAGCCAGCCACGATCGACATTGATCT
GGCTATCTTGCTGACAAAAGCAAGAGAACATAGCGTTGCCTTGCAGCCTGCAGCGGCGGAGGAAC
TCTTTGATCCGGTTCCTGAACAGGATCTATTTGAGGCGCTAAATGAAACCTTAACGCTATGGAACTC
GCCGCCCGACTGGGCTGGCGATGAGCGAAATGTAGTGCTTACGTTGTCCCGCATTTGGTACAGCG
CAGTAACCGGCAAAATCGCGCCGAAGGATGTCGCTGCCGACTGGGCAATGGAGCGCCTGCCGGC
CCAGTATCAGCCCGTCATACTTGAAGCTAGACAGGCTTATCTTGGACAAGAAGAAGATCGCTTGGC
CTCGCGCGCAGATCAGTTGGAAGAATTTGTCCACTACGTGAAAGGCGAGATCACCAAGGTAGTCG
GCAAATAATGTCTAACAATTCGTTCAAGCCGACGCCGCTTCGCGGCGCGGCTTAACTCAAGCGTTA
GATGCACTAAGCACATAATTGCTCACAGCCAAACTATCAGGTCAAGTCTGCTTTTATTATTTTTAAGC
GTGCATAATAAGCCCTACACAAATTGGGAGATATATCATG*AGGCGCGCCacgagtgcggggaaatttc
ggggggcgatcgccctatatcgcaaaaaggagttaccccatcagagctatagtcgagaagaaaaccat
cattcactcaacaaggctatgtcagaagagaaactagaccggatcgaagcagccctagagcaattgga
taaggatgtgcaaacgctccaaacagagcttcagcaatcccaaaaatggcaggacaggacatgggatg
ttgtgaagtgggtaggcggaatctcagcgggcctagcggtgagcgcttccattgccagttcgggttgg
tctttagattttctgtttccctgccataaaagcacattcttataagtcatacttgtttacatcaagga
acaaaaacggcattgtgccttgcaaggcacaatgtctttctcttatgcacagatggggactggaaacc
acacgcacaattcccttaaaaagcaaccgcaaaaaataaccatcaaaataaaactggacaaattctca
tgtgGGCCGGCC SEQ ID NO: 15
pJB161
(vector contains bla cassette, pUC ori and transcription terminators
flanking the homology regions; UHR and DHR are lowercase; P$_{aphII}$
promoter is underlined; adhII terminator is in bold; kan$^R$ marker is
italicized and underlined)
ACCAATGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCCAGCGT
GCGATGATACCGCGAGAACCACGCTCACCGGCTCCGGATTTATCAGCAATAAACCAGCCAG
CCGGAAGGGCCGAGCGCAGAAGTGGTCCTGCAACTTTATCCGCCTCCATCCAGTCTATTAAT
TGTTGCCGGGAAGCTAGAGTAAGTAGTTCGCCAGTTAATAGTTTGCGCAACGTTGTTGCCAT
CGCTACAGGCATCGTGGTGTCACGCTCGTCGTTTGGTATGGCTTCATTCAGCTCCGGTTCCCA
ACGATCAAGGCGAGTTACATGATCCCCCATGTTGTGCAAAAAAGCGGTTAGCTCCTTCGGTC
CTCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAACC
AAGTCATTCTGAGAATAGTGTATGCGGCGACCGAGTTGCTCTTGCCCGGCGTCAATACGGGA
TAATACCGCGCCACATAGCAGAACTTTAAAAGTGCTCATCATTGGAAAACGTTCTTCGGGGC
GAAAACTCTCAAGGATCTTACCGCTGTTGAGATCCAGTTCGATGTAACCCACTCGTGCACCC
AACTGATCTTCAGCATCTTTTACTTTCACCAGCGTTTCTGGGTGAGCAAAAACAGGAAGGCA
AAATGCCGCAAAAAAGGGAATAAGGGCGACACGGAAATGTTGAATACTCATATTCTTCCTTT
TTCAATATTATTGAAGCATTTATCAGGGTTATTGTCTCATGAGCGGATACATATTTGAATGTA
TTTAGAAAAATAAACAAATAGGGGTCAGTGTTACAACCAATTAACCAATTCTGAACATTATC
GCGAGCCCATTTATACCTGAATATGGCTCATAACACCCCTTGTTTGCCTGGCGGCAGTAGCG
CGGTGGTCCCACCTGACCCCATGCCGAACTCAGAAGTGAAACGCCGTAGCGCCGATGGTAG
TGTGGGGACTCCCCATGCGAGAGTAGGGAACTGCCAGGCATCAAATAAAACGAAAGGCTCA
GTCGAAAGACTGGGCCTTTCGCCCGGGCTAATTATGGGGTGTCGCCCTTATTCGACTCTATA
GTGAAGTTCCTATTCTCTAGAAAGTATAGGAACTTCTGAAGTGGGGCCTGCAGGgccaccacagcc
aaattcatcgttaatgtggacttgccgacgccccttttcgactaacaatcgcaatttttttcata -continued

INFORMAL SEQUENCE LISTING

```
gacatttcccacagaccacatcaaattacagcaattgatctagctgaaagtttaacccacttcccc
ccagacccagaagaccagaggcgcttaagcttccccgaacaaactcaactgaccgaggggggaggga
gccgtagcggcgttggtgttggcgtaaatgacaggccgagcaaagagcgatgagattttcccgacg
attgtcttcggggatgtaattttttgtggtggacgcttaaggttaaaacagcccgcaggtgacgatc
aatgcctttgaccttcacatccgacggaatacaaaccaagccacagagttcacagcgccagtctgc
atcctcttttacttgtaaggcgatcgcctgccaatcatcagaatatcgagaagaatgtttcatcta
aacctagcgccgcaagataatcctgaaatcgctacagtattaaaaaattctggccaacatcacagc
caatactGCGGCCGCGGGGGGGGGGGGGGAAAGCCACGTTGTGTCTCAAAATC
TCTGATGTTACATTGCACAAGATAAAAATATATCATCATGAACAATAAAACTGTCTGCTTAC
ATAAACAGTAATACAAGGGGTCATATGTAACAGGAATTCGGTTTTCCGTCCTGTCTTGATT
TTCAAGCAAACAATGCCTCCGATTTCTAATCGGAGGCATTTGTTTTTTGTTTATTGCAAA
AACAAAAAATATTGTTACAAATTTTTACAGGCTATTAAGCCTACCGTCATAAATAATTT
GCCATTTACTAGTTTTTAATTAAACCCCTATTTGTTTATTTTCTAAATACATTCAAATATGTATCC
GCTCATGAGACAATAACCCTGATAAATGCTTCAATAATATTGAAAAAGGAAGAGTATGATTGAACAA
GATGGCCTGCATGCTGGTTCTCCGGCTGCTTGGGTGGAACGCCTGTTTGGTTACGACTGGGCTCA
GCTGACTATTGGCTGTAGCGATGCAGCGGTTTTCCGTCTGTCTGCACAGGGTCGTCCGGTTCTGTT
TGTGAAAACCGACCTGTCCGGCGCACTGAACGAACTGCAGGACGAAGCGGCCCGTCTGTCCTGG
CTCGCGACGACTGGTGTTCCGTGCGCGGCAGTTCTGGACGTAGTTACTGAAGCCGGTCGCGATTG
GCTGCTGCTGGGTGAAGTTCCGGGTCAGGATCTGCTGAGCAGCCACCTCGCTCCGGCAGAAAAG
TTTCCATCATGGCGGACGCGATGCGCGTCTGCACACCCTGGACCCGGCAACTTGCCCGTTTGAC
CATCAGGCTAAACACCGTATTGAACGTGCACGCACTCGTATGGAAGCGGGTCTGGTTGATCAGGA
CGACCTGGATGAAGAGCACCAGGGCCTCGCACCGGCGGAACTGTTTGCACGTCTGAAAGCCCGC
ATGCCGGACGGCGAAGACCTGGTGGTAACGCATGGCGACGCTTGTCTGCCAAACATTATGGTGGA
AAACGGCCGCTTCTCTGGTTTTATTGACTGTGGCCGTCTGGGTGTAGCTGATCGCTATCAGGATAT
CGCCCTCGCTACCCGCGATATTGCAGAAGAACTGGGTGGTGAATGGGCTGACCGTTTCCTGGTGC
TGTACGGTATCGCAGCGCCGGATTCTCAGCGCATTGCCTTCTACCGTCTGCTGGATGAGTTCTTCT
AAGGCGCGCCgaaactgcgccaagaatagctcacttcaaatcagtcacggttttgtttagggcttgt
ctggcgattttggtgacatagacagtcacagcaacagtagccacaaaaccaagaatccggatcgacc
actgggcaatgggggttggcgctggtgctttctgtgccgagggtcgcaagatttccggccagggagcc
aatgtagacatacatgatggtgccagggatcatccccacagagccgaggacatagtcttttagggaa
acgcccgtgaccccataggcatagttaagcagattaaagggaaatacaggtgagagacgcgtcagga
gaacaatcttcaggccttccttgcccacagcttcgtcgatggcgcgaaatttcgggttgtcggcgat
ttttggctcacccattggcgggccagataacgacccactaggaaagcagcgatcgctcctagggtt
gcgccaacaaagacgtaaattgatcctaaagcgacaccaaaaacaacccggctcccaaggtcagaa
tcgaccccggtagaaaagccaccgtcgccaccacataaagcaccataaaggcgat
GGCCGGCCAAAATGAAGTGAAGTTCCTATACTTTCTAGAGAATAGGAACTTCTATAGTGAG
TCGAATAAGGGCGACACAAAATTTATTCTAAATGCATAATAAATACTGATAACATCTTATAG
TTTGTATTATATTTTGTATTATCGTTGACATGTATAATTTTGATATCAAAAACTGATTTTCCCT
TTATTATTTTCGAGATTTATTTTCTTAATTCTCTTTAACAAACTAGAAATATTGTATATACAAA
AAATCATAAATAATAGATGAATAGTTTAATTATAGGTGTTCATCAATCGAAAAAGCAACGTA
TCTTATTTAAAGTGCGTTGCTTTTTTCTCATTTATAAGGTTAAATAATTCTCATATATCAAGCA
AAGTGACAGGCGCCCTTAAATATTCTGACAAATGCTCTTTCCCTAAACTCCCCCCATAAAAA
AACCCGCCGAAGCGGGTTTTTACGTTATTTGCGGATTAACGATTACTCGTTATCAGAACCGC
CCAGGGGGCCCGAGCTTAAGACTGGCCGTCGTTTTACAACACAGAAAGAGTTTGTAGAAAC
GCAAAAAGGCCATCCGTCAGGGGCCTTCTGCTTAGTTTGATGCCTGGCAGTTCCCTACTCTC
GCCTTCCGCTTCCTCGCTCACTGACTCGCTGCGCTCGGTCGTTCGGCTGCGGCGAGCGGTATC
AGCTCACTCAAAGGCGGTAATACGGTTATCCACAGAATCAGGGGATAACGCAGGAAAGAAC
ATGTGAGCAAAAGGCCAGCAAAAGGCCAGGAACCGTAAAAAGGCCGCGTTGCTGGCGTTTT
TCCATAGGCTCCGCCCCCCTGACGAGCATCACAAAAATCGACGCTCAAGTCAGAGGTGGCG
AAACCCGACAGGACTATAAAGATACCAGGCGTTTCCCCCTGGAAGCTCCCTCGTGCGCTCTC
CTGTTCCGACCCTGCCGCTTACCGGATACCTGTCCGCCTTTCTCCCTTCGGGAAGCGTGGCGC
TTTCTCATAGCTCACGCTGTAGGTATCTCAGTTCGGTGTAGGTCGTTCGCTCCAAGCTGGGCT
GTGTGCACGAACCCCCCGTTCAGCCCGACCGCTGCGCCTTATCCGGTAACTATCGTCTTGAG
TCCAACCCGGTAAGACACGACTTATCGCCACTGGCAGCAGCCACTGGTAACAGGATTAGCA
GAGCGAGGTATGTAGGCGGTGCTACAGAGTTCTTGAAGTGGTGGCTAACTACGGCTACACT
AGAAGAACAGTATTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTGTTTGCAAGCAGC
AGATTACGCGCAGAAAAAAAGGATCTCAAGAAGATCCTTTGATCTTTTCTACGGGGTCTGAC
GCTCAGTGGAACGACGCGCGTAACTCACGTTAAGGGATTTTGGTCATGAGCTTGCGCCGT
CCCGTCAAGTCAGCGTAATGCTCTGCTTTT
```

SEQ ID NO: 16
$P_{psaA}$-tolC-$P_{tsr2142}$-acrAB insert with flanking homology regions
This sequence inserted into pJB161 to create PJB1074
(UHR and DHR in lowercase and not underlined; $P_{psaA}$ and $P_{tsr2142}$ are
underlined and capitalized; tolC, acrA and acrB are in bold,
lowercase, and underlined and follow the promoter in order; kan$^R$
marker is italicized and underlined)

```
CCTGCAGGgccaccacagccaaattcatcgttaatgtggacttgccgacgccccttttcgacta
acaatcgcaattttttcatagacatttcccacagaccacatcaaattacagcaattgatctaga
gaaagtttaacccacttcccccagacccagaagaccagaggcgataagcttccccgaacaaact
caactgaccgagggggaggagccgtagcggcgttggtgttggcgtaaatgacaggccgagcaaa
gagcgatgagattttcccgacgattgtcttcggggatgtaattttttgtggtggacgcttaaggtt
aaaacagcccgcaggtgacgatcaatgcctttgaccttcacatccgacggaatacaaaccaagcc
acagagttcacagcgccagtctgcatcctcttttacttgtaaggcgatcgcctgccaatcatcag
aatatcgagaagaatgtttcatctaaacctagcgccgcaagataatcctgaaatcgctacagtat
taaaaaattctggccaacatcacagccaatactGCGGCCGCGCCCCTATATTATGCATTTATA
```

INFORMAL SEQUENCE LISTING

CCCCCACAATCATGTCAAGAATTCAAGCATCTTAAATAATGTTAATTATCGGCAAAGTCTGT
GCTCCCCTTCTATAATGCTGAATTGAGCATTCGCCTCCTGAACGGTCTTTATTCTTCCATTGT
GGGTCTTTAGATTCACGATTCTTCACAATCATTGATCTAAAGATCTTTCTAGATTCTCGAGGC
ATatgaagaaattgctccccattcttatcggcctgagcctttctgggttcagttcgttgagccag
gccgagaacctgatgcaagtttatcagcaagcacgccttagtaacccggaattgcgtaagtctgcc
gccgatcgtgatgctgcctttgaaaaaattaatgaagcgcgcagtccattactgccacagctaggt
ttaggtgcagattacacctatagcaacggctaccgcgacgcgaacggcatcaactctaacgcgacc
agtgcgtccttgcagttaactcaatccattttgatatgtcgaaatggcgtgcgttaacgctgcag
gaaaaagcagcaggattcaggacgtcacgtatcagaccgatcagcaaaccttgatcctcaacacc
gcgaccgcttatttcaacgtgttgaatgctattgacgttctttcctatacacaggcacaaaaagaa
gcgatctaccgtcaattagatcaaaccaccaacgttttaacgtgggcctggtagcgatcaccgac
gtgcagaacgcccgcgcacagtacgataccgtgctggcgaacgaagtgaccgcacgtaataaccctt
gataacgcggtagagcagctgcgccagatcaccggtaactactatccggaactggctgcgctgaat
gtcgaaaactttaaaaccgacaaaccacagccggttaacgcgctgctgaaagaagccgaaaaacgc
aacctgtcgctgttacaggcacgcttgagccaggacctggcgcgcgagcaaattcgccaggcgcag
gatggtcacttaccgactctgatttaacggcttctaccgggattctgacacctcttatagcggt
tcgaaaccccgtggtgccgctggtacccagtatgacgatagcaatatgggccagaacaaagttggc
ctgagcttctcgctgccgatttatcagggcggaatggttaactcgcaggtgaaacaggcacagtac
taactttgtcggtgccagcgagcaactggaaagtgcccatcgtagcgcgtgcagaccgtgcgttcc
tccttcaacaacattaatgcatctatcagtagcatttaacgcctacaaacaagccgtagtttccgt
caaagctcattagacgcgatggaagcgggctactcggtcggtacgcgtaccattgttgatgtgttg
gatgcgaccaccacgttgtacaacgccaagcaagagctggcgaatgcgcgttataacctgatt
aatcagctgaatattaagtcagctctgggtacgttgaacgagcaggatctgctggcactgaacaat
gcgctgagcaaaccggtttccaataatccggaaaacgttgcacgcaaaccgggaacagaatgct
attgctgatggttatgcgcctgatagcccggcaccagtcgttcagcaaacatccgcacgcactacc
accagtaacggtcataaccattccgtaactgaGGATCCAAGGTGGCTACTTCAACGATAGCTTAAA
CTTCGCTGCTCCAGCGAGGGGATTTCACTGGTTTGAATGCTTCAATGCTTGCCAAAAGAGTGCTAC
TGGAACTTACAAGAGTGACCCTGCGTCAGGGGAGCTAGCACTCAAAAAAGACTCCTCCAATTCCGTCC
atgaacaaaaacagaggggtttacgcctctggcggtcgttctgatgctctcaggcagcttagccctaac
aggatgtgacgacaaacaggcccaacaaggtggccagcagatgcccgccgttggcgtagtaacagtca
aaactgaacctctgcagatcacaaccgagcttccgggtcgcaccagtgcctaccggatcgcagaagtt
cgtcctcaagttagcgggattatcctgaagcgtaatttcaaagaaggtagcgacatcgaagcaggtgt
ctctctctatcagattgatcctgcgacctatcaggcgacatacgacagtcgcgaaaggtgatctggcga
aagcccaggctgcagccaatatcgcgcaattgacggtgaatcgttatcagaaactgctcggtactcag
tacatcagtaagcaagagtacgatcaggctctggctgatgcgcaacaggcgaatggtgcggtaactgc
ggcgaactgccgttgaaactgcgcggatcaatctggcttacaccaaagtcacctctccgattagcgg
tcgcattggtaagtcgaacgtgacggaaggcgcattggtacagaacggtcaggcgactgcgctggcaa
ccgtgcagcaacttgatccgatctacgttgatgtgacccagtccagcaacgacttcctgcgcctgaaa
caggaactggcgaatggcacgctgaaacaagagaacggcaaagccaaagtgtcactgatcaccagtga
cggcattaagttcccgcaggacggtacgctggaattctctgacgttaccgttgatcagaccactgggt
ctatcaccctacgcgctatcttcccgaacccggatcacactctgctgccgggtatgttcgtgcgcgca
cgtctggaagaagggcttaatccaaacgctattttagtcccgcaacagggcgtaacccgtacgccgcg
tggcgatgccaccgtactggtagttggcgcggatgacaaagtggaaacccgtccgatcgttgcaagcc
aggctattggcgataagtggctggtgacagaaggtctgaaagcaggcgatcgcgtagtaataagtggg
ctgcagaaagtgcgtcctggtgtccaggtaaaagcaagagttaccgctgataataaccagcaagc
cgcaagcggtgctcagcctgaacagtccaagtcttaacttaaacaggagccgttaagacatgcctaat
ttctttatcgatcgcccgattttttgcgtgggtgatcgccattatcatcatgttggcaggggggctggc
gatcctcaaactgccggtggcgcaatatcctacgattgcaccgccggcagtaacgatctccgcctcct
acccccggcgctgatgcgaaaacagtgcaggacacggtgacacaggttatcgaacagaatatgaacggt
atcgataacctgatgtacatgtcctctaacagtgactccacgggtaccgtgcagatcaccctgaccctt
tgagtctggtactgatgcggatatcgcgcaggttcaggtgcagaacaaactgcagctggcgatgccgt
tgctgccgcaagaagttcagcagcaaggggtgagcgttgagaaatcatccagcagcttcctgatggtt
gtcggcgttatcaacaccgatggcaccatgacgcaggaggatatctccgactacgtggcggcgaatat
agaaagatgccatcagccgtacgtcgggcgtgggtgatgttcgttgtcggttcacagtacgcgatgc
gtatctggatgaacccgaatgagctgaacaaattccagctaacgccggttgatgtcattaccgccatc
aaagcgcagaacgcccaggttgcggcgggtcagctcggtggtacgccgcggtgaaaggccaacagct
taacgcctctattattgctcagacgcgtctgacctctactgaagagttcggcaaaatcctgctgaaag
tgaatcaggatggttcccgcgtgctgctgcgtgacgtcgcgaagattgagctgggtggtgagaactac
gacatcatcgcagagtttaacggccaaccggcttccggtctggggatcaagtggcgaccggtgcaaa
cgcgctggataccgctgcggcaatccgtgctgaactggcgaagatggaaccgttcttcccgtcgggtc
tgaaaattgtttacccatacgacaccacgccgttcgtgaaaatctctattcacgaagtggttaaaacg
ctggtcgaagcgatcatcctcgtgttcctggttatgtatctgttcctgcagaacttccgcgacgacgtt
gattccgaccattgccgtaccggtggtattgctcgggacctttgccgtcctttgccgcctttggcttct
cgataaacacgtaacaatgttcgggatggtgctcgccatggcctattggtggatgacgccatcgtt
gtggtagaaaacgttgagcgtgttatggcggaagaaggtttgccgccaaaagaagctacccataaatc
gatggggcagattcaggggcgctctggtcggtatcgcgatggtactgtcggcggtattcgtaccgatgg
ccttcttggcggttctactggtgctatctatcgtcagttctctattaccattgtttcagcaatgatgg
ctgtcggtactggtggcgttgatcctgactccagctctttgtgccaccatgctgaaaccgattgccaa
aggcgatcacggggaaggtaaaaaaggcttcttcggctgcgtttaaccgcatgttcgagaagagcacgc
accactacaccgacagcgtaggcggtattctgcgcagtacggggcgttacctggtgctgtatctgatc
atcgtggtcggcatggcctatctgttcgtgcgtctgccaagctccttcttgccagatgaggaccaggg
cgtgttttatgaccatggttcagctgccacaggtgcaacgcaggaaacaggaaagaagtgctcaatg
aggtaacgcattactatctgaccaaagaaaagaacaacgttgagtcggtgttcgccgttaacggcttc
ggctttgcgggacgtggtcagaataccggtattgcgttcgtttccttgaaggactgggccgatcgtcc
gggcgaagaaaacaaagttgaagcgattaccatgcgtgcaacacgcgctttctcgcaaatcaaagatg
cgatggttttcgcctttaacctgcccgcaatcgtggaactgggtactgcaacggctttgactttgag
ctgattgaccaggctggccttggtcacgaaaaaactgactcaggcgcgtaaccagttgcttgcagaagc -continued

INFORMAL SEQUENCE LISTING agcgaagcaccctgatatgttgaccagcgtacgtccaaacggtctggaagataccccgcagtttaaga
ttgatatcgaccaggaaaaagcgcaggcgctgggtgtttctatcaacgacattaacaccactctgggc
gctgcatggggcggcagctatgtgaacgactttatcgaccgcggtcgtgtgaagaaagtttatgtcat
gtcagaagcgaaataccgtatgctgccggatgatatcggcgactggtatgttcgtgctgctgatggtc
agatggtgccattctcggcgttctcctcttctcgttgggagtacggttcgccgcgtctggaacgttac
aacggcctgccatccatggaaatcttaggccaggcggcaccgggtaaaagtaccggtgaagcaatgga
gctgatggaacaactggcgagcaaactgcctaccggtgttggctatgactggacggggatgtcctatc
aggaacgtctctccggcaaccaggcaccttcactgtacgcgatttcgttgattgtcgtgttcctgtgt
ctggcggcgctgtacgagagctggtcgattccgttctccgttatgctggtcgttccgctgggggttat
cggtgcgttgctggctgccaccttccgtggcctgaccaatgacgtttacttccaggtaggcctgctca
caaccttgggttgtcggcgaagaacgcgatccttatcgtcgaattcgccaaagacttgatggataaag
aaggtaaaggtctgattgaagcgacgcttgatgcggtgcggatgcgtttacgtccgatcctgatgacc
tcgctggcgtttatcctcggcgttatgccgctggttatcagtactggtgctggttccggcgcgcagaa
cgcagtaggtaccggtgtaatgggcgggatggtgaccgcaacggtactggcaatcttcttcgttccgg
tattctttgtggtggttcgccgccgctttagccgcaagaatgaagatatcgagcacagccatactgtc
gatcatcattgaGAGCTCttGAATTCGGTTTTCCGTCCTGTCTTGATTTTCAAGCAAACAATGCCTCC
GATTTCTAATCGGAGGCATTTGTTTTTGTTTATTGCAAAAACAAAAAATATTGTTACAAATTTTTACA
GGCTATTAAGCCTACCGTCATAAATAATTTGCCATTTACTAGTTTTTAATTAAACCCCTATTTGTTTA
TTTTTCTAAATACATTCAAATATGTATCCGCTCATGAGACAATAACCCTGATAAATGCTTCAATAATA
TTGAAAAAGGAAGAGTATGATTGAACAAGATGGCCTGCATGCCTGTTCTCCGGCTGCTTGGGTGGAAC
GCCTGTTTGGTTACGACTGGGCTCAGCTGACTATTGGCTGTAGCGATGCAGCGGTTTTCCGTCTGTCT
GCACAGGGTCGTCCGGTTCTGTTTGTGAAAACCGACCTGTCCGGCGCACTGAACGAACTGCAGGACGA
AGCGGCCCGTCTGTCCTGGCTCGCGACGACTGGTGTTCCGTGCGCGGCAGTTCTGGACGTAGTTACTG
AAGCCGGTCGCGATTGGCTGCTGCTGGGTGAAGTTCCGGGTCAGGATCTGCTGAGCAGCCACCTCGCT
CCGGCAGAAAAAGTTTCCATCATGGCGGACGCGATGCGCCGTCTGCACACCCTGGACCCGGCAACTTG
CCCGTTTGACCATCAGGCTAAACACCGTATTGAACGTGCACGCACTCGTATGGAAGCGGGTCTGGTTG
ATCAGGACGACCTGGATGAAGAGCACCAGGGCCTCGCACCGGCGGAACTGTTTGCACGTCTGAAAGCC
CGCATGCCGGACGGCGAAGACCTGGTGGTAACGCATGCGCGCTTGTCTGCCAAACATTATGGTGGA
AAACGGCCGCTTCTCTGGTTTTATTGACTGTGGCCGTCTGGGTGTAGCTGATCGCTATCAGGATATCG
CCCTCGCTACCCGCGATATTGCAGAAGAACTGGGTGGTAATGGGCTGACCGTTTCCTGGTGCTGT
ACGGTATCGCAGCGCCGGATTCTCAGCGCATTGCCTTCTACCGTCTGCTGGATGAGTTCTTCTAAG
GCGCGCCgaaactgcgccaagaatagctcacttcaaatcagtcacggttttgtttagggcttgtctgg
cgattttggtgacatagacagtcacagcaacagtagccacaaaaccaagaatccggatcgaccactgg
gcaatgggggttggcgctggtgcttctctgtgccgagggtcgcaagatttccggccagggagccaatgta
gacatacatgatggtgccagggatcatccccacagagccgaggacatagtatttagggaaacgcccgt
gaccccataggcatagttaagcagattaaagggaaatacaggtgagagacgcgtcaggagaacaatct
tcaggccttccttgcccacagcttcgtcgatggcgcgaaattcgggttgtcggcgattttttggctc
acccattggcgggccagataacgacccactaggaaagcagcgatcgctcctagggttgcgccaacaaa
gacgtaaattgatcctaaagcgacaccaaaaacaaccccggctcccaaggtcagaatcgaccccggtaG
gaaaagccaccgtcgccaccacataaagcaccataaaggcgatGCCGGCC SEQ ID NO: 17
P(nirA): *S. elongatus* PCC 7942
TCCCTCTCAGCTCAAAAAGTATCAATGATTACTTAATGTTTGTTCTGCGCAAACTTCT
TGCAGAACATGCATGATTTACAAAAAGTTGTAGTTTCTGTTACCAATTGCGAATCGA
GAACTGCCTAATCTGCCGAGTATGCAAGCTGCTTTGTAGGCAGATGAATCCCAT SEQ ID NO: 18
P(nir07): *S. elongatus* PCC 7942 + *Synechococcus* sp. PCC 7002 rbcL
altered ribosome binding site (RBS)
GCTTGTAGCAATTGCTACTAAAAACTGCGATCGCTGCTGAAATGAGCTGGAATTTTG
TCCCTCTCAGCTCAAAAAGTATCAATGATTACTTAATGTTTGTTCTGCGCAAACTTCT
TGCAGAACATGCATGATTTACAAAAAGTTGTAGTTTCTGTTACCAATTGCGAATCGA
GAACTGCCTAATCTGCCGAGTATGCGATCCTTTAGCAGGAGGAAAACCAT SEQ ID NO: 19
P(nir09): *Anabaena* sp. PCC 7120 + *Synechococcus* sp. PCC 7002 rbcL RBS
GCTACTCATTAGTTAAGTGTAATGCAGAAAACGCATATTCTCTATTAAACTTACGCA
TTAATACGAGAATTTTGTAGCTACTTATACTATTTTACCTGAGATCCCGACATAACCT
TAGAAGTATCGAAATCGTTACATAAACATTCACACAAACCACTTGACAAATTTAGCC
AATGTAAAAGACTACAGTTTCTCCCCGGTTTAGTTCTAGAGTTACCTTCAGTGAAAC
ATCGGCGGCGTGTCAGTCATTGAAGTAGCATAAATCAATTCAAAATACCCTGCGGG
AAGGCTGCGCCAACAAAATTAAATATTTGGTTTTTCACTATTAGAGCATCGATTCAT
TAATCAAAAACCTTACCCCCCAGCCCCCTTCCCTTGTAGGGAAGTGGGAGCCAAACT
CCCCTCTCCGCGTCGGAGCGAAAAGTCTGAGCGGAGGTTTCCTCCGAACAGAACTTT
TAAAGAGAGAGGGGTTGGGGGAGAGGTTCTTTCAAGATTACTAAATTGCTATCACT
AGACCTCGTAGAACTAGCAAAGACTACGGGTGGATTGATCTTGAGCAAAAAAACTT
TATGAGAACTTTAGCAGGAGGAAAACCAT SEQ ID NO: 20
nrsS-nrsR-P(nrsB): *Synechocystis* sp. PCC 6803 sll0798-sll0797
Pslr0793 + *Synechococcus* sp. PCC 7002 rbcL RBS
GATTACCCTATATCGGGCTTTTCTCAATAAAATCTTTATTTTTTGAGGTGCTTTTTAG
CCATAAATAATCACTTTAGTATAAATTTTGACGGCGTAAAGTTGATAAAATAGAAT
TAAGAATGGACTATCGGTACAGAAAAAATGGGTAACTGGATGGTGAATAAACTTCC
CTTACCCAATGCACTCTCCACCGTTAAAGACCCCCTATGCTTAACGGTGATCACCTG
GGCAATGGCGAGTCCCAACCCTGTCCCCCCCGTTTTGCGCGAACGATCTCGATTAAC

INFORMAL SEQUENCE LISTING

```
TCGGTAAAAACGCTCAAAAATGTGTTCCTGTTGGTCGGGGGCAATGCCGATGCCGGT
ATCTTGCACGGTGATGATAGCCATCTGTTCATGGGATGTCAGGGTAATATCAACACG
TCCCCCAGCAGTTGTGTATTGAATGGCGTTGGCAATTAGGTTTGAGACCAGTCGATA
GAGTTGGGATTCATTACCCCAGGCGTAAACTTCCCCTGAACTCAGATCACTGCTGAG
ATCAATGTGGGCGGCGATCGCTAATTCTAAAAACTCTTCGGTGAGGTCACTGACTAA
ATCATTTAAACAACAAAGCCGCCAATCTTCGGCGGTGGTTTCCTGCTCTAAGCGACT
TAGTAGCAATAAATCCGTAATCAATTGGCTTAATCGCCTTCCCTGTCGTTCAACGGT
ATGTAGCATGGTGTTAATTTCTGGGGAATGGCTTGAGTCGATGCGTAATACCGCTTC
CACCGTGGCCAACAGACTAGCCAATGGCGATCGTAATTCATGGGCTGCATTCGCGGT
GAATTGTTGTTGTTGGTAGGACTGGTAAATGGGACGCATGGCTAACCCCGCTAA
GCCCCAACTGGAGAAGGCGACCAAACCCAGGGCAATGGGAAAACTAAGCCCTAAA
ATCCAAAGAATACGTTTATTTTCGGCATCAAAGGCTGCCAGGCTCCGGCCAATTTGT
AGATAGCCCCAGGAAGATTTGTCTGTATTACCGGCGCTATGCAAATGGTGGTGAAT
TGTCGATACCGATCGCCGGTTGGGGGGTGAATAGTCTGCCAAGTTTCCTGGTTAAAA
ATGGAGGATAGGGAAGCCGGTTGATTAGGCGAAAAAGCCAGCAGGTTGCCTTGATA
ATCAAATAAACGAATGTAATATAAACTGCGATCACTAATGCCCAACGTGTGACGTTC
AATCAGGGTGGGGTTGACCTGGCAGGGTTGGTTGACCAAACACAGATCGGGCAACA
TTTTTTGTAATACTCCGGTGGGACTAGCATTACTCGGCAACATCGGCTCTAAACTGTC
ATGCAACGTCCCGGCGATCGACTCCACTTCTCGCTCCAACGCCATCCAGTTGGCCTG
CACAATGGCACGATAAACCCCCAACCCCAACAGGGTAAGAATTCCCCCCATTACTA
GGGCATACCAGAAAGCCAATTGCAGACGACTACGGGCAAAGAGGCGACGGGTATTC
ATGGCGATAGGGTGAACCGATAGCCTTGACCGGGAACTGTTTTAATTGGGCAAGGA
CAATTTTGTTGAGCTAGCTTGCGTCGTATCAAACGCATTTGGGCCGCCACCACATTA
CTCATGGGCTCCTCATCAAGATCCACAGTTGTTGCCGGATCTTGCTACCGGAAATG
ATCCGCTCTGGGTTTTGCATCAGATATTGAAAAATTTGAAATTCTCTTACGGTTAAA
GCAATTTCCTGTCTTTCTAGGTTTAGTGGCTCCGAGATAGTTACCGATAACAGATTAT
TACTGGGATCAAGGCTGAAGTTGCCCAAAGTTAAAATTTGCGGTTGGAATTGTGGCG
ATCGCCGTTGTAGTGCCCGCAGTCTTGCTAATAGCTCTGCCATCACAAACGGTTTGT
TAGATAGTCATCTGCCCCGGCATCTAGTCCTTCGACACGGTTTTCCGGTTCTCCTAAC
GCTGTTAACATCAACACCGGCAAGGAATTACCCTGGGTTCTCAGTTTTTGACAGAGT
TCCAAACCCGATAATCCCGGCAGTAACCAATCCACAATGGCAAGGGTGTATTCCGTC
CATTGATTTTCCAAATAATCCCAAGCTTGGGAGCCATCCGTCACCCAATCCACCACA
TACTTTTCACTAACTAGCACTTTCTTAATAGCCATTCCCAAATCCGTCTCATCTTCCA
CCAGCAAAATTCGCATCGCCTCTGCCTTTTTTATAACGGTCTGATCTTAGCGGGGGA
AGGAGATTTTCACCTGAATTTCATACCCCCTTTGGCAGACTGGGAAAATCTTGGACA
AATTAGGAGGAAAACCAT
```

What is claimed is:

1. An engineered photosynthetic microbe comprising a recombinant acyl-CoA synthetase (EC 6.2.1.3) and a recombinant wax synthase (EC 2.3.1.75), wherein exposure of the engineered photosynthetic microbe to light and inorganic carbon results in incorporation of an alcohol into fatty acid esters produced by said engineered photosynthetic microbe, wherein at least one of said fatty acid esters is selected from the group consisting of a tetradecanoic acid ester, a Δ9-hexadecenoic acid ester, a hexadecanoic acid ester, a heptadecanoic acid ester, a Δ9-octadecenoic acid ester, and an octadecanoic acid ester, and wherein the amount of said fatty acid esters produced by said engineered photosynthetic microbe is increased relative to the amount of fatty acid esters produced by an otherwise identical cell lacking said recombinant acyl-CoA synthetase or recombinant wax synthase.

2. The microbe of claim 1, wherein said engineered photosynthetic microbe further comprises a recombinant thioesterase.

3. The microbe of claim 1, wherein said alcohol is an exogenously added alcohol selected from the group consisting of methanol, ethanol, propanol, isopropanol, butanol, hexanol, cyclohexanol, and isoamyl alcohol.

4. The microbe of claim 3, wherein said esters include a hexadecanoic acid ester and an octadecanoic acid ester.

5. The microbe of claim 3, wherein the amount of hexadecanoic acid ester produced is between 1.5 and 10 fold greater than the amount of octadecanoic acid ester.

6. The microbe of claim 3, wherein at least 50% of the esters produced by said engineered photosynthetic microbe are hexadecanoic acid esters.

7. The microbe of claim 3, wherein said alcohol is butanol.

8. The microbe of claim 7, wherein the yield of fatty acid butyl esters is at least 5% dry cell weight.

9. The microbe of claim 3, wherein said alcohol is ethanol.

10. The microbe of claim 9, wherein the yield of ethyl esters is at least 1% dry cell weight.

11. The microbe of claim 3, wherein said alcohol is methanol.

12. The microbe of claim 1, wherein said engineered photosynthetic microbe is a thermophilic photosynthetic microbe.

13. The microbe of claim 1, wherein said engineered photosynthetic microbe is a cyanobacterium.

14. The microbe of claim 1, wherein said engineered photosynthetic microbe is *Thermosynechococcus elongatus* BP-1.

15. The microbe of claim 1, wherein said engineered photosynthetic microbe is *Synechococcus* sp. PCC 7002.

16. The microbe of claim 1, wherein the engineered photosynthetic microbe further comprises a recombinant RND-type transporter.

17. The microbe of claim 16, wherein said RND-type transporter is a TolC-AcrAB transporter.

18. The microbe of claim 1, wherein said engineered photosynthetic microbe further comprises a deletion or knockout of an endogenous gene encoding a long-chain-fatty-acid ACP ligase.

19. The microbe of claim 18, wherein said gene encoding said endogenous fatty acid ACP ligase is the aas gene.

20. The microbe of claim 1, further comprising a recombinant gene encoding pyruvate decarboxylase and a recombinant gene encoding alcohol dehydrogenase.

* * * * *